(12) United States Patent
Stolle et al.

(10) Patent No.: US 6,723,718 B2
(45) Date of Patent: Apr. 20, 2004

(54) SUBSTITUTED α, β-ANELLATED BUTYROLACTONES

(75) Inventors: Andreas Stolle, Wuppertal (DE); Horst-Peter Antonicek, Bergisch Gladbach (DE); Stephen Lensky, Kurten (DE); Arnd Voerste, Cologne (DE); Thomas Müller, Bonn (DE); Jörg Baumgarten, Wuppertal (DE); Karsten von dem Bruch, Leverkusen (DE); Gerhard Müller, Leverkusen (DE); Udo Stropp, Haan (DE); Ervin Horváth, Leverkusen (DE); Jean-Marie-Viktor de Vry, Rösrath (DE); Rudy Schreiber, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 9 days.

(21) Appl. No.: 10/206,166

(22) Filed: Jul. 25, 2002

(65) Prior Publication Data

US 2003/0158424 A1 Aug. 21, 2003

Related U.S. Application Data

(63) Continuation of application No. 09/600,355, filed as application No. PCT/EP99/00132 on Jan. 12, 1999, now Pat. No. 6,462,074.

(30) Foreign Application Priority Data

Jan. 17, 1998 (DE) .......................... 198 01 646

(51) Int. Cl.[7] .................. A61K 31/5377; C07D 413/08; C07D 413/12
(52) U.S. Cl. ................ 514/231.5; 514/235.5; 514/233.5; 544/111; 544/147
(58) Field of Search .......................... 514/231.5, 235.5, 514/235.8; 544/111, 147, 107

(56) References Cited

U.S. PATENT DOCUMENTS

| 5,688,826 A | 11/1997 | Massey et al. ............... 514/433 |
| 5,717,109 A | 2/1998 | Arnold et al. ............... 548/511 |
| 5,843,988 A | 12/1998 | Annoura et al. ............ 514/454 |

FOREIGN PATENT DOCUMENTS

| EP | 0656345 | 6/1995 | ......... C07C/229/36 |
| EP | 0658539 | 6/1995 | ......... C07C/229/24 |
| EP | 0774454 | 5/1997 | ......... C07C/229/50 |
| EP | 0774461 | 5/1997 | ......... C07D/209/52 |
| WO | 9515941 | 6/1905 | ......... C07C/229/36 |
| WO | 9210583 | 6/1992 | ........... C12P/21/06 |
| WO | 9515099 | 6/1995 | ............. A47C/5/12 |
| WO | 9515940 | 6/1995 | ......... C07C/229/24 |
| WO | 9525110 | 9/1995 | ......... C07D/513/02 |
| WO | 9605818 | 2/1996 | ......... A61K/31/135 |
| WO | 9607405 | 3/1996 | .......... A61K/31/19 |
| WO | 9615099 | 5/1996 | ......... C07C/229/46 |
| WO | 9615100 | 5/1996 | ......... C07C/229/46 |
| WO | 9701790 | 1/1997 | ......... G02F/1/1337 |
| WO | 9705109 | 2/1997 | ......... C07D/209/18 |
| WO | 9705137 | 2/1997 | ......... C07D/473/04 |

OTHER PUBLICATIONS

Conn, P. J., and Pin J.–P., "Pharmacology and Functions of Metabotropic Glutamate Receptors", Annu. Rev. Pharmacol. Toxicol., 37:205–237 (1997).

Chavis, P., Nooney, J. M., Bockaert, J., Fagni, L., Feltz, A., and Bossu, J. L., "Facilitatory Coupling between a Glutamate Metabotropic Receptor and Dihydropyridine–Sensitive Calcium Channels in Cultured Cerebellar Granule Cells", The Journal of Neuroscience, 15(1): 135–143 (Jan. 1995).

Chavis, P., Shinozaki, H., Bockaert, J., and Fagni, L., "The Metabotropic Gultamate Receptor Types 2/3 Inhibit L–Type Calcium Channels via a Pertussis Toxin–Sensitive G–Protein in Cultured Cerebellar Granule Cells", The Journal of Neuroscience, 14(11): 7067–7076 (Nov. 1994).

Ghauri, M., Chapman, A. G., and Meldrun, B. S., "Convulsant and anticonvulsant actions of agonists and antagonists of group III mGluRs", NeuroReport, 7(9): 1469–1474 (Jun. 1996).

Moghaddam, B., and Adams, B. W., "Reversal of Phencyclidine Effects by a Group II Metabotropic Glutamate Receptor Agonist in Rats", Science, 281: 1349–1352 (Aug. 1998).

Kronthaler, U. O., and Schmidt, W. J., "1S,3R–ACPD has cataleptogenic effects and reverses MK–801– and less pronounced, D,L–amphetamine–induced locomotion", European Journal of Pharmacology, 316: 129–136 (1996).

Hudlicky, T.; Bhaskar Reddy, D.; and Govindan, S. V., "Intramolecular Cyclopentene Annulation. 3.[1] Synthesis and Carbon–13 Nuclear Magnetic Resonance Spectroscopy of Bicyclic Cyclopentene Lactones as Potential Perhydroazulene and/or Monoterpene Synthons", J. Org. Chem. 48: 3422–3428 (1983).

Primary Examiner—Taofiq Solola
(74) Attorney, Agent, or Firm—Susan M. Pellegrino

(57) ABSTRACT

The present invention relates to novel substituted α,β-fused butyrolactones, to processes for their preparation and to their use for the prevention and/or treatment of disorders caused by hyper- or hypofunction of the glutamatergic system, in particular of cerebral ischaemias, craniocerebral trauma, states of pain or CNS-mediated spasms.

11 Claims, No Drawings

SUBSTITUTED α, β-ANELLATED BUTYROLACTONES

This application is a continuing application of U.S. Ser. No. 09/600,355 filed Jul. 14, 2000 now U.S. Pat. No. 6,462,074, which is a 371 of PCT/EP99/00132 filed Jan. 12, 1999.

The present invention relates to α,β-fused butyrolactones, to processes for their preparation and to their use as pharmaceuticals.

The amino acid L-glutamate is the most important excitatory neurotransmitter in the brain. Glutamate receptors can be divided into two major classes: 1 ionotropic receptors which control ion channels directly and 2. metabotropic receptors (mGluRs).

Metabotropic glutamate receptors are a heterogeneous class of G-protein-coupled receptors. Pre- and postsynaptically, they modulate the release of glutamate and the sensitivity of the cell to glutamate, respectively. The effects are caused via different second-messenger cascades. This response, in turn, has an effect on the ionotropic glutamate receptors.

Presently, 8 different subtypes of metabotropic glutamate receptors are known, differing in the second-messenger cascade, pharmacology and the localization in the brain (review in: Ann. Rev. Pharmacol. Toxicol. 1997, 37, 205).

The present invention relates to α,β-fused butyrolactones of the general formula (I)

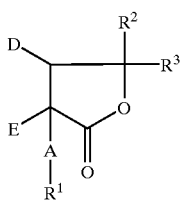

(I)

in which
A represents radicals of the formulae —CH$_2$—, —CO—, —CR$^4$(OH)— or —(CH$_2$)$_a$—CHR$^5$—,
in which
a represents a number 0, 1, 2, 3 or 4,
R$^4$ represents hydrogen or (C$_1$–C$_6$)-alkyl
and
R$^5$ represents phenyl,
or
represents (C$_2$–C$_8$)-alkanediyl, (C$_2$–C$_6$)-alkenediyl or (C$_2$–C$_6$)-alkinediyl,
R$^1$ represents hydrogen, (C$_3$–C$_6$)-cycloalkyl or represents a 5- to 6-membered heterocycle which may contain up to 3 heteroatoms from the group consisting of S, O, N and/or a radical of the formula —NR$^6$,
in which
R$^6$ represents hydrogen or methyl,
or
represents a 5- to 6-membered benzo-fused heterocycle which may contain up to 2 heteroatoms from the group consisting of S, O, N and/or a radical of the formula —NR$^7$, and which may be attached both via the phenyl ring and via the heterocycle,
in which
R$^7$ has the meaning of R$^6$ given above and is identical to or different from this meaning,
or
represents radicals of the formulae

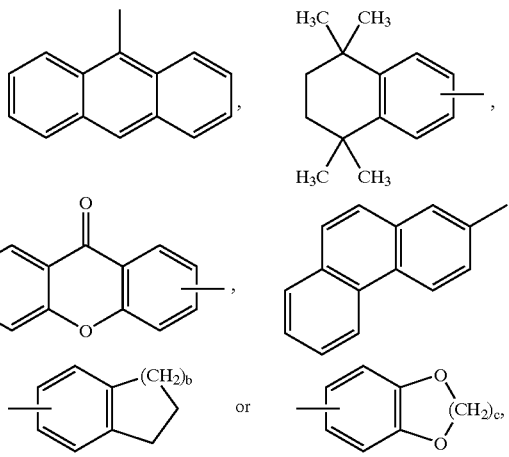

in which
b and c are identical or different and represent a number 1 or 2,
or
represents (C$_6$–C$_{10}$)-aryl,
where all of the ring systems listed above are optionally mono- to polysubstituted by identical or different substituents selected from the group consisting of halogen, cyano, nitro, trifluoromethyl, hydroxyl, (C$_1$–C$_6$)-alkoxy, (C$_1$–C$_6$)-alkyl-carbonyloxy and (C$_3$–C$_6$)-cycloalkyl, phenyl, phenoxy, benzyloxy and a 5- to 6-membered aromatic heterocycle having up to 3 heteroatoms from the group consisting of S, N and/or O, which for their part may be substituted up to three times by identical or different substituents from the group consisting of cyano and halogen,
and/or are substituted by (C$_1$–C$_6$)-alkyl and (C$_2$–C$_6$)-alkylene, which for their part may be substituted by halogen, (C$_6$–C$_{10}$)-aryl or by radicals of the formula —SR$^8$, —OR$^9$ or —NR$^{10}$R$^{11}$ or

in which
R$^8$ represents (C$_1$–C$_6$)-alkyl or phenyl,
R$^9$ represents hydrogen or (C$_1$–C$_6$)-alkyl,
and
R$^{10}$ and R$^{11}$ are identical or different and represent hydrogen, phenyl or (C$_1$–C$_6$)-alkyl, which is optionally substituted by phenyl, which for its part may be mono- to polysubstituted by identical or different substituents from the group consisting of halogen, nitro, hydroxyl and (C$_1$–C$_6$)-alkoxy,
or
R$^{10}$ and R$^{11}$ together with the nitrogen atom form a radical of the formula

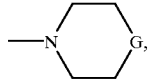

in which
G represents an oxygen atom, a —CH$_2$— group or a radical of the formula —NR$^{12}$—,
in which
R$^{12}$ represents hydrogen, phenyl, benzyl, (C$_1$–C$_6$)-alkyl, (C$_1$–C$_6$)-alkoxy-carbonyl or a 5- to 6-membered aromatic heterocycle having up to 3 heteroatoms from the group consisting of S, N and/or O,
and/or are substituted by groups of the formulae —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$,
in which
R$^{13}$ represents hydrogen, or represents (C$_1$–C$_9$)-alkyl or (C$_2$–C$_6$)-alkenyl, which for their part may be substituted by radicals of the formulae

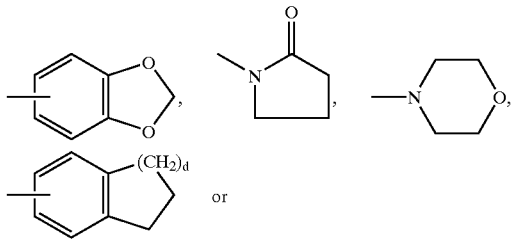

(C$_6$–C$_{10}$)-aryl or by a 5- to 7-membered aromatic heterocycle having up to 3 heteroatoms from the group consisting of S, N and/or O,
in which
d represents a number 1 or 2,
or
represents (C$_6$–C$_{10}$)-aryl, which is optionally substituted by phenyl, which for its part may be substituted by cyano or halogen,
R$^{14}$ and R$^{15}$ are identical or different and represent hydrogen, (C$_3$–C$_6$)-cycloalkyl, phenyl or (C$_1$–C$_6$)-alkyl, which is optionally substituted by (C$_3$–C$_6$)-cycloalkyl or phenyl, which for its part may be mono- to polysubstituted by identical or different substituents from the group consisting of halogen, hydroxyl or (C$_1$–C$_6$)-alkoxy,
R$^{16}$ represents hydrogen or (C$_1$–C$_6$)-alkyl,
R$^{17}$ represents hydrogen, adamantyl, (C$_3$–C$_8$)-cycloalkyl, (C$_2$–C$_6$)-alkenyl or (C$_1$–C$_{12}$)-alkyl which is optionally substituted by adamantyl, (C$_3$–C$_6$)-cycloalkyl, (C$_6$–C$_{10}$)-aryl, phenoxy or a 5- to 6-membered aromatic heterocycle having up to 4 heteroatoms from the group consisting of S, N and/or O, where aryl and the heterocycle for their part may be mono- to polysubstituted by identical or different substituents from the group consisting of (C$_1$–C$_6$)-alkyl, (C$_1$–C$_6$)-alkoxy, hydroxyl, nitro or halogen,
and/or alkyl is optionally substituted by a radical of the formula

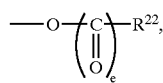

in which
e represents a number 0 or 1 and
R$^{22}$ represents (C$_1$–C$_6$)-alkyl or (C$_6$–C$_{10}$)-aryl, which is optionally mono- to polysubstituted by identical or different substituents from the group consisting of halogen, nitro, hydroxyl and (C$_1$–C$_6$)-alkoxy,
or
represents (C$_6$–C$_{10}$)-aryl or a 5- to 6-membered aromatic heterocycle having up to 3 heteroatoms from the group consisting of S, N and/or O, which for their part may optionally be mono- to polysubstituted by identical or different substituents from the group consisting of (C$_1$–C$_6$)-alkoxy, (C$_1$–C$_6$)-alkyl, hydroxyl, nitro and halogen,
or
represents a radical of the formula

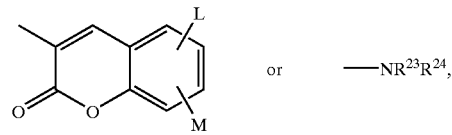

in which
L and M are identical or different and represent hydrogen or halogen,
R$^{23}$ and R$^{24}$ have the meaning of R$^{10}$ and R$^{11}$ given above and are identical to or different from this meaning,
R$^{18}$ has the meaning of R$^{16}$ given above and is identical to or different from this meaning,
R$^{19}$ represents (C$_3$–C$_8$)-cycloalkyl, or
represents (C$_1$–C$_8$)-alkyl or (C$_2$–C$_8$)-alkenyl, which for their part are optionally substituted by substituents selected from the group consisting of halogen, phenyl, hydroxyl, morpholinyl, (C$_3$–C$_8$)-cycloalkyl and by a group of the formula —SiR$^{25}$R$^{26}$R$^{27}$,
in which
R$^{25}$, R$^{26}$ and R$^{27}$ are identical or different and represent (C$_1$–C$_6$)-alkyl,
R$^{20}$ and R$^{21}$ are identical or different and represent hydrogen, adamantyl, (C$_3$–C$_8$)-cycloalkyl, phenyl, phenoxy-substituted phenyl or a 5- to 6-membered, aromatic heterocycle having up to 3 heteroatoms from the group consisting of S, N and/or O, or
represent (C$_2$–C$_8$)-alkenyl, (C$_1$–C$_{12}$)-alkyl or (C$_2$–C$_6$)-alkinyl, which are optionally substituted by hydroxyl, (C$_3$–C$_6$)-cycloalkyl, (C$_1$–C$_6$)-alkoxy, halogen, hydroxyl, trifluoromethyl, phenyl or by a 5- to 6-membered aromatic heterocycle having up to 3 heteroatoms from the group consisting of S, N and/or O, where the ring systems are optionally substituted up to 2 times by identical or different substituents from the group consisting of (C$_1$–C$_6$)-alkoxy, (C$_1$–C$_6$)-alkoxycarbonyl, halogen, phenoxy, hydroxyl and (C$_1$–C$_6$)-alkyl,
and/or the alkyl listed under R$^{20}$/R$^{21}$ is optionally substituted by radicals of the formulae

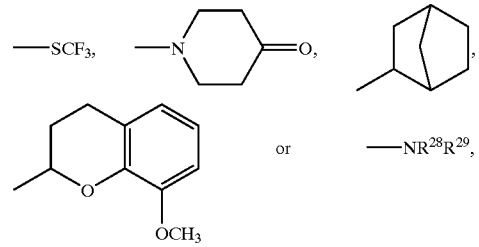

in which
R$^{28}$ and R$^{29}$ are identical or different and represent hydrogen or (C$_1$–C$_6$)-alkyl, or represents a radical of the formula

in which
R$^{30}$ has the meaning of R$^{12}$ given above and is identical to or different from this meaning,
or
R$^{20}$ and R$^{21}$ together with the nitrogen atom form a radical of the formula

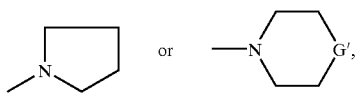

in which
G' has the meaning of G given above and is identical to or different from this meaning,
R$^2$ and R$^3$ are identical or different and represent hydrogen or (C$_1$–C$_6$)-alkyl,
and
D and E together form radicals of the formulae

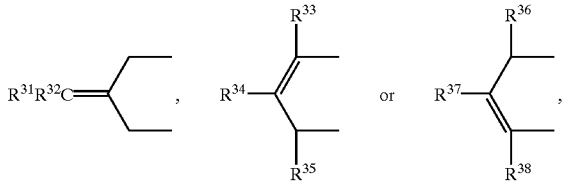

in which
R$^{31}$, R$^{32}$, R$^{33}$, R$^{34}$, R$^{35}$, R$^{36}$, R$^{37}$ and R$^{38}$ are identical or different and represent hydrogen, phenyl or (C$_1$–C$_6$)-alkyl,
and their pharmaceutically acceptable salts.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereoisomerically uniform components in a known manner.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine, 1-ephenamine or methylpiperidine.

In the context of the invention, (C$_3$–C$_8$)-cycloalkyl and (C$_3$–C$_6$)-cycloalkyl represent cyclopropyl, cyclopentyl, cyclobutyl, cyclohexyl, cycloheptyl or cyclooctyl. Preferred examples which may be mentioned are: cyclopropyl, cyclopentyl, cyclohexyl or cycloheptyl.

In general, (C$_6$–C$_{10}$)-aryl represents an aromatic radical having 6 to 10 carbon atoms. Preferred aryl radicals are phenyl and naphthyl.

In the context of the invention, (C$_1$–C$_{12}$)-alkyl, (C$_1$–C$_9$)-alkyl, (C$_1$–C$_8$)-alkyl and (C$_1$–C$_6$)-alkyl represent a straight-chain or branched alkyl radical having 1 to 12, 1 to 9, 1 to 8 and 1 to 6 carbon atoms, respectively. Preference is given to a straight-chain or branched alkyl radical having 1 to 6 carbon atoms. Examples which may be mentioned are: methyl, ethyl, n-propyl, isopropyl, t-butyl, n-pentyl and n-hexyl.

In the content of the invention, (C$_2$–C$_8$)-alkanediyl represents a straight-chain or branched alkanediyl radical having 2 to 8 carbon atoms. Preference is given to a straight-chain or branched alkanediyl radical having 2 to 6 carbon atoms, particularly preferably 2 to 4 carbon atoms. Examples which may be mentioned are ethylene, propylene, propane-1,2-diyl, propane-2,2-diyl, butane-1,3-diyl, butane-2,4-diyl, pentane-2,4-diyl, 2-methyl-pentane-2,4-diyl.

In the content of the invention, (C$_2$–C$_6$)-alkenediyl represents a straight-chain or branched alkenediyl radical having 2 to 6 carbon atoms, preferably 2 to 4 carbon atoms, particularly preferably 3 carbon atoms. Examples which may be mentioned are ethene-1,2-diyl, ethene-1,1-diyl, propene-1,1-diyl, propene-1,2-diyl, propene-1,3-diyl, propene-3,3-diyl, propene-2,3-diyl, but-2-ene-1,4-diyl, pent-2-ene-1,4-diyl, hex-2-ene-1,4-diyl.

In the context of the invention, (C$_2$C$_6$)-alkinediyl represents a straight-chain or branched alkinediyl radical having 2 to 6 carbon atoms, preferably 2 to 4 carbon atoms, particularly preferably 2 to 3 carbon atoms. Examples which may be mentioned are ethine-1,2-diyl, propine-1,3-diyl, but-2-ine-1,4-diyl, pent-2-ine-1,4-diyl, hex-2-ine-1,4-diyl.

In the context of the invention, (C$_1$–C$_6$)-alkoxy represents a straight-chain or branched alkoxy radical having 1 to 6 carbon atoms. Preference is given to a straight-chain or branched alkoxy radical having 1 to 4 carbon atoms. Examples which may be mentioned are: methoxy, ethoxy, n-propoxy, isopropoxy, t-butoxy, n-pentoxy and n-hexoxy.

In the context of the invention, (C$_1$–C$_6$)-alkoxycarbonyl represents a straight-chain or branched alkoxycarbonyl radical having 1 to 6 carbon atoms. Preference is given to a straight-chain or branched alkoxycarbonyl radical having 1 to 4 carbon atoms. Examples which may be mentioned are: methoxycarbonyl, ethoxycarbonyl, n-propoxycarbonyl, isopropoxycarbonyl and t-butoxycarbonyl.

In the context of the invention, (C$_2$–C$_8$)-alkenyl and (C$_2$–C$_6$)-alkenyl represent a straight-chain or branched alkenyl radical having 2 to 8 carbon atoms and 2 to 6 carbon atoms, respectively. Preference is given to a straight-chain or branched alkenyl radical having 2 to 4 carbon atoms. Examples which may be mentioned are: vinyl, allyl, isopropenyl and n-but-2-en-1-yl.

In the context of the invention, (C$_2$–C$_6$)-alkinyl represents a straight-chain or branched alkinyl radical having 2 to 6 carbon atoms. Preference is given to a straight-chain or branched alkinyl radical having 2 to 4 carbon atoms. Examples which may be mentioned are: ethinyl, n-prop-2-in-1-yl and n-but-2-in-1-yl.

In the context of the invention, a 5- to 6-membered heterocycle generally represents a 5- to 6-membered, optionally also aromatic, heterocycle which may contain up to 3 heteroatoms from the group consisting of S, O and/or N or a radical of the formula —NH or —NCH$_3$. Examples which may be mentioned are: pyridyl, pyrimidyl, pyridazinyl, thienyl, furyl, pyrrolyl, thiazolyl, oxazolyl, imidazolyl, piperidinyl or morpholinyl. Preference is given to pyridyl, pyrimidyl, pyridazinyl, furyl and thiazolyl.

In the context of the invention, a 5- to 6-membered, benzo-fused heterocycle generally represents a 5- to 6-membered, preferably 5-membered heterocycle having up to 2 heteroatoms from the group consisting of S, O, N and/or a radical of the formula —NH, whose ring carbon atoms are the attachment points for the benzene ring. Examples which may be mentioned are: indolyl, benzimidazolyl, benzothiophenyl, benzofuranyl, benzoxazolyl, quinolyl, quinoxalinyl or quinazolyl. Preference is given to benzimidazolyl, quinolyl, quinoxalinyl, quinazolyl, benzothiophenyl and benzofuranyl.

Preference is given to compounds of the general formula (I) according to the invention, in which
A represents radicals of the formulae —CH$_2$—, —CO—, —CR$^4$(OH)— or —(CH$_2$)$_a$—CHR$^5$—,
in which
a represents a number 0, 1, 2 or 3,
R$^4$ represents hydrogen or (C$_1$–C$_4$)-alkyl
and
R$^5$ represents phenyl,
or
represents (C$_2$–C$_6$)-alkanediyl, (C$_2$–C$_4$)-alkenediyl or (C$_2$–C$_4$)-alkinediyl,
R$^1$ represents hydrogen, cyclopropyl, cyclopentyl or cyclohexyl, or represents benzofuranyl, benzothiophenyl, benzimidazolyl, thienyl, furyl, quinazolyl, quinoxalinyl or quinolyl,
or
represents radicals of the formulae

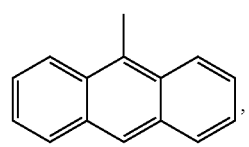 , 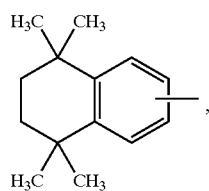 ,

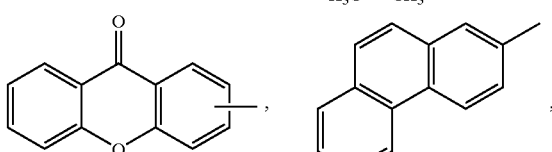

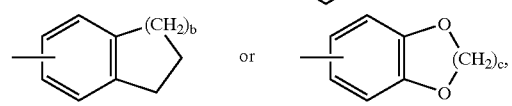

in which
b and c are identical or different and represent a number 1 or 2,
or
represents phenyl or naphthyl,
where all of the ring systems listed above are optionally mono- to polysubstituted by identical or different substituents selected from the group consisting of fluorine, chlorine, bromine, iodine, cyano, nitro, trifluoromethyl, hydroxyl or (C$_1$–C$_5$)-alkoxy, (C$_1$–C$_5$)-alkyl-carbonyloxy, cyclopropyl, cyclopentyl, cyclohexyl, phenyl, phenoxy, pyridyl, pyrimidyl, pyridazinyl, thienyl, furyl or benzyloxy, which for their part may be substituted up to three times by identical or different substituents from the group consisting of cyano, fluorine, chlorine, bromine and iodine, and/or are substituted by (C$_1$–C$_5$)-alkyl and (C$_2$–C$_4$)-alkenyl, which for their part may be substituted by fluorine, chlorine, bromine, iodine, phenyl, naphthyl or by radicals of the formula —SR$^8$, —OR$^9$ or —NR$^{10}$R$^{11}$
or

in which
R$^8$ represents (C$_1$–C$_4$)-alkyl or phenyl,
R$^9$ represents hydrogen or (C$_1$–C$_4$)-alkyl,
and
R$^{10}$ and R$^{11}$ are identical or different and represent hydrogen, phenyl or (C$_1$–C$_4$)-alkyl, which is optionally substituted by phenyl, which for its part may be mono- to polysubstituted by identical or different substituents from the group consisting of fluorine, chlorine, bromine, nitro, hydroxyl and (C$_1$–C$_4$)-alkoxy,
or
R$^{10}$ and R$^{11}$ together with the nitrogen atom form a radical of the formula

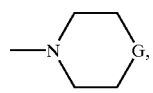

in which
G represents an oxygen atom, a —CH$_2$— group or a radical of the formula —NR$^{12}$—,
in which
R$^{12}$ represents hydrogen, phenyl, benzyl, (C$_1$–C$_4$)-alkyl, (C$_1$–C$_4$)-alkoxycarbonyl, pyridyl, pyrimidyl, pyridazinyl or furyl,
and/or are substituted by groups of the formulae —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$,
in which
R$^{13}$ represents hydrogen, or represents (C$_1$–C$_8$)-alkyl or (C$_2$–C$_5$)-alkenyl, which for their part may be substituted by radicals of the formulae

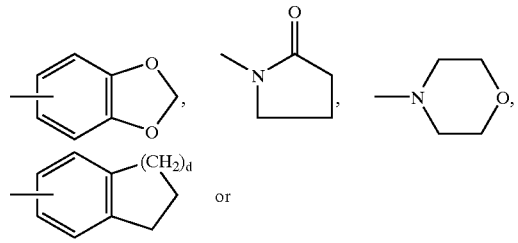

phenyl, naphthyl, pyridyl, thienyl or furyl,
in which
d represents a number 1 or 2, or represents phenyl or naphthyl, which are optionally substituted by phenyl, which for its part may be substituted by cyano, fluorine, chorine or bromine, $R^{14}$ and $R^{15}$ are identical or different and represent hydrogen, cyclopropyl, cyclopentyl, cyclohexyl, phenyl or $(C_1-C_5)$-alkyl, which is optionally substituted by cyclopropyl, cyclopentyl, cyclohexyl or phenyl, which for its part may be mono- to polysubstituted by identical or different substituents from the group consisting of fluorine, chlorine, bromine, hydroxyl or $(C_1-C_4)$-alkoxy, $R^{16}$ represents hydrogen or $(C_1-C_3)$-alkyl, $R^{17}$ represents hydrogen, adamantyl, cyclopropyl, cyclopentyl or cyclohexyl, or represents $(C_2-C_4)$-alkenyl or $(C_1-C_{10})$-alkyl, which is optionally substituted by adamantyl, cyclopropyl, cyclopentyl, cyclohexyl, phenyl, phenoxy-naphthyl, pyridyl, thienyl, tetrazolyl or furyl, where the ring systems for their part may be mono- to polysubstituted by identical or different substituents from the group consisting of $(C_1-C_4)$-alkyl, $(C_1-C_4)$-alkoxy, hydroxyl, nitro, fluorine, chlorine and bromine, and/or alkyl is optionally substituted by a radical of the formula

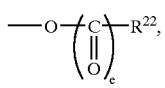

in which e represents a number 0 or 1 and $R^{22}$ represents $(C_1-C_4)$-alkyl, phenyl or naphthyl, which are optionally mono- to polysubstituted by identical or different substituents from the group consisting of fluorine, chlorine, bromine, nitro, hydroxyl and $(C_1-C_4)$-alkoxy, or represents phenyl, naphthyl, thienyl, furyl or pyridyl, which for their part may optionally be mono- to polysubstituted by identical or different substituents from the group consisting of $(C_1-C_4)$-alkoxy, $(C_1-C_4)$-alkyl, hydroxyl, nitro, fluorine, chlorine and bromine, or represents a radical of the formula

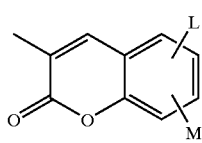

in which

L and M are identical or different and represent hydrogen, fluorine, chlorine or bromine, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents cyclopropyl, cyclopentyl or cyclohexyl, or represents $(C_1-C_7)$-alkyl or $(C_2-C_6)$-alkenyl, which for their part are optionally substituted by substituents selected from the group consisting of fluorine, chlorine, bromine, phenyl, hydroxyl, morpholinyl, cyclopropyl, cyclopentyl, cyclohexyl and by a group of the formula $-SiR^{25}R^{26}R^{27}$, in which $R^{25}$, $R^{26}$ and $R^{27}$ are identical or different and represent $(C_1-C_4)$-alkyl, $R^{20}$ and $R^{21}$ are identical or different and represent hydrogen, adamantyl, cyclopropyl, cyclopentyl, cyclohexyl, phenyl, phenoxy-substituted phenyl, pyridyl, furyl, thienyl, thiazolyl or pyrryl, or represent $(C_2-C_6)$-alkenyl, $(C_1-C_{10})$-alkyl or $(C_3-C_6)$-alkinyl, which are optionally substituted by hydroxyl, cyclopropyl, cyclopentyl, cyclohexyl, $(C_1-C_5)$-alkoxy, $(C_1-C_6)$-alkoxycarbonyl, fluorine, chlorine, bromine, hydroxyl, trifluoromethyl, phenyl, pyridyl, furyl, thienyl or pyrryl, where the ring systems are optionally substituted up to 2 times by identical or different substituents from the group consisting of $(C_1-C_4)$-alkoxy, fluorine, chlorine, bromine, phenoxy, hydroxyl or $(C_1-C_4)$-alkyl, and/or the alkyl listed under $R^{20}/R^{21}$ is optionally substituted by radicals of the formulae

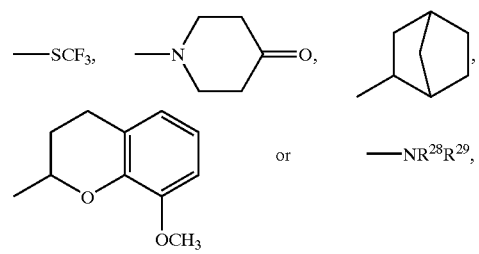

in which $R^{28}$ and $R^{29}$ are identical or different and represent hydrogen or $(C_1-C_4)$-alkyl, or represents a radical of the formula

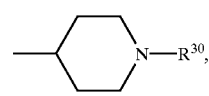

in which $R^{30}$ has the meaning of $R^{12}$ given above and is identical to or different from this meaning, or $R^{20}$ and $R^{21}$ together with the nitrogen atom form a radical of the formula

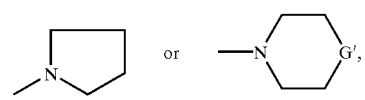

in which

G' has the meaning of C given above and is identical to or different from this meaning, $R^2$ and $R^3$ are identical or different and represent hydrogen or $(C_1-C_3)$-alkyl, and
D and E together form radicals of the formulae

[chemical structures showing R³¹R³²C= with R³³ and R³⁵ substituents; R³⁴-C=C-R³⁶/R³⁸ with R³⁷ substituent]

in which
R³¹, R³², R³³, R³⁴, R³⁵, R³⁶, R³⁷ and R³⁸ are identical or different and represent hydrogen, phenyl or (C₁–C₃)-alkyl,
and their pharmaceutically acceptable salts.

Particular preference is given to compounds of the general formula (I) according to the invention,
in which
A represents radicals of the formulae —CH₂—, —CO—, —CR⁴(OH)— or —(CH₂)$_a$—CHR⁵—,
in which
a represents a number 0, 1, 2 or 3,
R⁴ represents hydrogen or (C₁–C₃)-alkyl
and
R⁵ represents phenyl,
or
represents (C₂–C₄)-alkanediyl, propenediyl or (C₂–C₃)-alkinediyl,
R¹ represents hydrogen, cyclopropyl or cyclohexyl, or represents benzofuranyl, benzothiophenyl, benzimidazolyl, thienyl, quinazolyl or quinoxalinyl,
or
represents radicals of the formulae

[chemical structures: 9-methylanthracene; 1,1,4,4-tetramethyl-tetrahydronaphthalene with CH₃ groups; xanthone; methyl-phenanthrene; indane with (CH₂)$_b$; benzodioxole with (CH₂)$_c$]

in which
b and c are identical or different and represent a number 1 or 2,
or
represents phenyl or naphthyl,
where all of the ring systems listed above are optionally mono- to polysubstituted by identical or different substituents selected from the group consisting of fluorine, chlorine, bromine, iodine, cyano, nitro, trifluoromethyl or (C₁–C₄)-alkoxy, (C₁–C₄)-alkyl-carbonyloxy, cyclohexyl, phenyl, phenoxy, pyridyl, pyrimidyl, pyridazinyl or benzyloxy, which for their part may be substituted up to three times by identical or different substituents from the group consisting of cyano, fluorine, chlorine, bromine and iodine,
and/or are substituted by (C₁–C₄)-alkyl and (C₂–C₃)-alkenyl, which for their part may be substituted by chlorine, bromine, iodine or phenyl or by radicals of the formula —OR⁹ or —NR¹⁰R¹¹ or

[chemical structure: piperidone ring N—...=O]

in which
R⁹ represents hydrogen or (C₁–C₃)-alkyl,
and
R¹⁰ and R¹¹ are identical or different and represent hydrogen, phenyl or (C₁–C₃)-alkyl, which is optionally substituted by phenyl, which for its part may be substituted by chlorine, bromine, hydroxyl or (C₁–C₃)-alkoxy,
or
R¹⁰ and R¹¹ together with the nitrogen atom form a radical of the formula

[chemical structure: 6-membered ring with N and G]

in which
G represents an oxygen atom or a radical of the formula —NR¹²,
in which
R¹² represents hydrogen, phenyl, benzyl, (C₁–C₃)-alkyl, (C₁–C₃)-alkoxycarbonyl, pyridyl, pyrimidyl, pyridazinyl or furyl,
and/or are substituted by groups of the formulae —CO₂—R¹³, —NR¹⁴R¹⁵, —NR¹⁶CO—R¹⁷, —NR¹⁸CO₂—R¹⁹ and —CO—NR²⁰R²¹,
in which
R¹³ represents hydrogen, or represents (C₁–C₆)-alkyl or allyl, which for their part may be substituted by radicals of the formulae

[chemical structures: benzodioxole; N-methylpyrrolidinone; morpholine N—...=O; indane with (CH₂)$_d$]

or phenyl, naphthyl or pyridyl,
in which
d represents a number 1 or 2,
or
represents phenyl, which is optionally substituted by phenyl, which for its part may be substituted by cyano, chlorine or bromine,
R¹⁴ and R¹⁵ are identical or different and represent hydrogen, cyclohexyl, phenyl or (C₁–C₄)-alkyl, which is optionally substituted by cyclopropyl, cyclohexyl or phenyl, which for its part may be mono- to polysubstituted by identical or different substituents from the group consisting of chlorine and $(C_1-C_3)$-alkoxy, $R^{16}$ represents hydrogen, methyl or ethyl, $R^{17}$ represents hydrogen, adamantyl, cyclopentyl or cyclohexyl, or represents $(C_2-C_3)$-alkenyl or $(C_1-C_8)$-alkyl, which is optionally substituted by adamantyl, cyclopropyl, cyclopentyl, cyclohexyl, phenyl, phenoxy, thienyl or furyl, where the ring systems for their part may be mono- to polysubstituted by identical or different substituents from the group consisting of $(C_1-C_3)$-alkyl, $(C_1-C_3)$-alkoxy, hydroxyl, nitro, fluorine, chlorine and bromine, and/or alkyl is optionally substituted by a radical of the formula

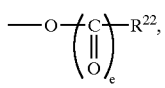

in which e is a number 0 or 1 and $R^{22}$ represents $(C_1-C_3)$-alkyl, phenyl or naphthyl, which are optionally mono- to polysubstituted by identical or different substituents from the group consisting of fluorine, chlorine, bromine, nitro, hydroxyl and $(C_1-C_3)$-alkoxy, or represents phenyl, naphthyl, thienyl or furyl, which for their part may optionally be mono- to polysubstituted by identical or different substituents from the group consisting of $(C_1-C_3)$-alkoxy, $(C_1-C_3)$-alkyl, nitro, fluorine, chlorine and bromine, or represents a radical of the formula

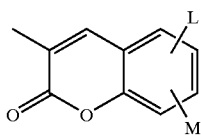

in which

L and M are identical or different and represent hydrogen, fluorine or chlorine, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents $(C_1-C_4)$-alkyl or $(C_3-C_5)$-alkenyl, which for their part are optionally substituted by substituents selected from the group consisting of chlorine, phenyl, hydroxyl, morpholinyl, cyclopropyl, cyclohexyl and by a group of the formula $-SiR^{25}R^{26}R^{27}$, in which $R^{25}$, $R^{26}$ and $R^{27}$ are identical and represent methyl, $R^{20}$ and $R^{21}$ are identical or different and represent hydrogen, adamantyl, cyclopropyl, cyclopentyl, cyclohexyl, phenyl, phenoxy-substituted phenyl, thiazolyl or pyrryl, or represent $(C_2-C_3)$-alkenyl, $(C_1-C_7)$-alkyl or $(C_3-C_5)$-alkinyl, which are optionally substituted by hydroxyl, cyclopropyl, cyclopentyl, cyclohexyl, $(C_1-C_3)$-alkoxy, hydroxyl, trifluoromethyl, phenyl, pyridyl, furyl, thienyl or pyrryl, where the ring systems are optionally substituted up to 2 times by identical or different substituents from the group consisting of $(C_1-C_3)$-alkoxy, $(C_1-C_6)$-alkoxycarbonyl, fluorine, chlorine, bromine, phenoxy, hydroxyl and $(C_1-C_3)$-alkyl, and/or the alkyl listed under $R^{20}/R^{21}$ is optionally substituted by radicals of the formulae

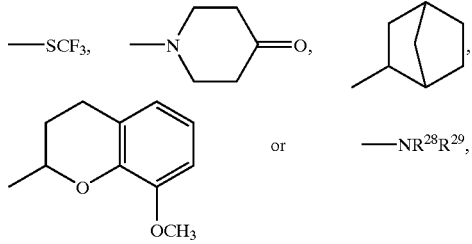

in which $R^{28}$ and $R^{29}$ are identical or different and represent hydrogen or $(C_1-C_3)$-alkyl, or $R^{20}$ or $R^{21}$ represents a radical of the formula

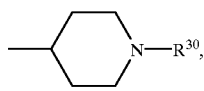

in which $R^{30}$ has the meaning of $R^{12}$ given above and is identical to or different from this meaning, or $R^{20}$ and $R^{21}$ together with the nitrogen atom form a radical of the formula

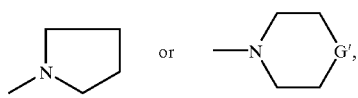

in which

G' has the meaning of G given above and is identical to or different from this meaning, $R^2$ and $R^3$ are identical or different and represent hydrogen or methyl, and D and E together form radicals of the formulae

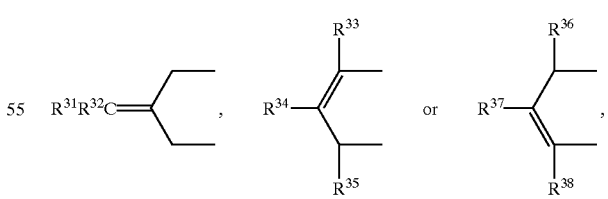

in which $R^{31}$, $R^{32}$, $R^{33}$, $R^{34}$, $R^{35}$, $R^{36}$, $R^{37}$ and $R^{38}$ are identical or different and represent hydrogen or methyl, and their pharmaceutically acceptable salts.

Particular preference is likewise given to compounds of the general formula (I) according to the invention in which A represents the $-CH_2-$ group.

Very particular preference is given to compounds of the general formula (I) according to the invention, in which A represents —CH$_2$—, R$^1$ represents phenyl or naphthyl, where all of the abovementioned ring systems are optionally mono- to polysubstituted by identical or different substituents selected from the group consisting of fluorine, chlorine, bromine, iodine, cyano, nitro, trifluoromethyl or (C$_1$–C$_4$)-alkoxy, and/or are substituted by (C$_1$–C$_4$)-alkyl, and/or are substituted by groups of the formulae —NR$^{16}$CO—R$^{17}$, —NR$^{18}$CO$_2$—R$^{19}$ and —CO—NR$^{20}$R$^{21}$, in which R$^{16}$ is hydrogen, R$^{17}$ is (C$_1$–C$_8$)-alkyl, which is optionally substituted by cyclopropyl, cyclopentyl, cyclohexyl, phenyl, thienyl or furyl, where the ring systems for their part may be mono- to polysubstituted by identical or different substituents from the group consisting of (C$_1$–C$_3$)-alkyl, (C$_1$–C$_3$)-alkoxy, hydroxyl, nitro, fluorine, chlorine and bromine, R$^{18}$ has the meaning of R$^{16}$ given above and is identical to or different from this meaning, R$^{19}$ represents (C$_1$–C$_4$)-alkyl or (C$_3$–C$_5$)-alkenyl, R$^{20}$ and R$^{21}$ are identical or different and represent hydrogen, (C$_2$–C$_3$)-alkenyl, (C$_1$–C$_7$)-alkyl or (C$_3$–C$_5$)-alkinyl, which are optionally substituted by phenyl, pyridyl, furyl, thienyl or pyrryl, where the ring systems are optionally substituted up to 2 times by identical or different substituents from the group consisting of (C$_1$–C$_3$)-alkoxy, fluorine, chlorine, bromine and (C$_1$–C$_3$)-alkyl, R$^2$ and R$^3$ represent hydrogen or methyl, and D and E together form radicals of the formulae

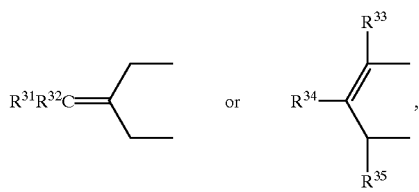

in which

R$^{31}$, R$^{32}$, R$^{33}$, R$^{34}$, R$^{35}$ represent hydrogen, and their pharmaceutically acceptable salts.

Very particular preference is given to the structures listed in the table below, which can be present in racemic form or enantiomerically pure:

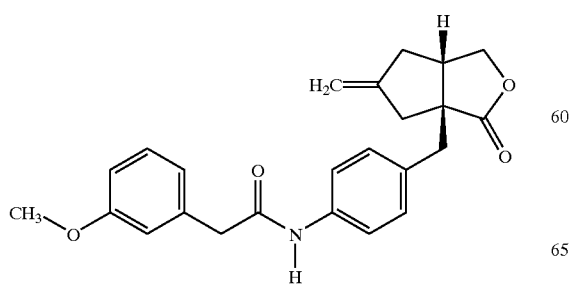

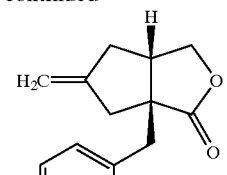
-continued

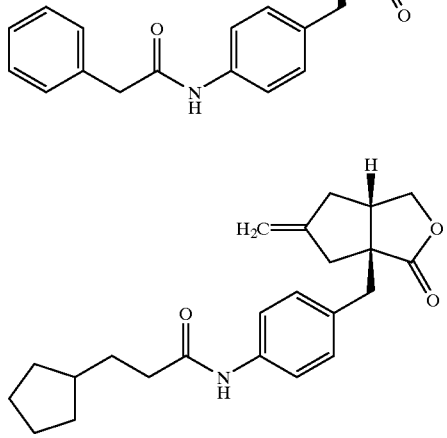

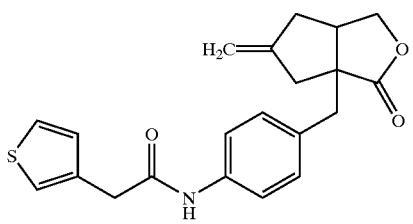

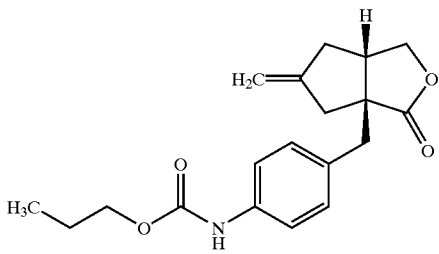

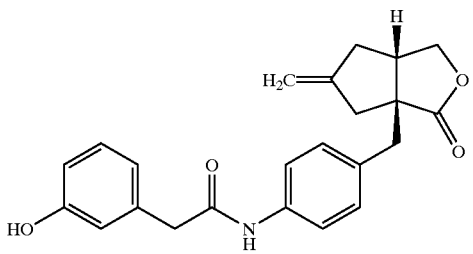

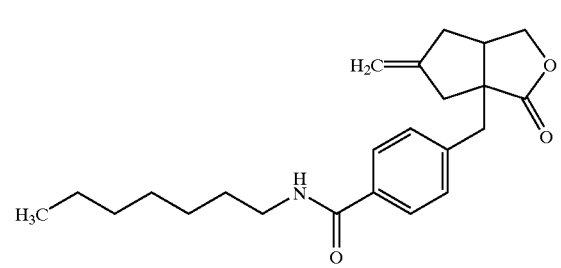

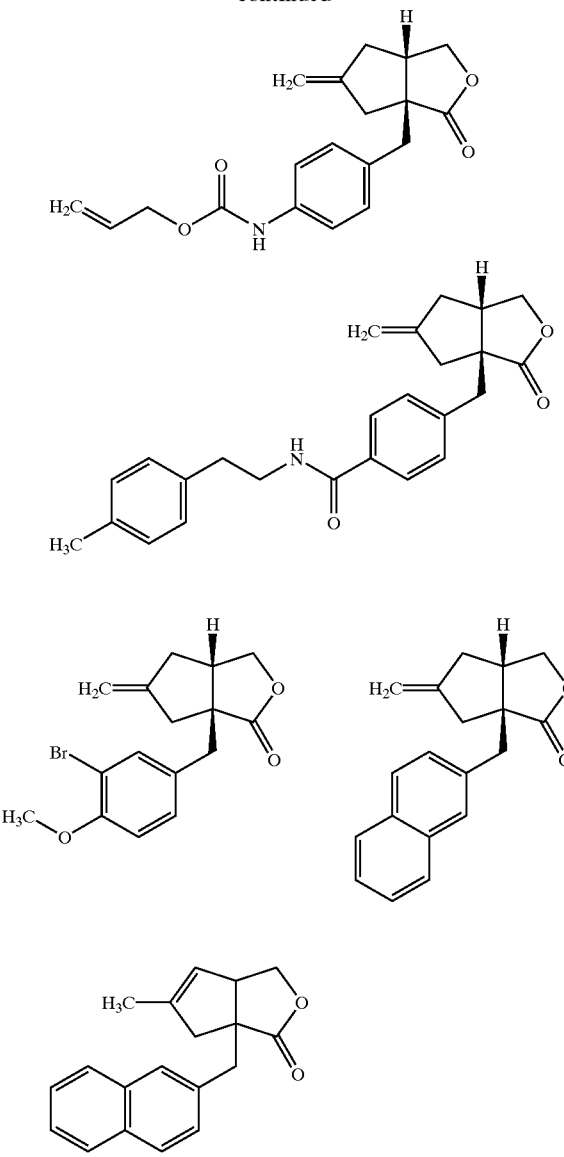

Moreover, we have found a process for preparing the compounds of the general formula (I) according to the invention, characterized in that compounds of the general formula (II)

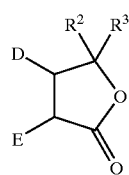

(II)

in which

D, E, R² and R³ are as defined above are reacted with compounds of the general formula (III),

T—A—R¹    (III)

in which

T represents halogen, preferably bromine, and

A and R¹ are as defined above, in inert solvents and in the presence of a base, and the substituent R¹ is, if appropriate, derivatized by customary methods.

The process according to the invention can be illustrated in an exemplary manner by the formula scheme below:

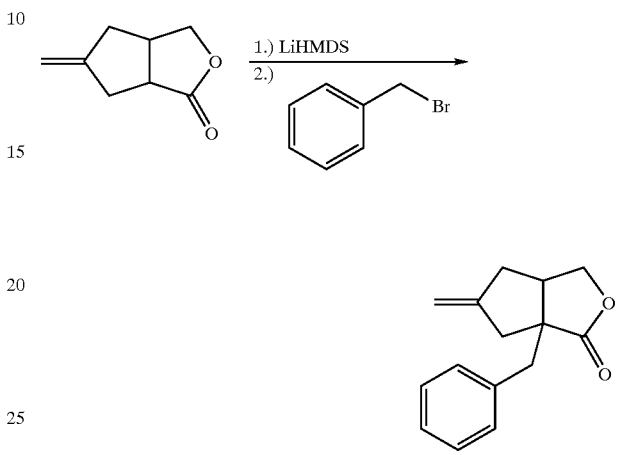

Suitable solvents are all inert solvents which do not change under the reaction conditions. These preferably include ethers, such as diethyl ether, dioxane, tetrahydrofuran, glycol dimethyl ether or diethylene glycol dimethyl ether. Particular preference is given to tetrahydrofuran.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate, or sodium methoxide or potassium methoxide, or sodium ethoxide or potassium ethoxide or potassium tert-butoxide, or amides, such as sodium amide, lithium bis-(trimethylsilyl)amide, lithium diisopropylamide, or organometallic compounds, such as butyllithium or phenyllithium. Preference is given to lithium diisopropylamide and lithium bis-(trimethylsilyl)amide.

Here, the base is employed in an amount of from 1 to 5, preferably from 1 to 2 mol, based on 1 mol of the compounds of the general formula (II).

The reaction is generally carried out in a temperature range of from −78° C. to reflux temperature, preferably from −78° C. to +20° C.

The reaction can be carried out under atmospheric, elevated or under reduced pressure (for example from 0.5 to 5 bar). In general, the reaction is carried out at atmospheric pressure.

Derivatizations in the context of the invention which may preferably be mentioned are reactions at the radical R¹ with substituent groups (C₁–C₆)-alkoxy, —NR¹⁴R¹⁵, —NR¹⁶—COR¹⁷—, —NR¹⁸—CO₂R¹⁹ and —CO—NR²⁰R²¹. Starting with the carboxylic-acid-substituted aryls, these are reacted with the corresponding amines in inert solvents and in the presence of an auxiliary. Also possible is a Curtius rearrangement in the presence of (C₆H₅O)₂—PON₃. Likewise, it is possible, starting from amino-substituted aryls (R¹), to introduce the amide function via the corresponding acid chlorides in the presence of bases or via the corresponding carboxylic acids in the presence of an auxiliary.

The derivatizations can be illustrated in an exemplary manner by the following formula scheme:

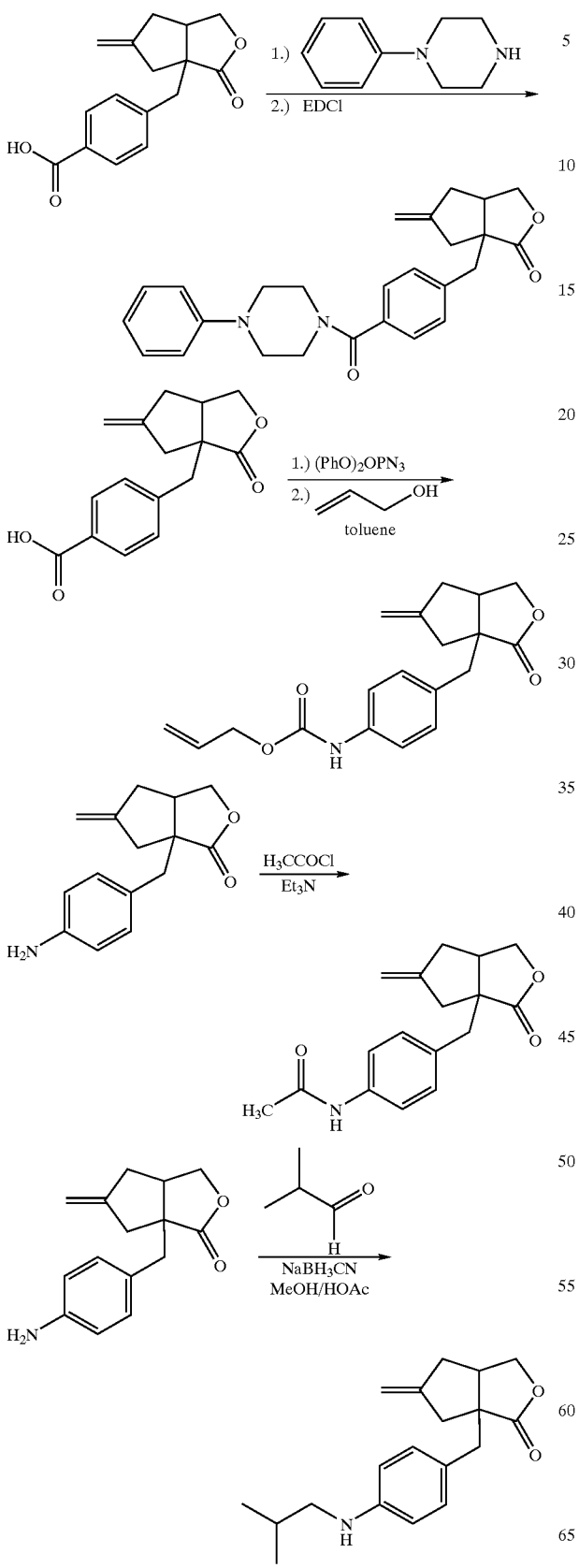

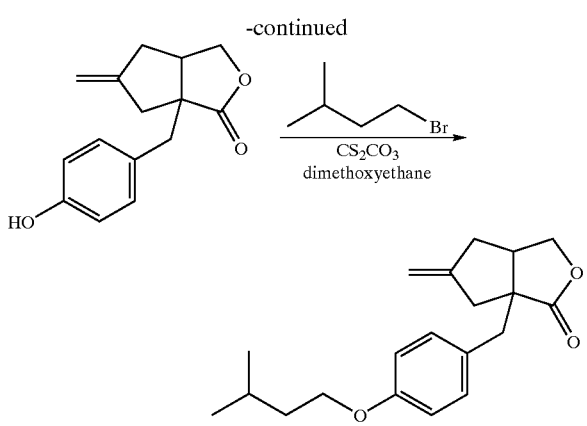

The amidation is generally carried out in inert solvents in the presence of a base and a dehydrating agent.

Here, suitable solvents are inert organic solvents which do not change under the reaction conditions. These include halogenated hydrocarbons, such as dichloromethane, trichloromethane, carbon tetrachloride, trichloroethane, tetrachloroethane, 1,2-dichloroethane or trichlorothylene, hydrocarbons, such as benzene, xylene, toluene, hexane, cyclohexane, or mineral oil fractions, nitromethane, dimethyl-formamide, acetonitrile or hexamethylphosphoric triamide. It is also possible to use mixtures of the solvents. Particular preference is given to dichloromethane.

Suitable bases for the derivatizations are the customary basic compounds. These preferably include alkali metal hydroxides or alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate, potassium carbonate, or alkali metal alkoxides, such as, for example, sodium methoxide or sodium ethoxide, potassium methoxide or potassium ethoxide or potassium tert-butoxide, or organic amines, such as benzyltrimethylammonium hydroxide, tetrabutylammonium hydroxide, pyridine, triethylamine or N-methylpiperidine.

The derivatizations are generally carried out in a temperature range of from −20° C. to 150° C., preferably at from 0° C. to 25° C.

The derivatizations are generally carried out under atmospheric pressure. However, it is also possible to carry out the processes under reduced pressure or under elevated pressure (for example in a range from 0.5 to 5 bar).

When carrying out the derivatizations, the bases are generally employed in an amount of from 1 to 3 mol, preferably from 1 to 1.5 mol, based on 1 mol of the carboxylic acid in question.

Suitable dehydrating agents are carbodiimides, such as, for example, diisopropyl-carbodiimide, dicyclohexylcarbodiimide or N-(3-dimethylaminopropyl)-N'-ethyl-carbodiimide hydrochloride, or carbonyl compounds, such as carbonyldiimidazole, or 1,2-oxazolium compounds, such as 2-ethyl-5-phenyl-1,2-oxazolium-3-sulphonate, or propanephosphoric anhydride or isobutyl chloroformate or benzotriazolyloxy-tris-(dimethylamino)phosphonium hexyfluorophosphate or diphenyl phosphonamidate or methanesulphonyl chloride, if appropriate in the presence of bases, such as triethylamine or N-ethylmorpholine or N-methylpiperidine or dicyclohexylcarbodiimide or N-hydroxysuccinimide.

Moreover, we have found a process for preparing the compounds of the general formula (I') according to the invention

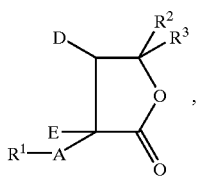
(I')

in which

A, $R^1$, $R^2$ and $R^3$ are as defined above,
and
D and E together form radicals of the formulae

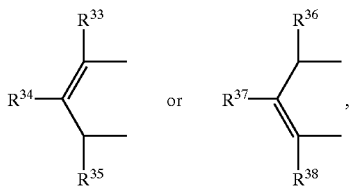

in which $R^{33}$, $R^{35}$, $R^{36}$ and $R^{38}$ represent hydrogen, and $R^{34}$ and $R^{37}$ are as defined above,
characterized in that
a compound of the general formula (I")

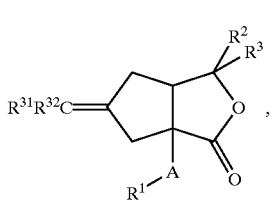
(I")

in which

A, $R^1$, $R^2$ $R^3$, $R^{31}$ and $R^{32}$ are as defined above, is isomerized in the presence of a catalyst and, if appropriate, a solvent.

The process according to the invention can be illustrated in an exemplary manner by the formula scheme below:

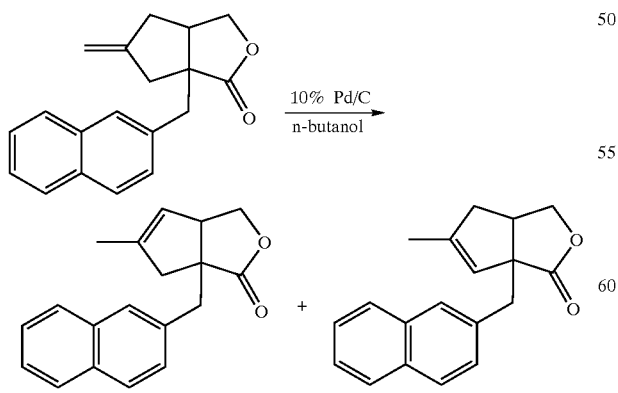

Suitable solvents are, for example, alcohols.
Preference is given to n-butanol.

Suitable catalysts are transition metals, such as, for example, palladium, platinum or rhodium, preferably palladium, in an amount of from 0.01 to 1 equivalent, based on the amount of the compound of the general formula (I") used, preferably from 0.05 to 0.2 equivalents.

Very particular preference is given to palladium adsorbed on activated carbon.

The reaction is generally carried out in a temperature range from 80 to 200° C., preferably from 100 to 150° C.

The reaction can be carried out under atmospheric, elevated or under reduced pressure (for example from 0.5 to 5 bar). In general, the reaction is carried out under atmospheric pressure.

Moreover, the present invention relates to compounds of the general formula (II)

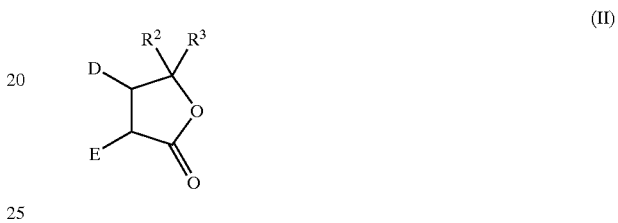
(II)

in which $R^2$ and $R^3$ are identical or different and represent hydrogen or $(C_1$–$C_6)$-alkyl,
and
D and E together form radicals of the formulae

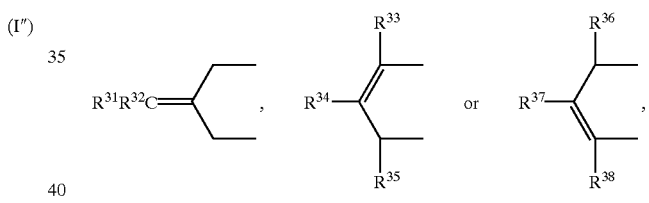

in which $R^{31}$, $R^{32}$, $R^{33}$, $R^{34}$, $R^{35}$, $R^{36}$, $R^{37}$ and $R^{38}$ are identical or different and represent hydrogen, phenyl or $(C_1$–$C_6)$-alkyl.

Preference is given to compounds of the general formula (II), in which $R^2$ and $R^3$ represent hydrogen or methyl,
and
D and E together form radicals of the formulae

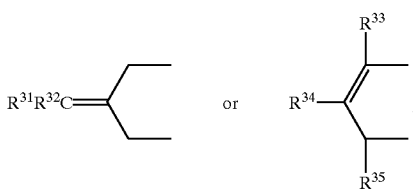

in which $R^{31}$, $R^{32}$, $R^{33}$, $R^{34}$ and $R^{35}$ represent hydrogen.

Moreover, we have found processes for preparing the compounds of the general formula (II) according to the invention

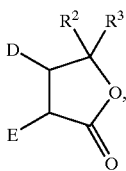 (II)

in which
D, E, $R^2$ and $R^3$ are as defined above,
characterized in that in
[A] compounds of the general formula (IV)

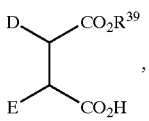 (IV)

in which
D and E are as defined above
and
$R^{39}$ represents $(C_1-C_4)$-alkyl or $(C_2-C_4)$-alkenyl, which are optionally substituted by phenyl,
the ester group is selectively reduced and the reaction product is cyclized under acidic conditions, if appropriate after prior activation of the carboxyl group to give the lactone,
or
[B] compounds of the general formula (V)

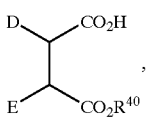 (V)

in which
D and E are as defined above
and
$R^{40}$ represents $(C_1-C_4)$-alkyl or $(C_3-C_4)$-alkenyl, which may optionally be substituted by phenyl,
the carboxyl group is selectively reduced and the reaction product is cyclized to give the lactone,
or
[C] compounds of the general formula (VI)

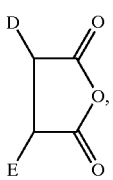 (VI)

in which
D and E are as defined above,
are initially reduced under suitable reduction conditions to give a hydroxylactone and subsequently reacted in an inert solvent with a compound of the general formula (VII), $R^{2'}$—Q (VII), in which
$R^{2'}$ represents $(C_1-C_6)$-alkyl, and
Q represents an alkali metal halide or alkaline earth metal halide, preferably Mg-X,
and cyclized under acidic conditions to give the corresponding lactone,
or
[D] compounds of the general formula (VI) are reacted in an inert solvent with at least two molar equivalents of a compound of the general formula (VII) and cyclized under acidic conditions to give the corresponding lactone,
or
[E] compounds of the general formula (VI) are, in an inert solvent, initially reacted with a molar equivalent of a compound of the general formula (VII), and then reacted with at least one further molar equivalent of a compound of the general formula (VIII)

$R^{3'}$—Q' (VIII), in which
$R^{3'}$ represents $(C_1-C_6)$-alkyl and
Q' has the abovementioned meaning of Q and is identical to or different from this,
and cyclized under acidic conditions to give the corresponding lactone.

The processes according to the invention can be illustrated in an exemplary manner by the formula schemes below:

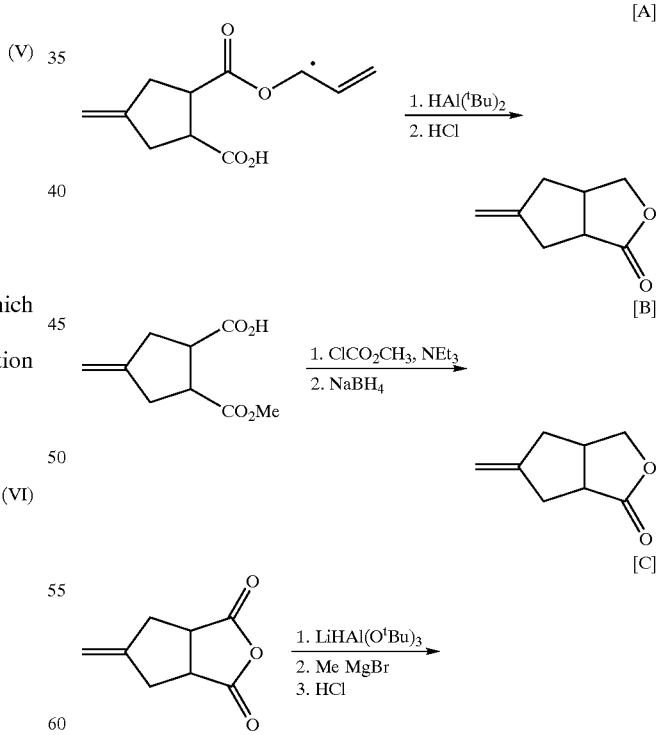

-continued

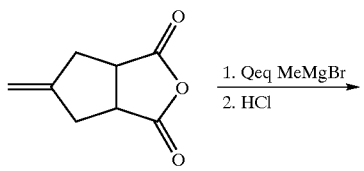

[D]

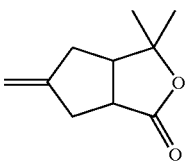

Suitable reducing agents for the process [A] are complex metal hydrides.

Preference is given to diisobutylaluminium hydride.

Suitable solvents are inert solvents, such as, for example, methylene chloride, THF, dioxane, diethyl ether, toluene, 1,2-dichloroethane.

Preference is given to methylene chloride.

The reaction is generally carried out in a temperature range of from −40° C. to the reflux temperature of the solvent, preferably from 0° C. to 30° C.

If appropriate, the cyclization of the hydroxycarboxylic acid intermediate can be supported by activating the carboxyl group, for example using alkyl chloroformates, preferably methyl chloroformate, in the presence of a base, such as, for example, triethylamine.

A suitable method of reduction for the process [B] is a stepwise reduction by pre-activating the carboxyl group using alkyl chloroformates, preferably methyl chloroformate, in the presence of a base, such as, for example, triethylamine, followed by reduction with a complex metal hydride, such as, for example, a borohydride, preferably sodium borohydride.

Suitable solvents for the activation are inert solvents, such as diethyl ether, THF, methylene chloride. Suitable solvents for the reduction with borohydrides are, for example, alcohols, in particular methanol.

The reaction is generally carried out in a temperature range from −40° C. to 40° C., preferably from −20° C. to 30° C.

Suitable reducing agents for the process [C] are complex metal hydrides having reduced reactivity, such as, for example, lithium tris-tert-butoxyaluminohydride.

Solvents which are suitable for this purpose are inert solvents, such as, for example, diethyl ether or THF.

The reaction is generally carried out in a temperature range of from −78° C. to 0° C., preferably from −50° C. to −20° C.

Suitable inert solvents for the reaction with the compounds of the general formulae (VII) and (VIII) in processes [C] to [E] are ethers, preferably diethyl ether or THF.

The reactions are generally carried out in a temperature range of from −78° C. to 35° C., preferably at from −60° C. to 25° C.

Suitable acids for the cyclization to the lactones are, in particular, mineral acids, such as, for example, dilute aqueous sulphuric acid or hydrochloric acid.

The compounds of the general formulae (IV) and (V) are known per se or can be prepared by customary methods.

The compounds of the general formula (I) according to the invention are suitable for use as medicaments in the treatment of humans and animals.

The compounds of the general formula (I) according to the invention are suitable for modulating metabotropic glutamate receptors and therefore influence the glutamatergic neurotransmitter system.

For the purpose of the invention, a modulator of the metabotropic glutamate receptor is an agonist or antagonist of this receptor.

The compounds according to the invention are particularly suitable as modulators of the metabotropic glutamate receptor of subtype 1, very particularly as antagonists of this receptor subtype.

Owing to their pharmacological properties, the compounds according to the invention can be used, on their own or in combination with other pharmaceuticals, for the treatment and/or prevention of neuronal damage or disorders associated with pathophysiological conditions of the glutamatergic system in the central and peripheral nervous system.

For the treatment and/or prevention of neuronal damage caused, for example, by ischaemic, thromb- and/or thrombembolic and haemorrhagic stroke, conditions after direct and indirect injuries in the area of the brain and the skull. Furthermore for the treatment and/or prevention of cerebral ischaemias after surgical interventions in the brain or peripheral organs or body parts and conditions of pathological or allergic nature accompanying or preceding them, which can lead primarily and/or secondarily to neuronal damage.

Likewise, the compounds according to the invention are also suitable for the therapy of primary and/or secondary pathological conditions of the brain, for example during or after cerebral vasospasms, hypoxia and/or anoxia of previously unmentioned origin, perinatal asphyxia, autoimmune disorders, metabolic and organ disorders which can be accompanied by damage to the brain, and also damage to the brain as a result of primary brain disorders, for example convulsive conditions and artero- and/or arteriosclerotic changes. For the treatment of chronic or psychiatric conditions such as, for example, depression, neurodegenerative disorders, such as, for example, Alzheimer's, Parkinson's or Huntington's disease, multiple sclerosis, amyotrophic lateral sclerosis, neurodegeneration due to acute and/or chronic viral or bacterial infections and multiinfarct dementia.

Moreover, they can be used as pharmaceuticals for the treatment of dementias of different origin, impaired brain performance owing to old age, memory disturbances, spinal injuries, states of pain, states of anxiety of different origin, medicament-related Parkinson's syndrome, psychoses (such as, for example, schizophrenia), brain oedema, neuronal damage after hypoglycaemia, emesis, nausea, obesity, addiction and withdrawal symptoms, CNS-mediated spasms, sedation and motor disturbances.

Furthermore, the compounds of the general formula (I) according to the invention can be used for promoting neuronal regeneration in the post-acute phase of cerebral injuries or chronic disorders of the nervous system.

They are preferably employed as pharmaceuticals for the treatment of cerebral ischaemias, craniocerebral trauma, states of pain or CNS-mediated spasms (such as, for example, epilepsy).

The modulation of substances at the metabotropic glutamate receptor (direct or indirect effect on the coupling efficiency of the glutamate receptor to G-proteins) can be examined using primary cultures of granular cells from the cerebellum. Electrophysiological measurements on these cell cultures in the "cell attached" mode show that L-type $Ca^{2+}$-channels in this preparation are activated by mGluR1-receptors (J. Neurosci. 1995, 15, 135), whereas they are blocked by group II receptors (J. Neurosci. 1994, 14, 7067–7076). By an appropriate experimental arrangement, it is possible to monitor the modulatory effect of pharmacological test substances on glutamate receptors. Detailed examination of subtype specificity under controlled conditions can be carried out by injecting the appropriate mGluR subtype DNA into Xenopus oocytes (WO 92/10583).

Permanent Focal Cerebral Ischaemia in the Rat (MCA-O)

Under isoflurane anaesthesia, the middle cerebral artery is exposed on one side and the latter and its side branches are irreversibly sealed by means of electrocoagulation. As a result of the intervention a cerebral infarct is formed. During the operation, the body temperature of the animal is kept at 37° C. After wound closure and wearing off of the anaesthesia, the animals are again released into their cage. Substance administration is carried out according to different time schemes and via different administration routes (i.v., i.p.) after occlusion. The infarct size is determined after 7 days. To do this, the brain is removed, worked up histologically and the infarct volume is determined with the aid of a computer-assisted analysis system.

Effectiveness in the model of permanent focal cerebral ischaemia (MCA-O)

| Example | % reduction of infarct volume | Dose[a] |
|---------|-------------------------------|---------|
| 35 | 38 | 0.01 mg/kg/h |

[a] Substance administered as intravenous continuous infusion directly up to 4 hours after the occlusion Subdural Haematoma in the Rat (SDH)

Under anaesthesia, the animal's own blood is injected subdurally on one side. An infarct is formed under the haematoma. Substance administration is earned out according to different time schemes and via different administration routes (i.v., i.p.).

The determination of the infarct size is carried out as described in the model of permanent focal ischaemia in the rat (MCA-O).

Effectiveness in the model "Subdural haematoma in the rat (SDH)"

| Example | % reduction of infarct volume | Dose[a] |
|---------|-------------------------------|---------|
| 35 | 51 | 0.01 mg/kg/h |

[a] Substance administered as intravenous continuous infusion directly up to 4 hours post-trauma Using the method described in NeuroReport 1996, 7, 1469–1474, it is possible to test for antiepileptic activity.

The suitability of the compounds according to the invention for treating schizophrenia can be determined by the methods described in Science 1998, 281, 1349–1352 and Eur. J. Pharmacol. 1996, 316, 129–136.

The present invention also includes pharmaceutical preparations which, in addition to inert, non-toxic, pharmaceutically suitable auxiliaries and excipients, comprise one or more compounds of the general formula (I), or which consist of one or more active compounds of the formula (I), and processes for producing these preparations.

In these preparations, the active compounds of the formula (I) should be present in a concentration of from 0.1 to 99.5% by weight, preferably from 0.5 to 95% by weight, of the total mixture.

In addition to the active compounds of the formula (I), the pharmaceutical preparations may also comprise other pharmaceutical active compounds.

The abovementioned pharmaceutical preparations can be prepared in a customary manner by known methods, for example with the auxiliary(ies) or excipient(s).

In general, it has proved advantageous to administer the active compound(s) of the formula (I) in total amounts of about 0.01 to about 100 mg/kg, preferably in total amounts of about 1 mg/kg to 50 mg/kg, of body weight per 24 hours, if appropriate in the form of a plurality of individual administrations, to achieve the desired result.

However, if appropriate, it may be advantageous to depart from the amounts mentioned, namely depending on the type and on the body weight of the object treated, on the individual response towards the medicament, the nature and severity of the disorder, the manner of formulation and administration, and the time or interval at which administration takes place.

General Section

| Mobile phases for chromatography | |
|---|---|
| I | Dichloromethane/methanol |
| II | Dichloromethane/ethanol |
| III | Cyclohexane/ethyl acetate |
| IV | Cyclohexane/dichloromethane |
| V | Butyl acetate:butanol:acetic acid:phosphate buffer (pH = 6) 200:26:100:60 |
| Abbreviations | |
| DME | 1,2-dimethoxyethane |
| HMPA | Hexamethylphosphone triamide |
| LiHMDS | Lithium bistrimethylsilylamide |
| LDA | Lithium diisopropylamide |
| MTBE | Methyl tert-butyl ether |
| THF | Tetrahydrofuran |
| MPLC | Medium pressure liquid chromatography |

Starting Materials

EXAMPLE 1A (3aS*,6aR*)-5-Methylidene-hexahydro-cyclopenta[c]furan-1-one

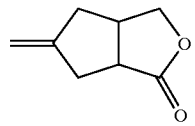

At −15° C., a solution of 2-methoxycarbonyl-4-methylidenecyclopentanecarboxylic acid (189.2 g; 1.027 mol) in THF (1 l) was admixed with triethylamine (156.6 ml; 1.130 mol) and ethyl chloroformate (18.2 ml; 1.027 mol), and the reaction mixture was stirred at room temperature for 1 h. The precipitate was filtered off with suction and the filtrate was concentrated, taken up in methanol (1 l), NaBH$_4$ (97.146 g; 2.568 mol) was added a little at a time at −15° C. and the mixture was stirred at room temperature for 1 h. For work-up, the mixture was admixed with 1 N HCl, saturated with NaCl and extracted with ethyl acetate. The combined organic phases were dried (Na$_2$SO$_4$) and concentrated, and the crude product was purified by chromatography.

Yield: 82.03 g (58%)

$R_f$ (II, 50:1)=0.42

MS (EI): m/e=138 [M$^+$]

EXAMPLE 2A (−)-(3aS,6aR)-5-Methylidene-hexahydro-cyclopenta[c]furan-1-one

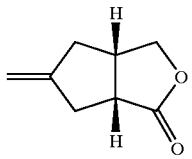

Analogously to the procedure of Example 1A, the target compound was prepared from (1R,2S)-4-methylidene-2-(3-phenyl-2-propenyloxycarbonyl)-cyclopentane-carboxylic acid (31.5 g; 110.2 mmol; 97% ee; Example 1 in EP 805 145A1, p. 9).

Yield: 7.97 g (52%; 97% ee)

$R_f$ (I, 80:1)=0.56

EXAMPLE 3A (+)-(3aR, 6aS)-5-Methylidene-hexahydro-cyclopentan[c]furan-1-one

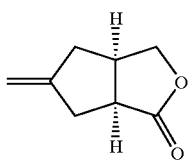

At 10° C., a solution of diisobutylaluminium hydride (1.5 M in $CH_2Cl_2$; 17.7 ml; 26.58 mmol) was added dropwise to a solution of (1S,2R)-4-methylidene-2-allyloxy-carbonyl-cyclopentane-carboxylic acid (2.0 g; 9.61 mmol; 75% ee; Example 5 in DOS (German Published Specification) 44 00 749, p. 11+12) in dichloromethane (50 ml), and the mixture was stirred at room temperature for 1 h. The mixture was admixed with 1 N HCl and water and extracted with ethyl acetate. The combined organic phases were dried ($Na_2SO_4$), the solvent was removed under reduced pressure and the residue was taken up in THF (200 ml). At 0° C., triethylamine (6.59 ml; 47.57 mmol) and ethyl chloroformate (2.27 ml; 23.78 mmol) were added and the reaction mixture was allowed to stand at 8° C. for 14 h The mixture was then admixed with ethyl acetate and water. The organic phase was washed with 10% aqueous HCl, saturated NaCl solution, 10% aqueous $NaHCO_3$ solution and saturated NaCl solution, dried ($MgSO_4$) and concentrated, and the residue was purified by MPLC.

Yield: 260 mg (20%, 89% ee)

$R_f$ (I, 10:1)=0.88

EXAMPLE 4A (3S*,3aR*,6aS*)-3-Methyl-5-methylidene-hexahydro-cyclopenta[c]furan-1-one

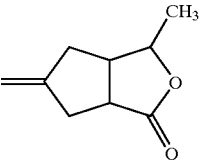

At −40° C., a solution of 4-exomethylene-1,2-cyclopentanedicarboxylic anhydride (10.0 g, 65.7 mmol; ref. DE 4400749) in THF (130 ml) was added to a solution of lithium tri-tert-butoxyaluminohydride (1M in THF, 82.16 ml), and the reaction mixture was stirred at −30° C. for 14 h. For work-up, the mixture was admixed with 1 N HCl, the THF was removed under reduced pressure and the aqueous phase was saturated with NaCl and extracted with dichloromethane. The combined organic phases were dried ($MgSO_4$), the solvent was removed under reduced pressure and the residue was purified by MPLC. Yield: 2.24 g.

The resulting intermediate (1 g; 6.47 mmol) in diethyl ether (15 ml) was, at 0° C., added to a solution of methylmagnesium bromide (3M in diethyl ether, 4.3 ml, 12.0 mmol), and the reaction mixture was stirred at room temperature for 2 h. The mixture was admixed with 10% aqueous HCl, stirred at room temperature and extracted with ethyl acetate, the combined organic phases were dried ($Na_2SO_4$), the solvents were removed under reduced pressure and the crude product was purified by MPLC.

Yield: 412 mg (33%)

$R_f$ ($CH_2Cl_2$)=0.69

MS ($DCI/NH_3$): m/e=170 [$M+N_4^+$]

EXAMPLE 5A (3aS*,6aR*)-3,3-Dimethyl-5-methylidene-hexahydro-cyclopenta[c]furan-1-one

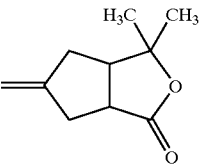

At 0° C., a solution of 4-exomethylene-1,2-cyclopentanedicarboxylic anhydride (1.0 g; 6.5 mmol) in diethyl ether (40 ml) was added to a solution of methylmagnesium bromide (3 M in diethyl ether, 6.6 ml; 19.7 mmol), and the reaction mixture was stirred at room temperature for 14 h. The mixture was admixed with 10% aqueous HCl, saturated with sodium chloride and extracted with ethyl acetate, and the combined organic phases were washed with 10% aqueous $Na_2CO_3$ and saturated NaCl solution and dried ($Na_2SO_4$). Removal of the solvents under reduced pressure gives the title compound.

Yield: 929 mg (85%)

$R_f$ (I, 10:1)=0.24

MS (EI): m/e=166 [$M^+$]

PREPARATION EXAMPLES

EXAMPLE 1

(3aS*,6aS*)-6a-Benzyl-5-methylidene-hexahydro-cyclopenta[c]furan-1-one

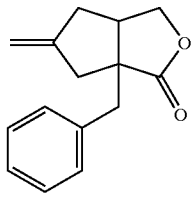

At −78° C., a solution of the compound from Example 1A (90 mg, 0.65 mmol) in toluene (3 ml) was added to a solution of LiHMDS (1M in THF, 0.65 ml, 0.65 mmol) diluted with toluene (7 ml). The mixture was allowed to warm to room temperature, stirred for a further 60 min and then admixed with the alkylating agent (benzyl bromide, 89.1 mg, 0.521 mmol). After 14 h at room temperature, water (1 ml) was added, the reaction mixture was filtered through a frit filled with bituminous earth/silica gel, the solvents were removed under reduced pressure and the crude product was, if appropriate, purified by MPLC;

Yield: 81 mg (68%)

$R_f$ (I, 80:1)=0.67

MS (EI): m/e=229 [M+H$^+$]

The Examples 2 to 97 listed in the table below were prepared analogously to the procedure of Example 1. The alkylating agents used were the corresponding halides, aldehydes or esters.

| Ex. No. | Structure | Starting Material Ex. No. | Yield [%] | Rf | MS |
|---|---|---|---|---|---|
| 2 | 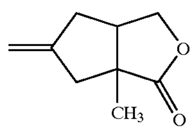 | 1A | 18 | 0.23 (III, 50:1) | 153 [M + H+] |
| 3 | 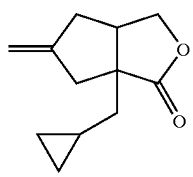 | 1A | 8 | 0.582 (I, 80:1) | 210 [M + NH4+] |
| 4 | 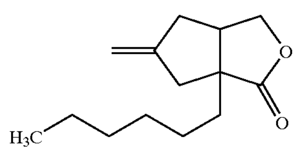 | 1A | 66 | 0.73 (I, 80:1) | 223 [M + H+] |
| 5 | Chiral | 2A | 65 | 0.45 (III, 5:1) | 229 [M + H+] |
| 6 | 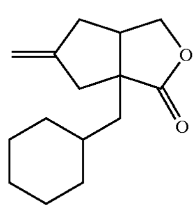 | 1A | 13 | 0.47 (III, 5:1) | 235 [M + H+] |

-continued

| Ex. No. | Structure | Starting Material Ex. No. | Yield [%] | Rf | MS |
|---|---|---|---|---|---|
| 7 | 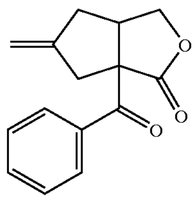 | 1A | 6 | 0.63 (CH2Cl2) | 260 [M + NH4+] |
| 8 | 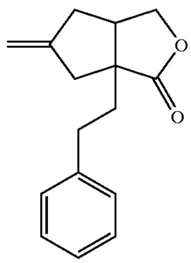 | 1A | 2 | 0.16 (III, 5:1) | 265 [M + Na+] |
| 9 | 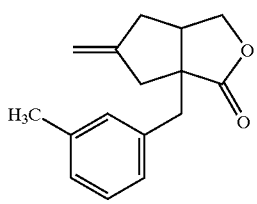 | 1A | 90 | 0.44 (III, 5:1) | 284 [M + CH3CN + H+] |
| 10 | 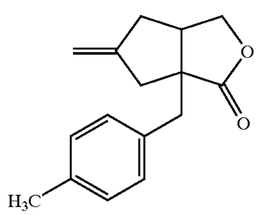 | 1A | 79 | 0.44 (III, 5:1) | 284 [M + CH3CN + H+] |
| 11 | 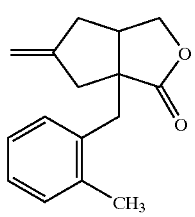 | 1A | 18 | 0.42 (III, 5:1) | 284 [M + CH3CN + H+] |
| 12 | 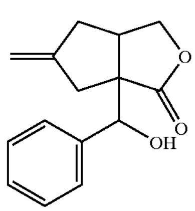 | 1A | 7 | 0.27 (CH2Cl2) | 265 [M + Na+] |
| 13 | 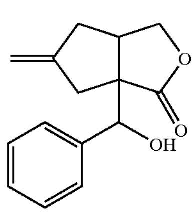 | 1A | 33 | 0.15 (CH2Cl2) | 262 [M + NH4+] |

-continued

| Ex. No. | Structure | Starting Material Ex. No. | Yield [%] | Rf | MS |
|---|---|---|---|---|---|
| 14 | 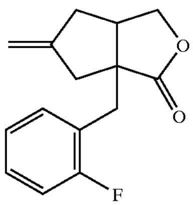 | 1A | 96 | 0.32 (III, 5:1) | 288 [M + CH3CN + H+] |
| 15 | 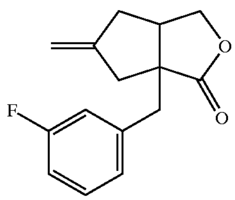 | 1A | 96 | 0.31 (III, 5:1) | 288 [M + CH3CN + H+] |
| 16 | 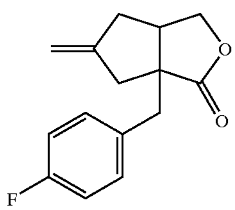 | 1A | 98 | 0.31 (III, 5:1) | 288 [M + CH3CN + H+] |
| 17 | 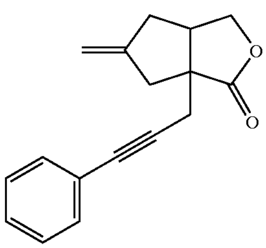 | 1A | 11 | 0.20 (III, 5:1) | 361 [M + H+] |
| 18 | 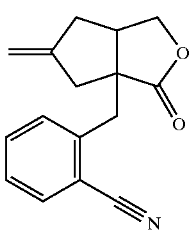 | 1A | 47 | 0.20 (III, 5:1) | 295 [M + CH3CN + H+] |
| 19 | 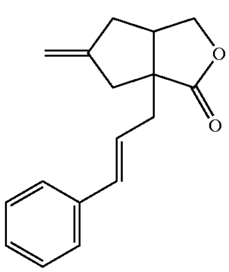 | 1A | 53 | 0.29 (III, 5:1) | 296 [M + CH3CN + H+] |

-continued

| Ex. No. | Structure | Starting Material Ex. No. | Yield [%] | Rf | MS |
|---|---|---|---|---|---|
| 20 | 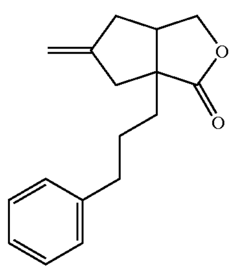 | 1A | 70 | 0.62 (I, 80:1) | 349 [M + H+] |
| 21 | 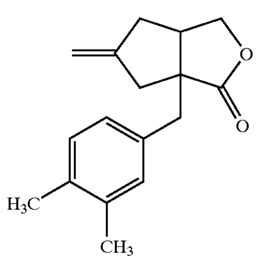 | 1A | 34 | 0.42 (III, 5:1) | 274 [M + NH4+] |
| 22 | 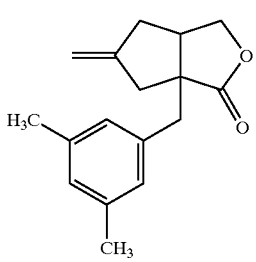 | 1A | 71 | 0.44 (III, 5:1) | 298 [M + CH3CN + H+] |
| 23 | 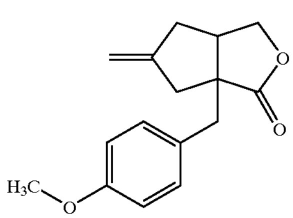 | 1A | 9 | 0.15 (III, 10:1) | 281 [M + Na+] |
| 24 | 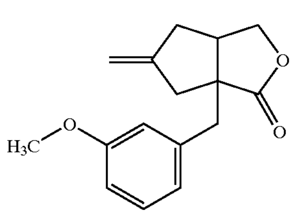 | 1A | 38 | 0.30 (III, 5:1) | 300 [M + CH3CN + H+] |
| 25 | 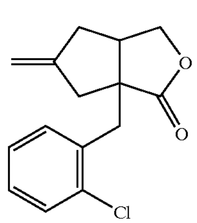 | 1A | 100 | 0.42 (III, 5:1) | 304 [M + CH3CN + H+] |

-continued

| Ex. No. | Structure | Starting Material Ex. No. | Yield [%] | Rf | MS |
|---|---|---|---|---|---|
| 26 | 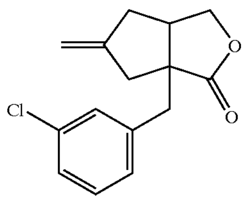 | 1A | 96 | 0.34 (III, 5:1) | 304 [M + CH3CN + H+] |
| 27 | 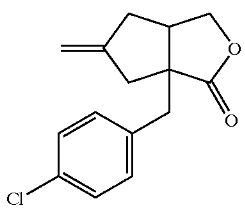 | 1A | 20 | 0.32 (III, 5:1) | 304 [M + CH3CN + H+] |
| 28 | 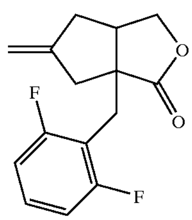 | 1A | 99 | 0.34 (III, 5:1) | 306 [M + CH3CN + H+] |
| 29 | 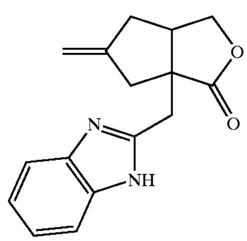 | 1A | 2 | 0.42 (III, 5:1) | 310 [M + CH3CN + H+] |
| 30 | 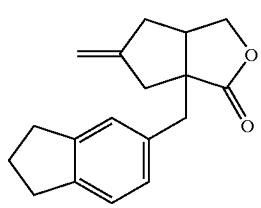 | 1A | 21 | 0.35 (III, 10:1) | 284 [M + NH4+] |
| 31 | 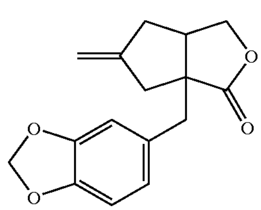 | 1A | 58 | 0.242 (III, 50:1) | 272 [M+] |

-continued

| Ex. No. | Structure | Starting Material Ex. No. | Yield [%] | Rf | MS |
|---|---|---|---|---|---|
| 32 | 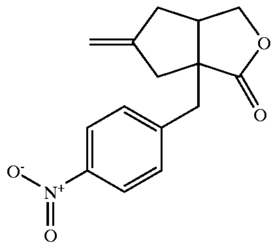 | 1A | 14 | 0.05 (IV, 1:1) | 291 [M + Na+] |
| 33 | 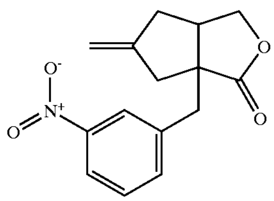 | 1A | 2 | 0.42 (III, 5:1) | 291 [M + NH4+] |
| 34 | 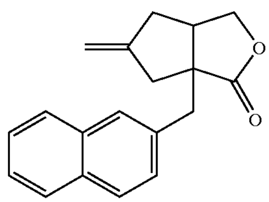 | 1A | 45 | 0.34 (III, 5:1) | 296 [M + NH4+] |
| 35 | 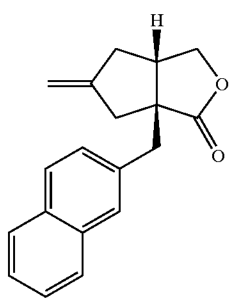 | 2A | 42 | 0.60 (CH2Cl2) | 296 [M + NH4+] |
| 36 | 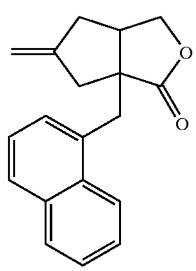 | 1A | 5 | 0.24 (III, 5:1) | 301 [M + Na+] |
| 37 | 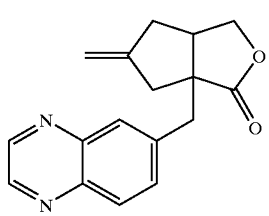 | 1A | 1 | 0.58 (III, 1:1) | 281 [M + H+] |

-continued

| Ex. No. | Structure | Starting Material Ex. No. | Yield [%] | Rf | MS |
|---|---|---|---|---|---|
| 38 | 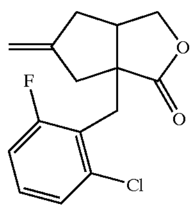 | 1A | 99 | 0.36 (III, 5:1) | 322 [M + CH3CN + H+] |
| 39 | 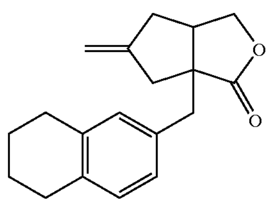 | 1A | 15 | 0.35 (III, 10:1) | 300 [M + NH4+] |
| 40 | 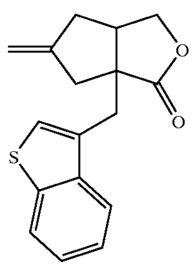 | 1A | 5 | 0.192 (III, 10:1) | 326 [M + CH3CN + H+] |
| 41 | 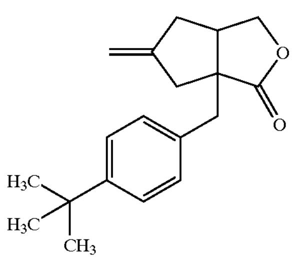 | 1A | 28 | 0.46 (III, 5:1) | 302 [M + NH4+] |
| 42 | 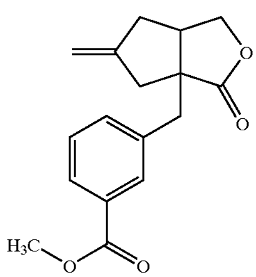 | 1A | 59 | 0.66 (I, 80:1) | 309 [M + Na+] |
| 43 | 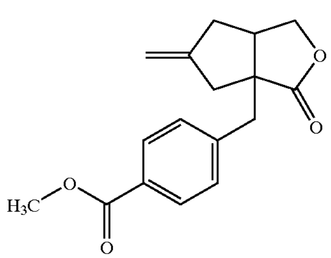 | 1A | 41 | 0.12 (III, 5:1) | 328 [M + CH3CN + H+] |

-continued

| Ex. No. | Structure | Starting Material Ex. No. | Yield [%] | Rf | MS |
|---|---|---|---|---|---|
| 44 | 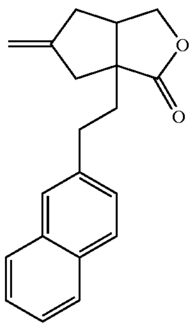 | 1A | 3 | 0.42 (III, 4:1) | 310 [M + NH4+] |
| 45 | 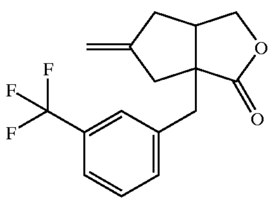 | 1A | 84 | 0.31 (III, 5:1) | 338 [M + CH3CN + H+] |
| 46 | 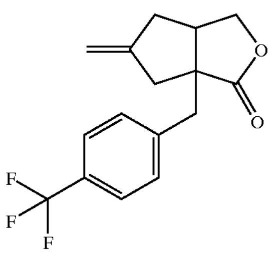 | 1A | 80 | 0.31 (III, 5:1) | 338 [M + CH3CN + H+] |
| 47 | 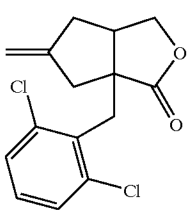 | 1A | 75 | 0.42 (III, 5:1) | 338 [M + CH3CN + H+] |
| 48 | 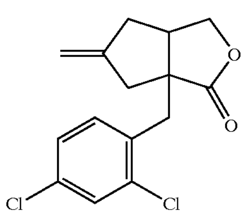 | 1A | 44 | 0.44 (III, 5:1) | — |
| 49 | 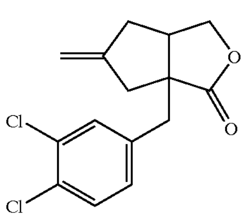 | 1A | 12 | 0.24 (III, 10:1) | 314 [M + NH4+] |

-continued
| Ex. No. | Structure | Starting Material Ex. No. | Yield [%] | Rf | MS |
|---|---|---|---|---|---|
| 50 | 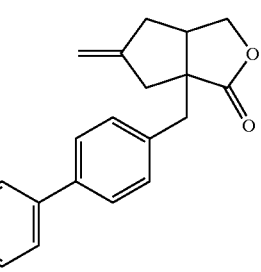 | 1A | 25 | 0.82 (I, 80:1) | 327 [M + Na+] |
| 51 | 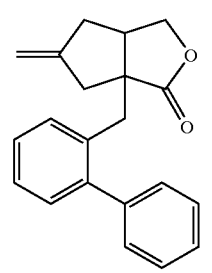 | 1A | 53 | 0.21 (III, 40:1) | 305 [M + H+] |
| 52 | 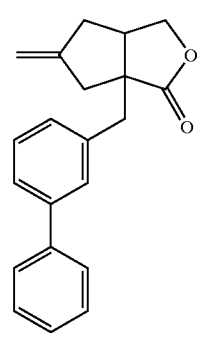 | 1A | 53 | 0.44 (III, 5:1) | 305 [M + H+] |
| 53 | 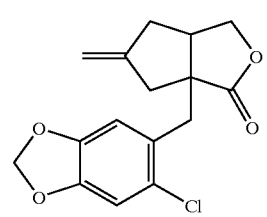 | 1A | 3 | 0.42 (III, 5:1) | 348 [M + CH3CN + H+] |
| 54 | 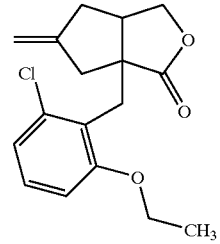 | 1A | 24 | 0.42 (III, 5:1) | 307 [M + H+] |

-continued

| Ex. No. | Structure | Starting Material Ex. No. | Yield [%] | Rf | MS |
|---|---|---|---|---|---|
| 55 | 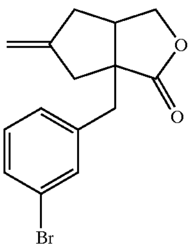 | 1A | 31 | 0.19 (III, 10:1) | 307/309 [M + H+] |
| 56 | 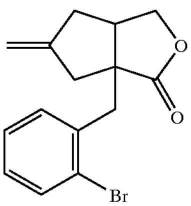 | 1A | 96 | 0.42 (III, 5:1) | 348 [M + CH3CN + H+] |
| 57 | Chiral | 2A | 67 | 0.45 (III, 5:1) | 307/309 [M + H+] |
| 58 | 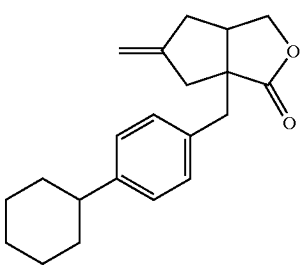 | 1A | 9 | 0.42 (III, 5:1) | 352 [M + CH3CN + H+] |
| 59 | 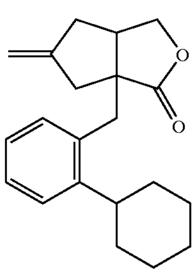 | 1A | 3 | 0.42 (III, 5:1) | 352 [M + CH3CN + H+] |

-continued

| Ex. No. | Structure | Starting Material Ex. No. | Yield [%] | Rf | MS |
|---|---|---|---|---|---|
| 60 | 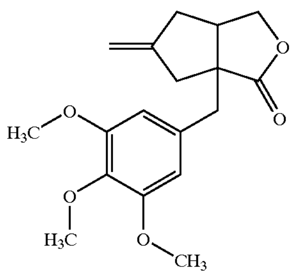 | 1A | 49 | 0.32 (III, 2:1) | 336 [M + H+] |
| 61 | 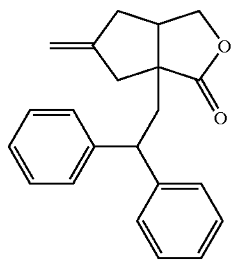 | 1A | 15 | 0.78 (I, 80:1) | — |
| 62 | 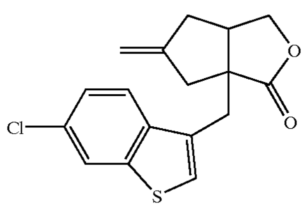 | 1A | 17 | 0.42 (III, 5:1) | 336 [M + NH4+] |
| 63 | 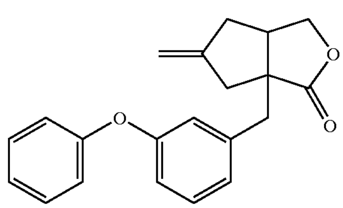 | 1A | 50 | 0.41 (III, 5:1) | 338 [M + NH4+] |
| 64 | (Chiral) | 2A | 52 | 0.45 (III, 5:1) | 321 [M + H+] |
| 65 | 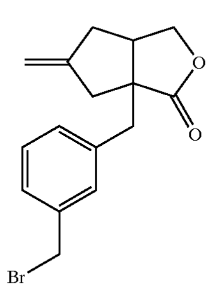 | 1A | 46 | 0.61 (CH2Cl2) | 323/321 [M + H+] |

-continued

| Ex. No. | Structure | Starting Material Ex. No. | Yield [%] | Rf | MS |
|---|---|---|---|---|---|
| 66 | 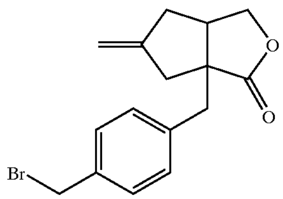 | 1A | 37 | 0.16 (III, 10:1) | 338 [M + NH4+] |
| 67 | 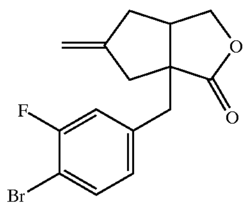 | 1A | 26 | 0.42 (III, 5:1) | 340/342 [M + NH4+] |
| 68 | 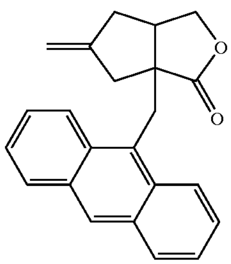 | 1A | 39 | 0.27 (III, 5:1) | 370 [M + CH3CN + H+] |
| 69 | 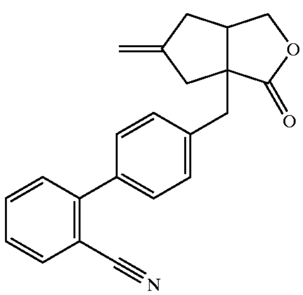 | 1A | 35 | 0.42 (III, 5:1) | — |
| 70 | 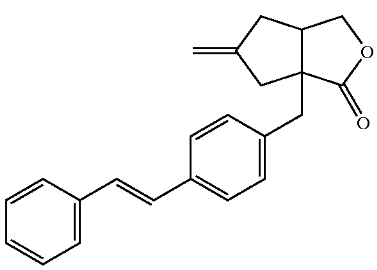 | 1A | 3 | 0.42 (III, 5:1) | 372 [M + CH3CN + H+] |
| 71 | 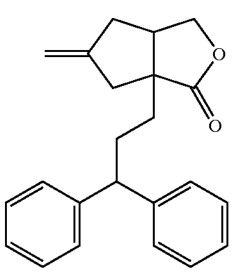 | 1A | 51 | 0.22 (IV, 1:1) | 355 [M + Na+] |

-continued

| Ex. No. | Structure | Starting Material Ex. No. | Yield [%] | Rf | MS |
|---|---|---|---|---|---|
| 72 | 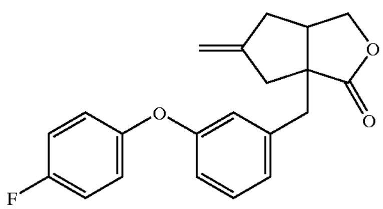 | 1A | 33 | 0.42 (III, 5:1) | 380 [M + CH3CN + H+] |
| 73 | 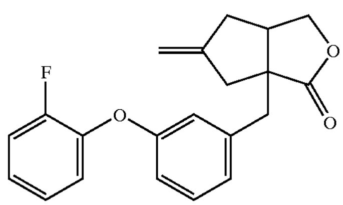 | 1A | 40 | 0.42 (III, 5:1) | 380 [M + CH3CN + H+] |
| 74 | 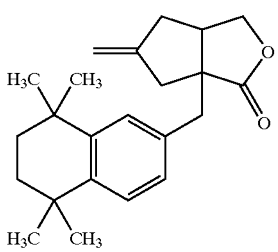 | 1A | 25 | 0.75 (III, 50:1) | 362 [M + H+] |
| 75 | 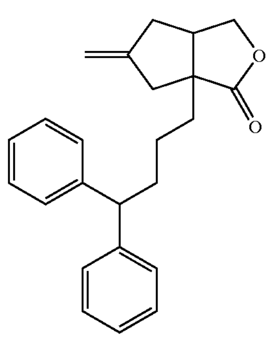 | 1A | 62 | 0.20 (IV, 5:1) | 347 [M + H+] |
| 76 | 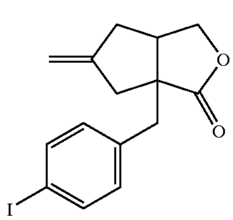 | 1A | 38 | 0.42 (III, 5:1) | 396 [M + CH3CN + H+] |
| 77 | 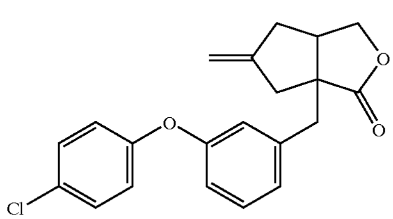 | 1A | 23 | 0.26 (III, 10:1) | 372 [M + NH4+] |

-continued
| Ex. No. | Structure | Starting Material Ex. No. | Yield [%] | Rf | MS |
|---|---|---|---|---|---|
| 78 | 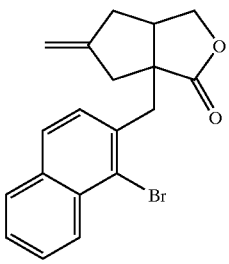 | 1A | 17 | 0.42 (III, 5:1) | 374/376 [M + NH4+] |
| 79 | 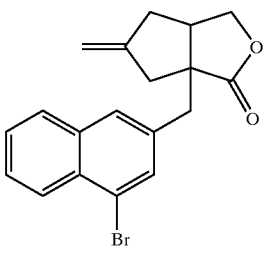 | 1A | 30 | 0.42 (III, 5:1) | 398 [M + CH3CN + H+] |
| 80 | 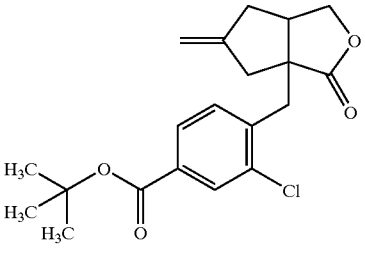 | 1A | 4 | 0.42 (III, 5:1) | 380 [M + NH4+] |
| 81 | 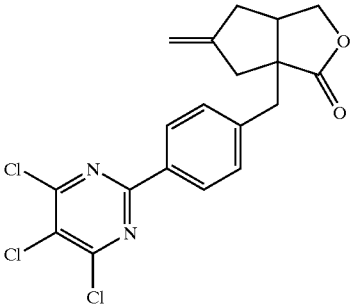 | 1A | 16 | 0.42 (III, 5:1) | 409 [M + H+] |
| 82 | 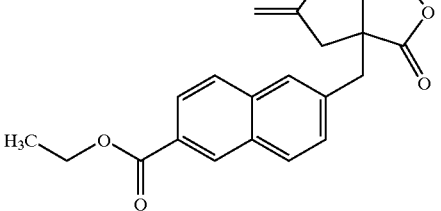 | 1A | 5 | 0.39 (III, 5:1) | 351 [M + H+] |

-continued
| Ex. No. | Structure | Starting Material Ex. No. | Yield [%] | Rf | MS |
|---|---|---|---|---|---|
| 83 | 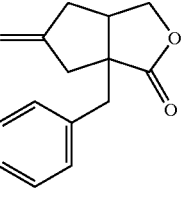 | 1A | 5 | 0.22 (III, 5:1) | 337 [M + H+] |
| 84 | 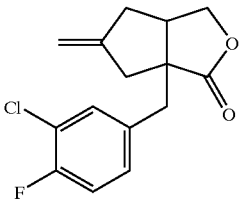 | 1A | 29 | 0.24 (III, 10:1) | 298 [M + NH4+] |
| 85 | 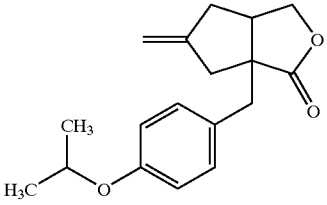 | 1A | 19 | 0.27 (III, 10:1) | 287 [M + H+] |
| 86 | 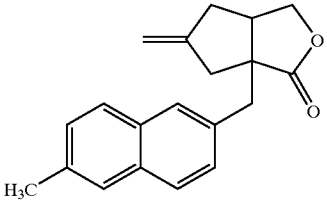 | 1A | 9 | 0.30 (III, 10:1) | 293 [M + H+] |
| 87 | 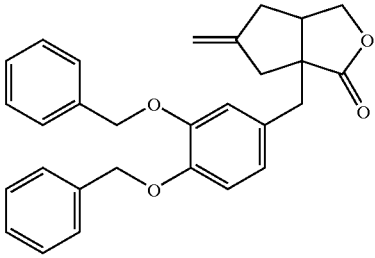 | 1A | 12 | 0.11 (III, 10:1) | 458 [M + NH4+] |
| 88 | 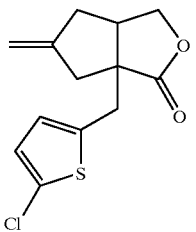 | 1A | 42 | 0.25 (III, 10:1) | 269 [M + H+] |

-continued

| Ex. No. | Structure | Starting Material Ex. No. | Yield [%] | Rf | MS |
|---|---|---|---|---|---|
| 89 | 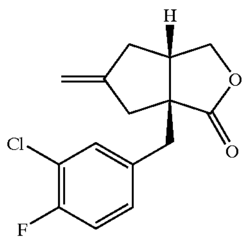 | 2A | 55 | 0.34 (III, 5:1) | — |
| 90 | 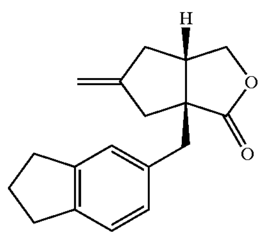 | 2A | 62 | 0.47 (III, 5:1) | 310 [M + H + H3CN+] |
| 91 | 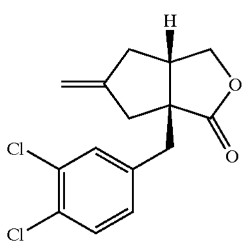 | 2A | 38 | 0.30 (III, 5:1) | — |
| 92 | 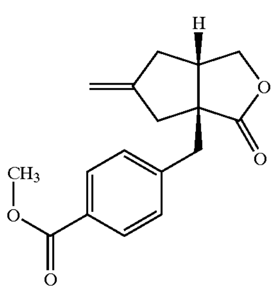 | 2A | 52 | 0.18 (III, 5:1) | 304 [M + NH4+] |
| 93 | Chiral | 2A | 74 | 0.34 (III, 5:1) | 314 [M + H3CCN + H+] |

-continued

| Ex. No. | Structure | Starting Material Ex. No. | Yield [%] | Rf | MS |
|---|---|---|---|---|---|
| 94 | Chiral | 2A | 66 | 0.36 (III, 5:1) | 326 [M + H3CCN + H+] |
| 95 | Chiral | 2A | 56 | 0 39 (III, 5:1) | 288 [M + H3CCN + H+] |
| 96 | 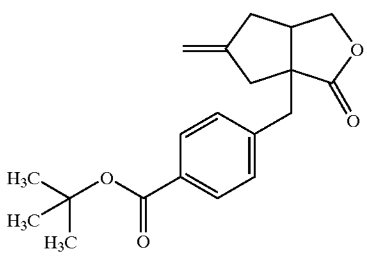 | 1A | 40 | 0.39 (III, 5:1) | 346 [M + NH4+] |
| 97 | 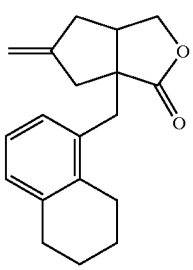 | 1A | 10 | 0.35 (III, 10:1) | 300 [M + NH4+] |

EXAMPLE 98

(3aS*,6aS*)-6a-(4-Allyloxycarbonylaminobenzyl)-5-methylene-hexahydro-cyclopenta[c]-furan-1-one

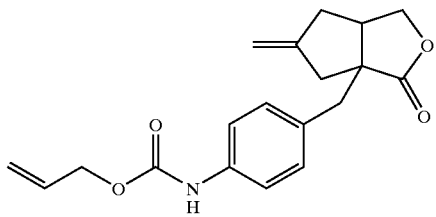

A mixture of the compound from Example 124 (2.02 g; 7.5 mmol), allyl alcohol (4.3 g, 74.29 mmol), diphenylphosphoryl azide (2.25 g, 8.17 mmol), diazabicyclo-octane (DABCO, 0.17 g; 1.5 mmol) and triethylamine (0.9 g, 8.92 mmol) in toluene (70 ml) was stirred under reflux for 48 h. The reaction mixture was admixed with 2 g of silica gel, the solvent was removed under reduced pressure and the residue was purified by MPLC.

Yield: 1.29 g (53%)

$R_f$ (III, 5:1)=0.23

MS (DCI): m/e=345 [M+NH$_4^+$]

The Examples 99 to 103 listed in the table below were prepared analogously to the procedure of Example 98:

| Ex. No. | Structure | Yield | $R_f$ | MS |
|---|---|---|---|---|
| 99 | 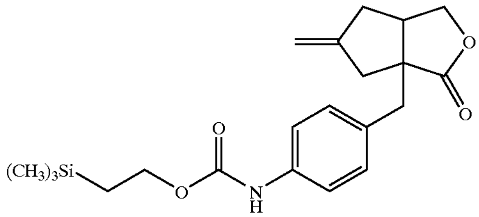 | 97 | 0.75 (III, 1:1) | / |
| 100 | 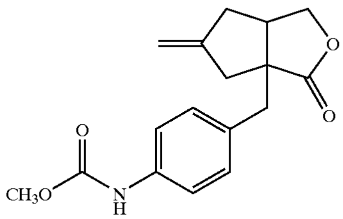 | 25 | 0.35 (III, 2:1) | / |
| 101 | 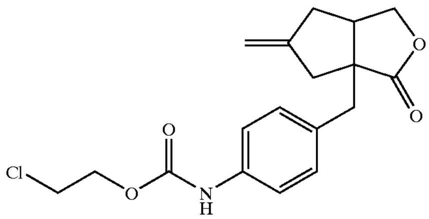 | 12 | 0.44 (III, 2:1) | / |
| 102 | 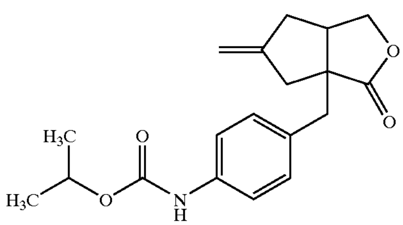 | 68 | 0.50 (III, 2:1) | / |
| 103 | 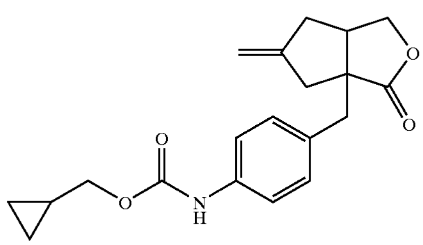 | 27 | 0.53 (III; 2:1) | / |

EXAMPLE 104

(3aS*,6aS*)-6a-(4-Aminobenzyl)-5-methylidene-hexahydro-cyclopenta[c]furan-1-one

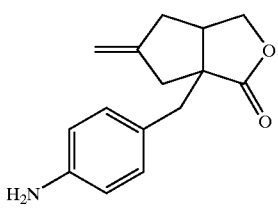

Example 98 (1.275 g; 3.96 mmol) was added to a solution of tris(dibenzylidene-acetone)dipalladium(0) (181 mg; 0.198 mmol), bis(diphenyl-phosphino)ethane (315 mg; 0.79 mmol) and dimedone (4.44 g; 31.65 mmol) in THF (320 ml) and the reaction mixture was heated under reflux for 1 hour. The reaction mixture is poured into 1 N HCl and the aqueous phase is washed with ethyl acetate (2×), then adjusted to pH=9–10 and extracted with ethyl acetate (3×). The combined extracts are washed with saturated NaCl solution and dried (MgSO₄) and the solvent is removed under reduced pressure.

Yield: 0.770 g (80%)

$R_f$ (III, 1:1)=0.42

The following compounds were prepared analogously:

| Ex. No. | Structure | Yield | $R_f$ |
|---|---|---|---|
| 105 | 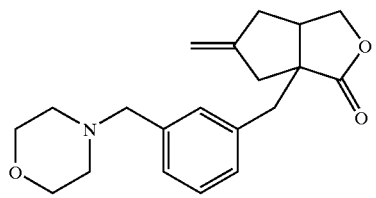 | 83 | 0.42 (II, 1:1) |

EXAMPLE 106

(3aS*,6aS*)-6a-(4-Acetylaminobenzyl)-5-methylidene-hexahydro-cyclopenta[c]furan-1-one

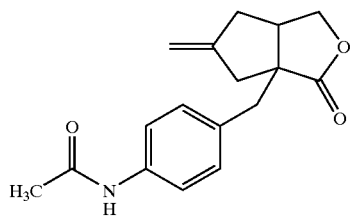

Triethylamine (12 μl, 0.080 mmol) and acetyl chloride (3.1 mg; 0.039 mmol) were added to a solution of the compound from Example 104 (10 mg; 0.036 mmol) in dichloromethane (5 ml), and the reaction mixture was stirred at room temperature for 20 h. For work-up, a saturated $NaHCO_3$ solution (1 ml) was added and the mixture was filtered through a frit filled with bituminous earth/silica gel and the product was eluted with dichloromethane/ethanol.

Yield: 12.2 mg (quant.)

$R_f$ (II, 50:1)=0.18

MS (ESI): m/e=286 [M+H⁺]

The following compounds were prepared analogously:

EXAMPLE 109

(3aS'"*,6a'"S*)-N-[3-(5-Methylidene-hexahydro-cyclopenta[c]furan-1-on-6a-yl-methyl)-phenyl]-morpholine A mixture of triethylamine (208 μl; 1.5 mmol), morpholine (131 μl; 1.5 mmol) and the compound from Example 65 (321 mg; 1.0 mmol) in dichloromethane (1 ml) were stirred at room temperature for 14 h. The mixture was concentrated and the crude product was purified by MPLC.

Yield: 230 mg (70%)

$R_f$ (I, 40:1)=0.25

MS (DCI/$NH_3$): m/e=328 [M+H⁺]

Examples 110 to 116 listed in the table below were prepared analogously to Example 109:

| Ex. No. | Structure | Yield | $R_f$ | MS |
|---|---|---|---|---|
| 107 | 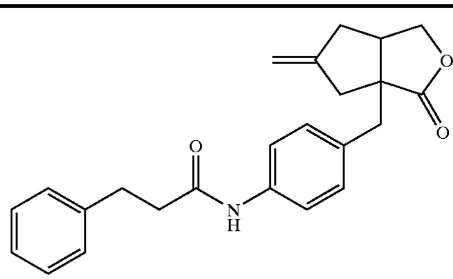 | quant. | 0.12 (II, 100:1) | 376 [M + H⁺] |
| 108 | 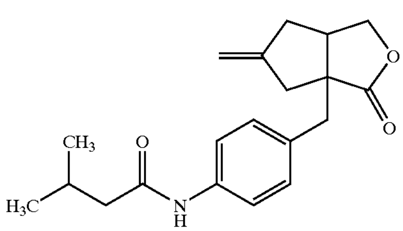 | quant. | 0.10 (II, 100:1) | 328 [M + H⁺] |

| Ex. No. | Structure | Starting material Ex. No. | Yield (%) | $R_f$ | MS |
|---|---|---|---|---|---|
| 110 | 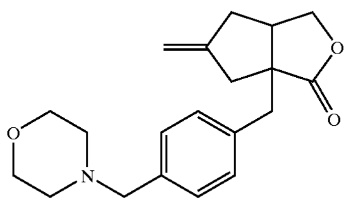 | 66 | 33 | 0.29 (I, 40:1) | 328 [M + H+] |
| 111 | 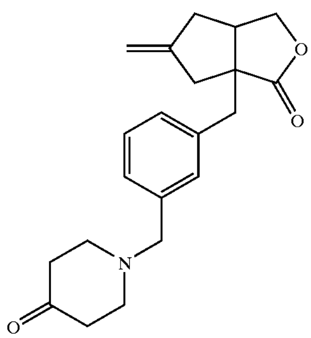 | 65 | 26 | 0.31 (I, 40:1) | 340 [M + H+] |
| 112 | 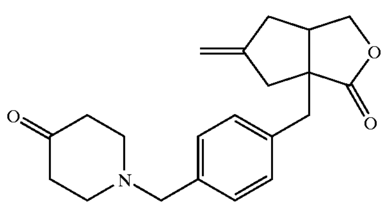 | 66 | 15 | 0.22 (I, 40:1) | 340 [M + H+] |
| 113 | 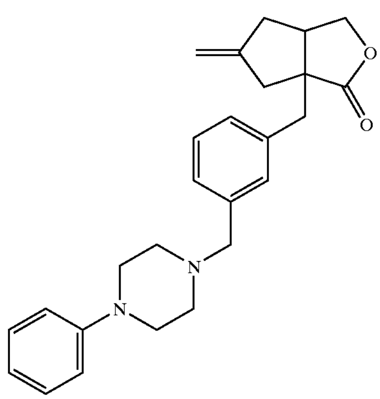 | 65 | 79 | 0.21 (I, 40:1) | 403 [M + H+] |
| 114 | 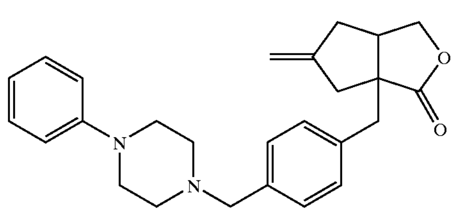 | 66 | 76 | 0.27 (I, 40:1) | 403 [M + H+] |

| Ex. No. | Structure | Starting material Ex. No. | Yield (%) | $R_f$ | MS |
|---|---|---|---|---|---|
| 115 | 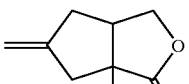 | 65 | 55 | 0.17 (I, 40:1) | 436 [M + H⁺] |
| 116 | 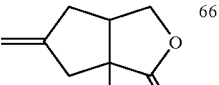 | 66 | 55 | 0.13 (I, 40:1) | 436 [M + H⁺] |

EXAMPLE 117 and Example 118

(3aS*,6aS*)-5-Methyl-6a-naphth-2-ylmethyl-3,3a,6,6a-tetrahydro-cyclopenta[c]-furan-1-one (Example 117) and (3aS*,6aS*)-5-methyl-6a-naphth-2-ylmethyl-3,3a,4,6a-tetrahydro-yclopenta[c]furan-1-one (Example 118)

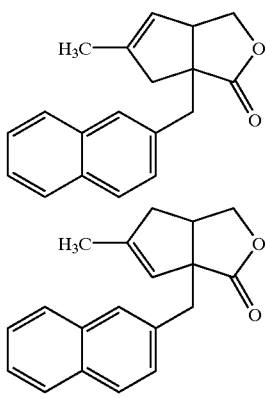

A mixture of the compound from Example 34 (370 mg, 1.33 mmol) and Pd-C (10%, 370 mg) in n-butanol (10 ml) was stirred under reflux for 48 h. Filtration, distillative removal of the solvent under reduced pressure and purification of the crude product by MPLC gave the title compound;

Yield: 155 mg (42%, Example 117)

$R_f$ (III, 5:1)=0.36

MS (EI): m/e=279 [M+H⁺]

Yield: 75 mg (21%, Example 118)

$R_f$ (III, 5:1)=0.30

MS (EI): m/e=301 [M+Na⁺]

EXAMPLE 119 and Example 120

(3aS*,3R*,6aS*)-3-Methyl-5-methylidene-6a-naphth-2-ylmethyl-hexahydro-cyclo-penta(c)furan-1-one and (3aS*,3S*,6aS*)-3-methyl-5-methylene-6a-naphth-2-yl-methyl-hexahydro-cyclopenta(c)furan-1-one

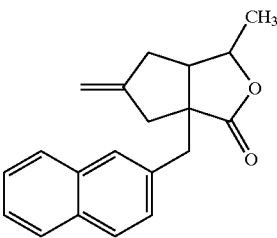

Analogously to the procedure of Example 1, the title compounds were prepared from the compound from Example 4A (200 mg, 1.314 mmol).

Yield: 309 mg (93%, mixture of the diastereomers)

$R_f$ (CH₂Cl₂)=0.53

MS (DCI)NH₃): m/e=310 [M+NH₄⁺]

The diastereomers were separated by HPLC (Kromasil 100 C 18, acetonitrile/water 1:1)

EXAMPLE 121

Diastereomer A, fraction 1

EXAMPLE 122

Diastereomer B, fraction 2

EXAMPLE 123

(3aS*,6aS*)-3,3-Dimethyl-5-methylidene-6a-naphth-2-ylmethyl-hexahydro-cyclopenta[c]furan-1-one

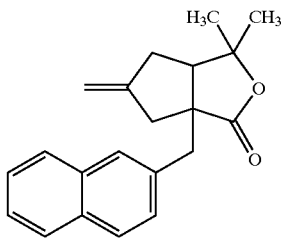

Analogously to the procedure of Example 1, the title compound was prepared from the compound from Example 5A (100 mg, 0.6 mmol);

Yield: 116 mg (63%)

$R_f$ (I, 10:1)=0.47

MS (ESI): m/e=307

EXAMPLE 124

(3a"S*,6"a)-4-(5-Methylidene-hexahydro-cyclopenta[c]furan-1-on-6a-ylmethyl)-benzoic acid

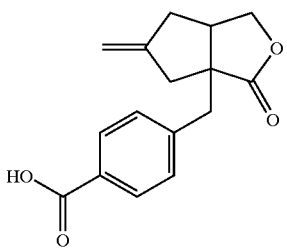

A solution of the compound from Example 43 (2.26 g, 7.89 mmol) in THF (100 ml) and aqueous NaOH (1 M, 127 ml) was stirred at room temperature for 4 h. The mixture was adjusted to pH=2 using 1 N aqueous HCl, stirred for 1 h, saturated with NaCl and extracted with ethyl acetate. The combined organic phases were dried ($Na_2SO_4$) and the solvents were removed under reduced pressure;

Yield: 2.14 g (quant.)

$R_f$ (II, 10:1)=0.47

EXAMPLE 125

(3a"S*,6a"S*)-3-(5-Methylidene-hexahydro-cyclopenta[c]furan-1-on-6a-ylmethyl)-benzoic acid

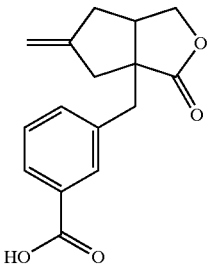

Analogously to Example 124, the title compound was prepared from Example 42 (2.30 g, 8.03 mmol);

Yield: 1.38 g, (63.1%)

$R_f$ (II; 10:1)=0.45

MS (DCI/$NH_3$): m/e=290 [M+$NH^{4+}$]

EXAMPLE 126

(3a"S ,6a"S)-4-(5-Methylidene-hexahydro-cyclopenta[c]furan-1-on-6a-ylmethyl)-benzoic acid

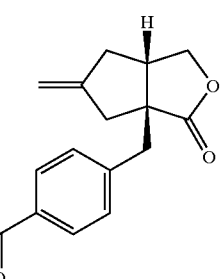

A solution of the compound from Example 92 (2.2 g, 7.68 mmol) in THF (100 ml) and aqueous NaOH (1 M, 127 ml) was stirred at room temperature for 4 h. The mixture was adjusted to pH=2 using 1 N aqueous HCl, stirred for 1 h, saturated with NaCl and extracted with ethyl acetate. The combined organic phases were dried ($Na_2SO_4$) and the solvents were removed under reduced pressure;

Yield: 2.1 g (quant.)

EXAMPLE 127

(3a"S*,6a"S*)-1-[(5-Methylidene-hexahydro-cyclopenta[c]furan-1-on-6a-ylmethyl)-benzoyl]-4-phenylpiperazine

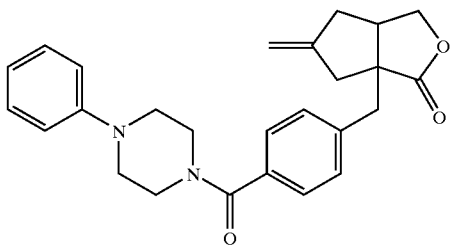

A mixture of the compound from Example 124 (50 mg, 0.184 mmol), N-phenyl-piperazine (32.77 mg, 0.202 mmol), 1-ethyl-3-(3'-dimethylamino)propyl)-carbodiimide hydrochloride (38.7 mg, 0.202 mmol) and triethylamine (18.6 mg, 0.184 mmol) in dichloromethane (10 ml) was stirred at room temperature for 20 h. For work-up, 10% aqueous $KHSO_4$ (1 ml) was added, the reaction mixture was filtered through a frit filled with bituminous earth/silica gel, the solvents were removed under reduced pressure and the crude product was purified by flash chromatography;

Yield: 90 mg (quant.)

$R_f$ (II, 20:1)=0.19

MS (ESI): m/e=417 [M+H$^+$]

Analogously to the procedure of Example 127, the Examples 128 to 177 listed in the table below were prepared starting from Examples 124 or 124, and the Examples 178 to 197 starting from Example 126:

| Ex. No. | Structure | Starting Material Ex. No. | Yield [%] | Rf | MS |
|---|---|---|---|---|---|
| 128 | 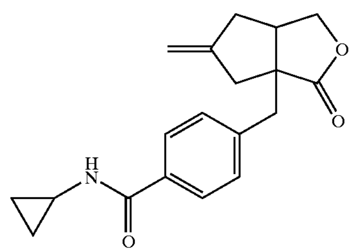 | 124 | 79 | 0.16 (II, 20:1) | 312 [M + H+] |
| 129 | 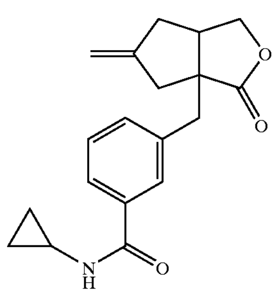 | 125 | 81 | 0.21 (II, 20:1) | 312 [M + H+] |
| 130 | 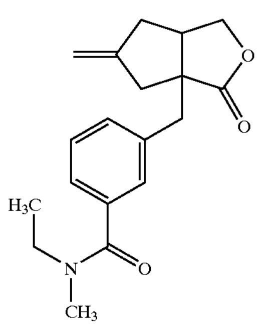 | 125 | 71 | 0.313 (II, 20:1) | 314 [M + H+] |

-continued
| | | | | | |
|---|---|---|---|---|---|
| 131 | 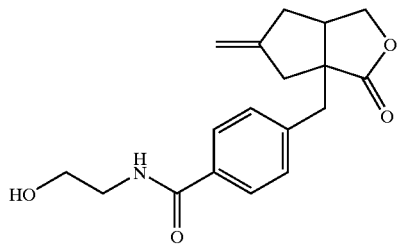 | 124 | 60 | 0.06 (II, 20:1) | 316 [M + H+] |
| 132 | 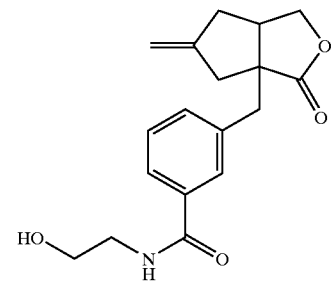 | 125 | 51 | 0.06 (II, 20:1) | 316 [M + H+] |
| 133 | 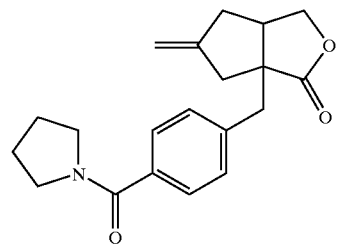 | 124 | 77 | 0.19 (II, 20:1) | 326 [M + H+] |
| 134 | 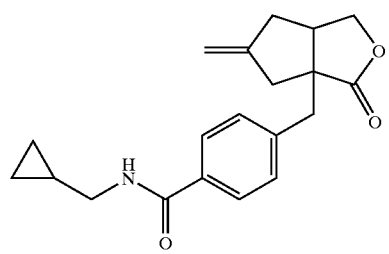 | 124 | 75 | 0.24 (II, 20:1) | 326 [M + H+] |
| 135 | 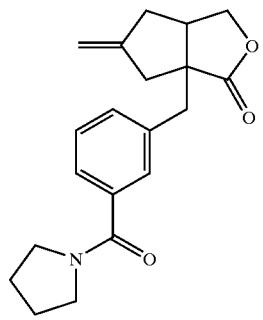 | 125 | 85 | 0.20 (II, 20:1) | 326 [M + H+] |

-continued
| | | | | | |
|---|---|---|---|---|---|
| 136 | 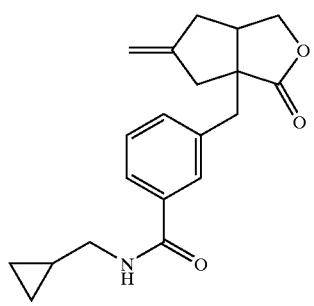 | 125 | 78 | 0.21 (II, 20:1) | 326 [M + H+] |
| 137 | 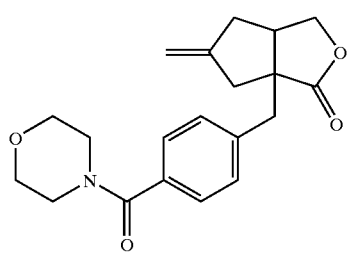 | 124 | 27 | 0.24 (III, 4:1) | 342 [M + H+] |
| 138 | 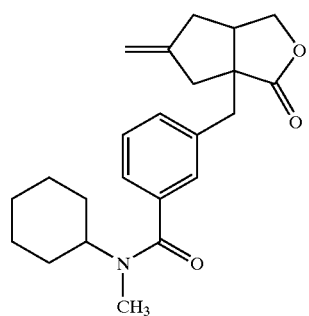 | 125 | 35 | 0.25 (II, 20:1) | 368 [M + H+] |
| 139 | 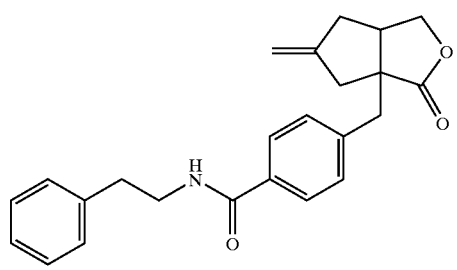 | 124 | 70 | 0.22 (II, 20:1) | 376 [M + H+] |
| 140 | 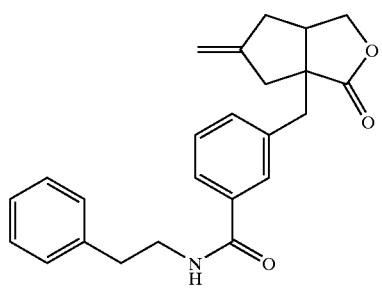 | 125 | 91 | 0.23 (II, 20:1) | 376 [M + H+] |

-continued
| | | | | | |
|---|---|---|---|---|---|
| 141 | 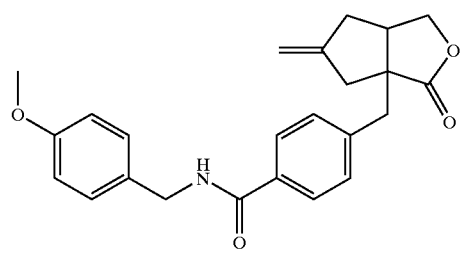 | 124 | 59 | 0.25 (II, 20:1) | 392 [M + H+] |
| 142 | 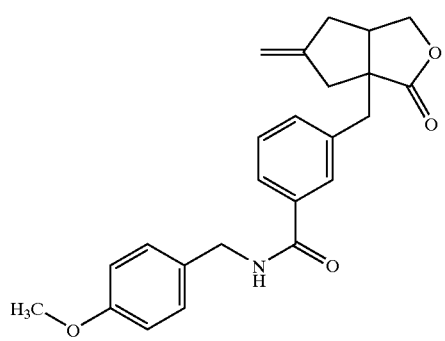 | 125 | 66 | 0.25 (II, 20:1) | 392 [M + H+] |
| 143 | 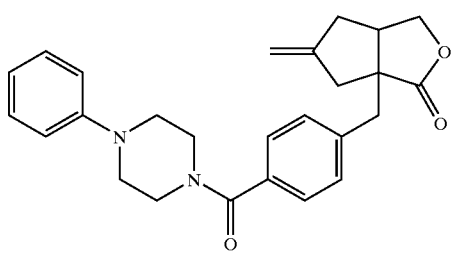 | 124 | 82 | 0.21 (II, 20:1) | 417 [M + H+] |
| 144 | 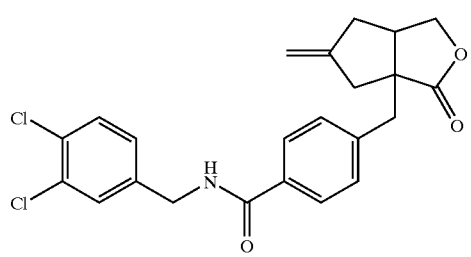 | 124 | 77 | 0.29 (II, 20:1) | 431 [M + H+] |
| 145 | 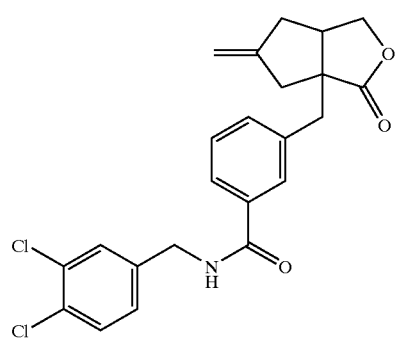 | 125 | 58 | 0.213 (II, 20:1) | 431 [M + H+] |

-continued
| | | | | | |
|---|---|---|---|---|---|
| 146 | 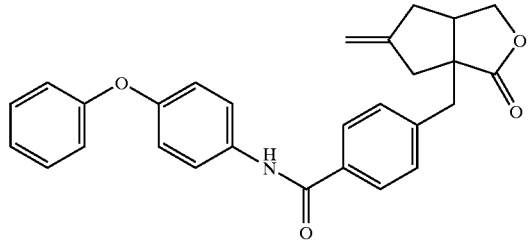 | 124 | 67 | 0.33 (II, 20:1) | 440 [M + H+] |
| 147 | 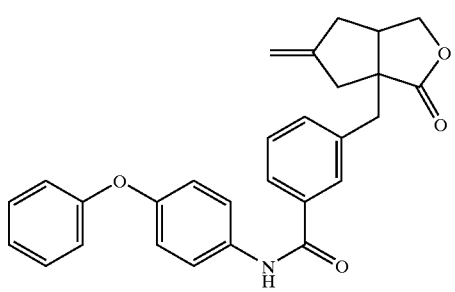 | 125 | 81 | 0.43 (II, 20:1) | 440 [M + H+] |
| 148 | 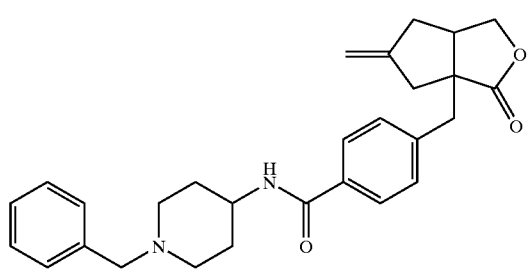 | 124 | 53 | 0.05 (II, 20:1) | 445 [M + H+] |
| 149 | 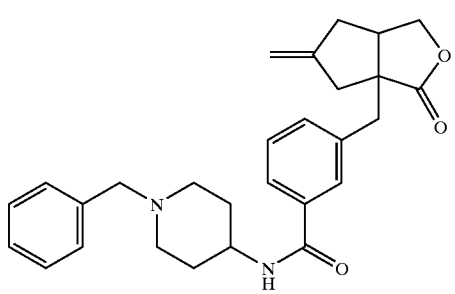 | 125 | 52 | 0.04 (II, 20:1) | 445 [M + H+] |
| 150 | 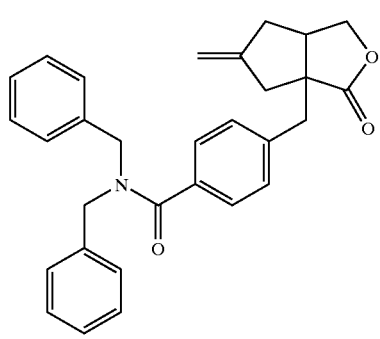 | 124 | 93 | 0.25 (II, 20:1) | 452 [M + H+] |

-continued
| Ex. No. | Structure | Starting Material Ex. No. | MW [g/mol] | HPLC area % at 210 nm | MS [M + H+] |
|---|---|---|---|---|---|
| 151 | 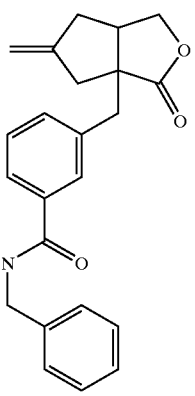 | 125 | 71 | 0.28 (II, 20:1) | 452 [M + H+] |
| 152 | 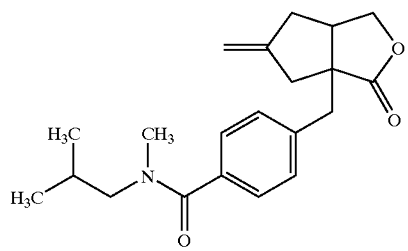 | 124 | 341.4542 | 97 | 342 |
| 153 | 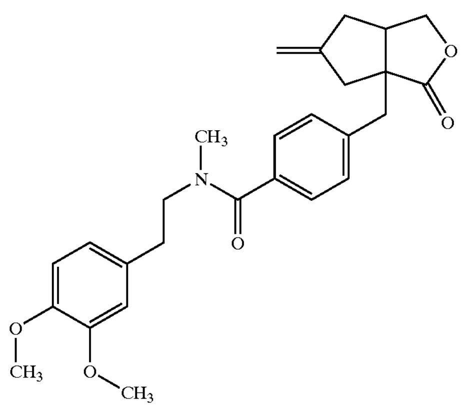 | 124 | 449.5518 | 97 | 450 |
| 154 | 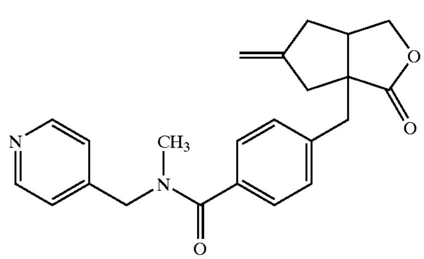 | 124 | 376.4593 | 92 | 377 |
| 155 | 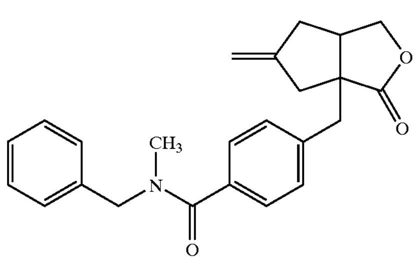 | 124 | 375.4718 | 96 | 376 |

-continued

| | | | | | |
|---|---|---|---|---|---|
| 156 | (structure) | 124 | 361.4447 | 96 | 362 |
| 157 | (structure) | 124 | 341.4542 | 96 | 342 |
| 158 | (structure) | 124 | 367.4925 | 95 | 368 |
| 159 | (structure) | 124 | 430.3347 | 96 | 430 |
| 160 | (structure) | 124 | 409.9168 | 95 | 410 |
| 161 | (structure) | 124 | 440.3407 | 96 | 440 |

-continued

| | | | | | |
|---|---|---|---|---|---|
| 162 | | 124 | 339.4383 | 96 | 340 |
| 163 | | 124 | 444.3618 | 95 | 444 |
| 164 | | 124 | 362.4322 | 97 | 363 |
| 165 | | 124 | 377.4441 | 98 | 378 |
| 166 | | 124 | 369.5084 | 94 | 370 |

-continued

| | | | | | |
|---|---|---|---|---|---|
| 167 | | 124 | 347.4176 | 94 | 348 |
| 168 | | 124 | 475.5958 | 94 | 476 |
| 169 | | 124 | 399.4354 | 96 | 400 |
| 170 | | 124 | 367.3714 | 93 | 368 |
| 171 | | 124 | 313.4001 | 96 | 314 |
| 172 | | 124 | 329.3995 | 99 | 330 |

-continued
| | | | | | |
|---|---|---|---|---|---|
| 173 | 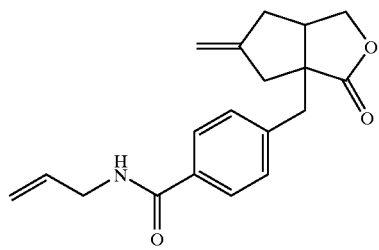 | 124 | 311.3841 | 95 | 312 |
| 174 | 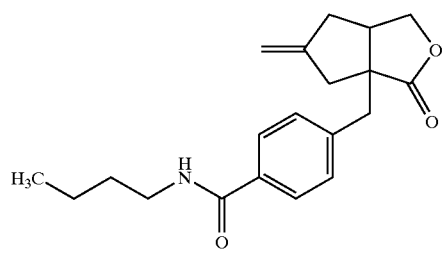 | 124 | 327.4272 | 94 | 328 |
| 175 | 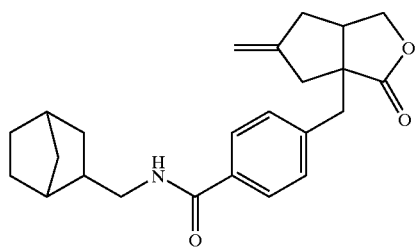 | 124 | 379.5036 | 95 | 380 |
| 176 | 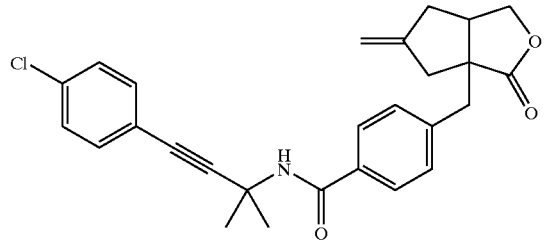 | 124 | 447.9662 | 64 | 448 |
| 177 | 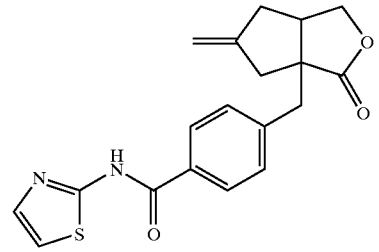 | 124 | 354.4309 | 51 | 355 |

-continued
| Ex. No. | Structure | Molecular weight [g/mol] | HPLC area % at 210 nm | MS [M + H+] |
|---|---|---|---|---|
| 178 | 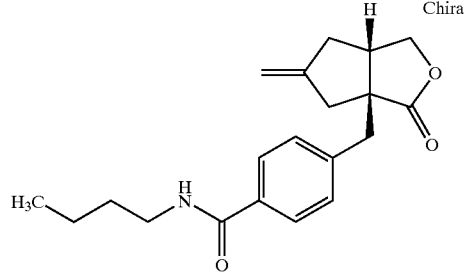 | 327.43 | 85 | 369 |
| 179 | 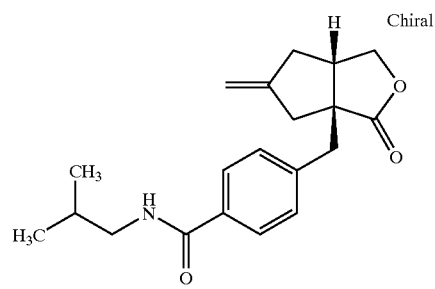 | 327.43 | 92 | 369 |
| 180 | 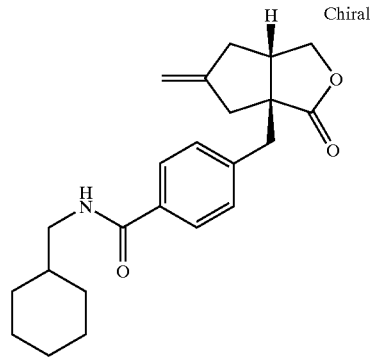 | 367.49 | 89 | 409 |
| 181 | 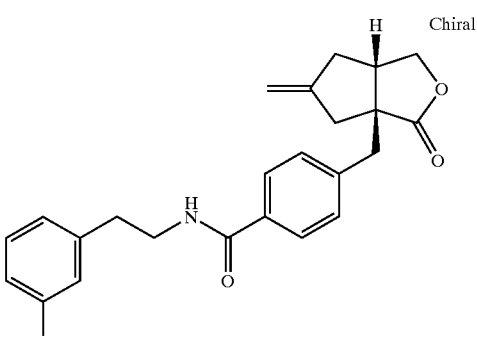 | 409.92 | 94 | 451 |

-continued
| | | | | | |
|---|---|---|---|---|---|
| 182 | 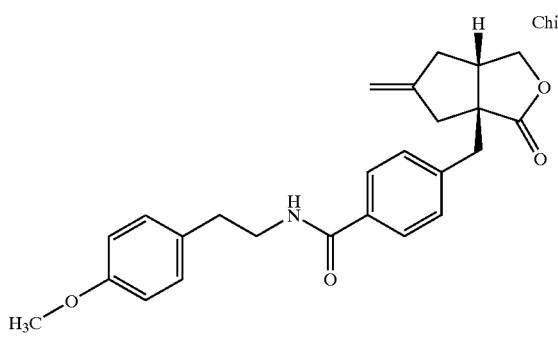 | Chiral | 405.50 | 88 | 447 |
| 183 | 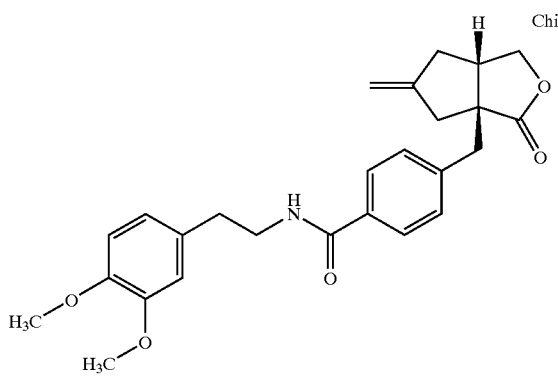 | Chiral | 435.52 | 96 | 477 |
| 184 | 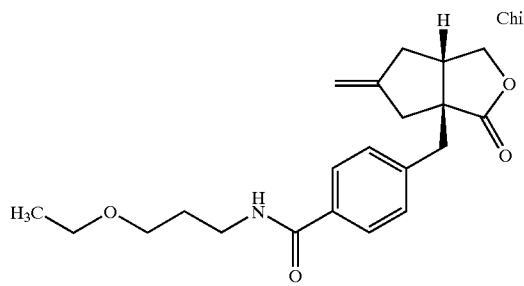 | Chiral | 357.45 | 91 | 358 |
| 185 | 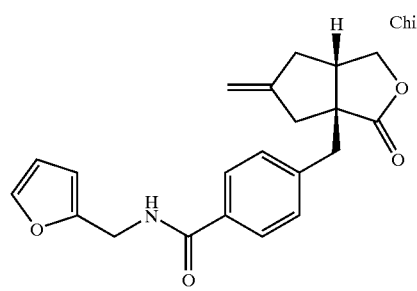 | Chiral | 351.41 | 89 | 393 |
| 186 | 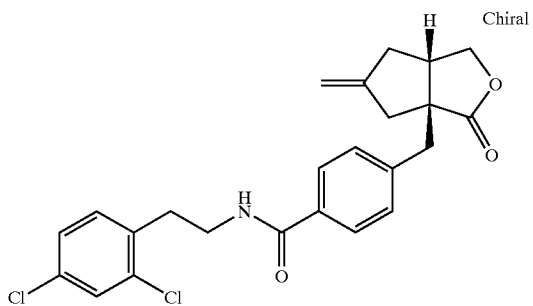 | Chiral | 444.36 | 79 | 485 |

-continued
| | | | | | |
|---|---|---|---|---|---|
| 187 | 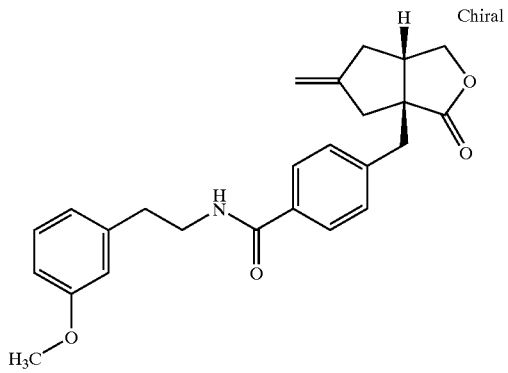 | Chiral | 405.50 | 93 | 447 |
| 188 | 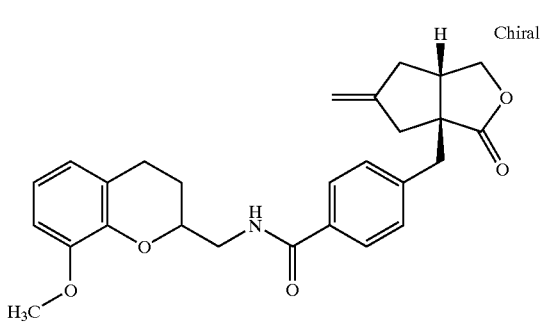 | Chiral | 447.54 | 91 | 448 |
| 189 | 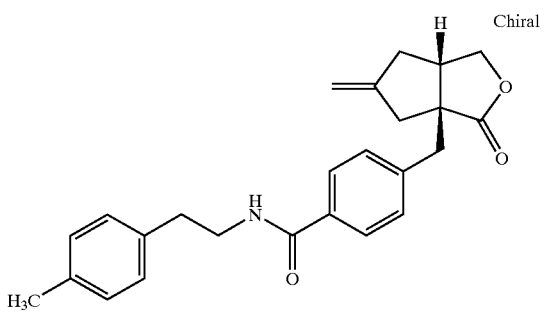 | Chiral | 389.50 | 90 | 431 |
| 190 | 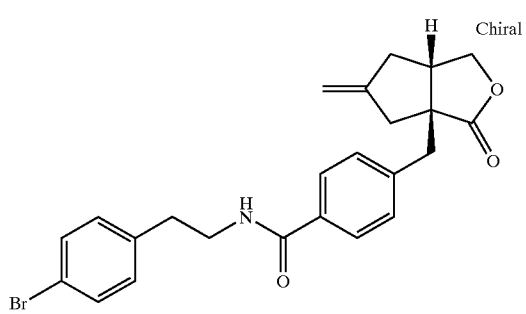 | Chiral | 454.37 | 90 | 495 |
| 191 | 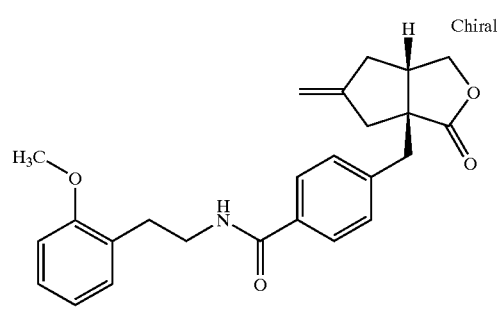 | Chiral | 405.50 | 93 | 447 |

| | | | | | |
|---|---|---|---|---|---|
| 192 | 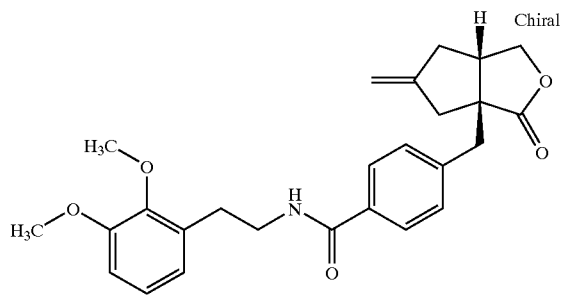 | | 435.52 | 97 | 436 |
| 193 | 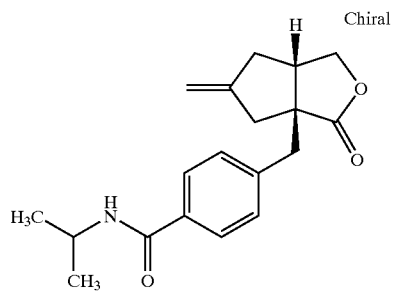 | | 313.40 | 83 | 355 |
| 194 | 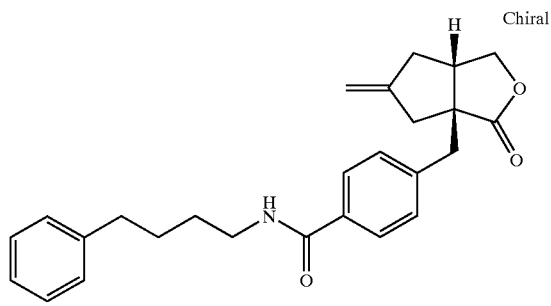 | | 403.53 | 93 | 445 |
| 195 | 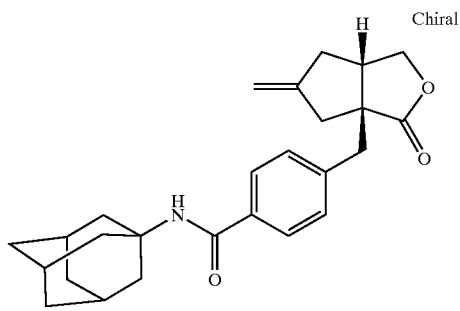 | | 405.54 | 57 | 447 |
| 196 | 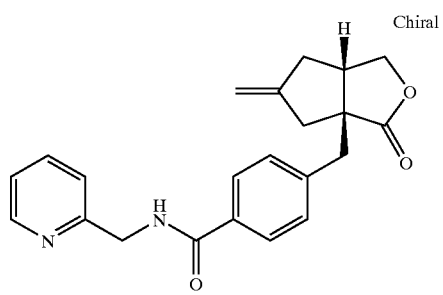 | | 362.43 | 94 | 363 |

-continued

| | | | | | |
|---|---|---|---|---|---|
| 197 | 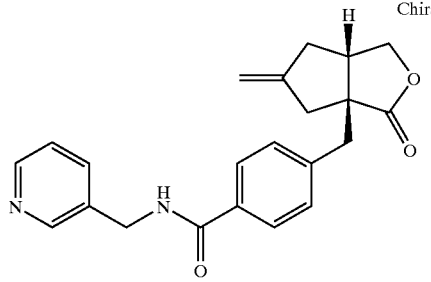 | Chiral | 362.43 | 98 | 363 |

EXAMPLE 198

Isopropyl (3a"S*,6a"S*)-4-(-methylidene-hexahydro-cyclopenta[c]furan-1-on-6a-ylmethyl)-benzoate

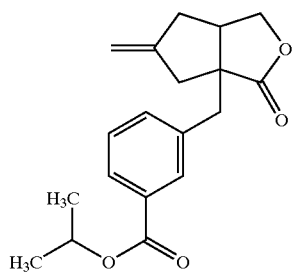

At room temperature, triethylamine (51 µl, 0.367 mmol) and methanesulphonyl chloride (14.2 µl, 0.184 mmol) were added to a solution of the compound from Example 125 (50.0 mg, 0.184 mmol) in dichloromethane (2 ml). After 1 h, 2-propanol (10.6 µl, 0.138 mmol) and dimethylaminopyridine (4.5 mg, 0.037 mmol) were added, and the mixture was stirred at room temperature for another 20 h. For work-up, the mixture was admixed with 10% aqueous $NaHCO_3$ solution (1 ml) and filtered through a frit filled with bituminous earth/silica gel, the solvents were removed and the crude product was purified by chromatography;

Yield: 19 mg (32%)

$R_f$ (II, 100:1)=0.47

MS (ESI): m/e=337 [M+Na$^+$]

The Examples 199 to 209 listed in the table below were prepared analogously to the procedure given above.

| Ex. No. | Structure | Starting Material Ex. No. | Yield [%] | Rf | MS |
|---|---|---|---|---|---|
| 199 | 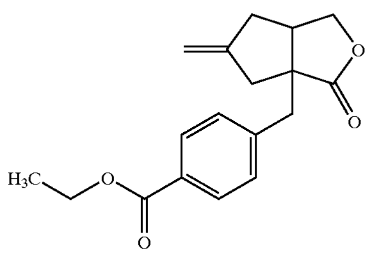 | 124 | 49 | 0.43(II, 100:1) | 342[M + CH3CN + H+] |
| 200 | 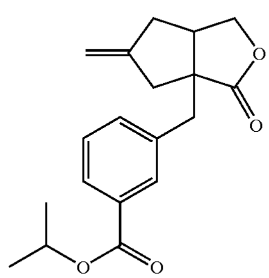 | 125 | 53 | 0.61(II, 100:1) | 349[M + H+] |

-continued

| Ex. No. | Structure | Starting Material Ex. No. | Yield [%] | Rf | MS |
|---|---|---|---|---|---|
| 201 | 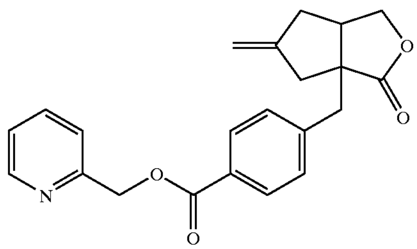 | 124 | 49 | 0.90(II, 100:1) | 364[M + H+] |
| 202 | 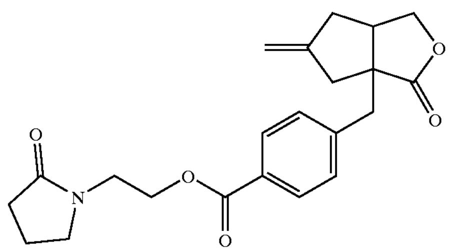 | 124 | 64 | 0.62(II, 100:1) | 384[M + H+] |
| 203 | 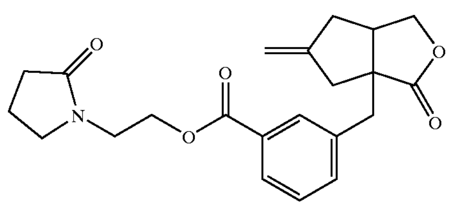 | 125 | 61 | 0.27(II, 20.1) | — |
| 204 | 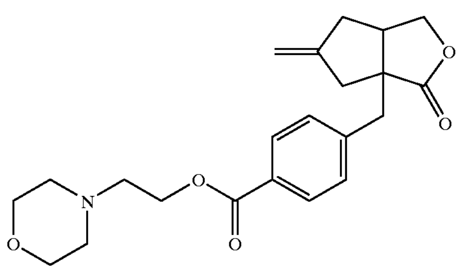 | 124 | 71 | 0.63(II, 100:1) | 386[M + H+] |
| 205 | 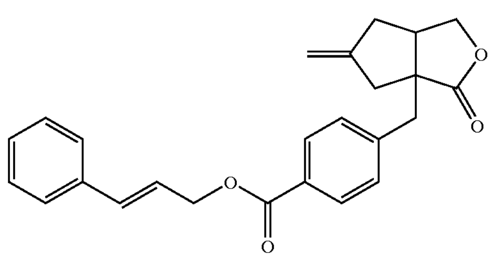 | 124 | 79 | 0.54(II, 100:1) | 411[M + Na+] |
| 206 | 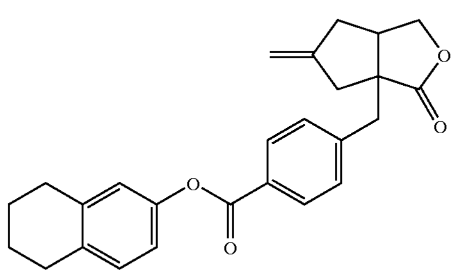 | 124 | 19 | 0.60(II, 100:1) | 403[M + H+] |

-continued

| Ex. No. | Structure | Starting Material Ex. No. | Yield [%] | Rf | MS |
|---|---|---|---|---|---|
| 207 | 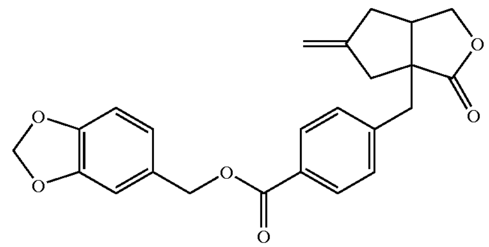 | 124 | 50 | 0.43(II, 100:1) | 429[M + Na+] |
| 208 | 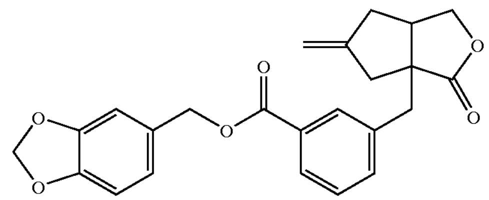 | 125 | 62 | 0.46(II, 100:1) | 424[M + NH4+] |
| 209 | 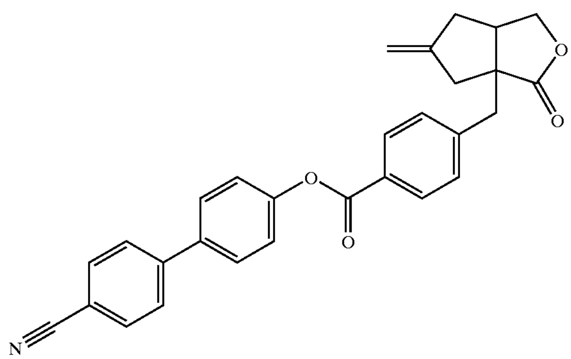 | 124 | 56 | 0.41(II, 100:1) | 450[M + H+] |

Examples 210 to 214 listed in the table below were prepared analogously to the procedure of Example 98:

| Ex. No. | Structure | Starting Material Ex. No. | Yield (%) | $R_f$ | MS [M + NH$_4^+$] |
|---|---|---|---|---|---|
| 210 | 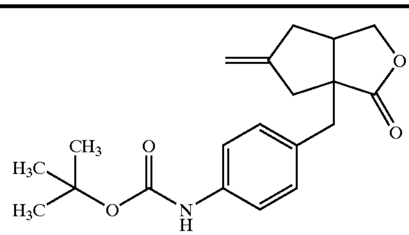 | 124 | 56 | 0.80(III, 1:1) | 361 |
| 211 | 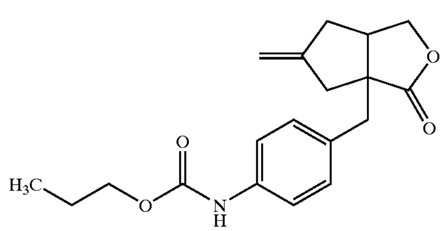 | 124 | 45 | 0.52(III, 2:1) | 347 |

-continued

| Ex. No. | Structure | Starting Material Ex. No. | Yield (%) | $R_f$ | MS [M + NH$_4^+$] |
|---|---|---|---|---|---|
| 212 | 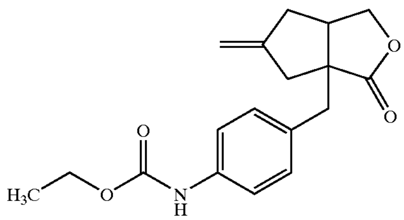 | 124 | 44 | 0.48(III, 2:1) | 333 |
| 213 | 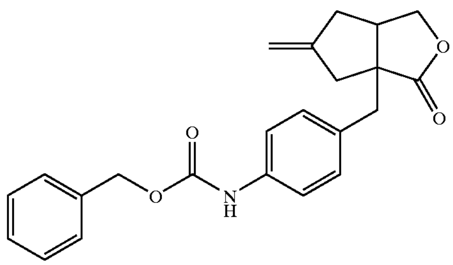 | 124 | 15 | 0.51(III, 2:1) | 342 |
| 214 | Chiral | 126 | 64 | 0.23(III, 5:1) | 345 |

Examples 215 to 231 listed in the table below were prepared analogously to the procedure of Example 1:

| Ex. No. | Structure | Starting Material Ex. No. | Yield (%) | $R_f$ | MS |
|---|---|---|---|---|---|
| 215 | 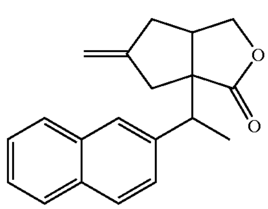 | 1A | 30 | 0.52(III; 5:1) | 404[M + H$^+$] |
| 216 | 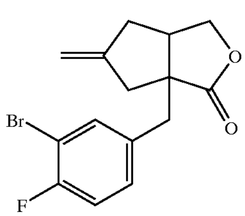 | 1A | 29 | 0.61(CH$_2$Cl$_2$) | 342[M + H$^+$] |

-continued

| Ex. No. | Structure | Starting Material Ex. No. | Yield (%) | $R_f$ | MS |
|---|---|---|---|---|---|
| 217 | 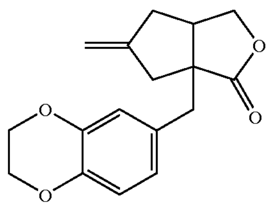 | 1A | 15 | 0.52(I, 80:1) | 348[M + H⁺] |
| 218 | 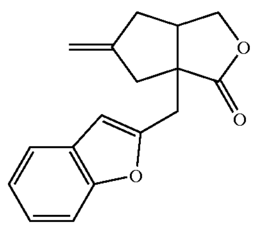 | 1A | 5 | 0.17(I, 80:1) | 269[M + H⁺] |
| 219 | 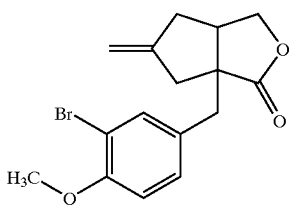 | 1A | 11 | 0.47(III, 5:1) | 339[M + H⁺] |
| 220 | 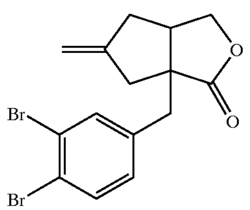 | 1A | 30 | 0.20(IV, 5:1) | 404[M + NH₄⁺] |
| 221 | 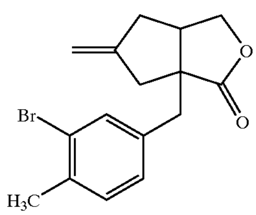 | 1A | 20 | 0.50(IV, 1:1) | 322[M + Na⁺] |
| 222 | 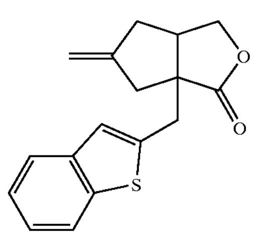 | 1A | 35 | 0.82(I, 80:1) | 227[M + NH₄⁺] |
| 223 | 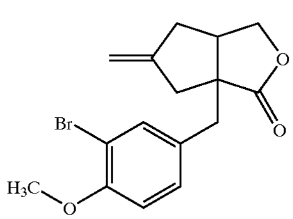 | 1A | 18 | 0.42(III, 50:1) | 339[M + NH₄⁺] |

-continued

| Ex. No. | Structure | Starting Material Ex. No. | Yield (%) | $R_f$ | MS |
|---|---|---|---|---|---|
| 224 | Chiral | 2A | 40 | 0.16(CH$_2$Cl$_2$) | — |
| 225 | 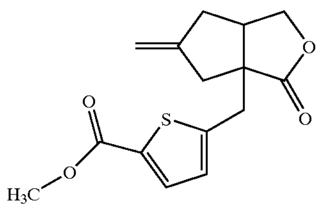 | 1A | 9 | 0.62(CH$_2$Cl$_2$) | 310[MN + NH$_4^+$] |
| 226 | 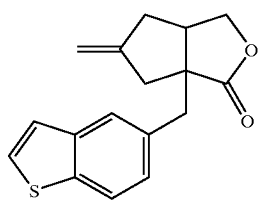 | 1A | 31 | 0.35(CH$_2$Cl$_2$) | 285[M + H$^+$] |
| 227 | 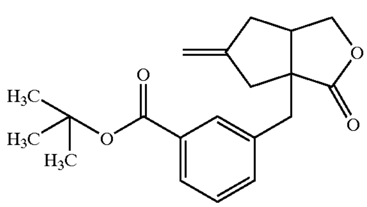 | 1A | 7 | 0.24(III, 100:1) | 329[M + H$^+$] |
| 228 | 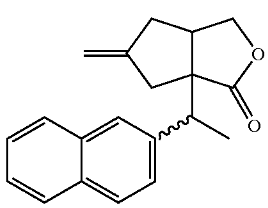 | 1A | 15 | 0.52(III, 5:1)[a)] | 404[M + H$^+$] |
| 229 | 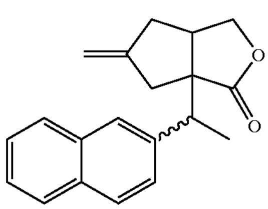 | 1A | 15 | 0.52(III; 5:1)[b)] | 404[M + H$^+$] |

-continued
| Ex. No. | Structure | Starting Material Ex. No. | Yield (%) | R$_f$ | MS |
|---|---|---|---|---|---|
| 230 | 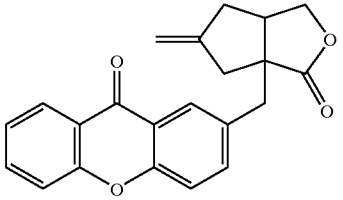 | 1A | 25 | 0.31(I, 40:1) | 347[M + H$^+$] |
| 231 | Chiral 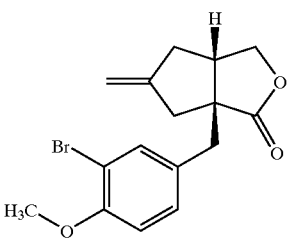 | 2A | 52 | 0.42(I, 40:1) | 339[M + H$^+$] |
a) Diastereomer A: fraction 1 (HPLC, Kromasil 100 C. 18, methanol/H$_2$O 65:35)
b) Diastereomer B: fraction 2 (HPLC, Kromasil 100 C. 18, methanol/H$_2$O 65:35)
Examples 232 to 255 listed in the table below were prepared analogously to the compound from Example 106:
| Ex. No. | Structure | MW (g/mol) | HPLC area % at 210 nm | Mz + H |
|---|---|---|---|---|
| 232 | 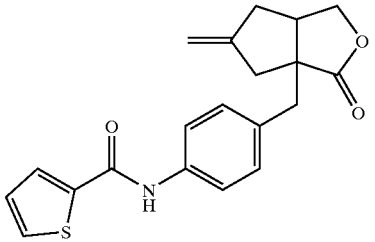 | 353.44 | 92 | 354 |
| 233 | 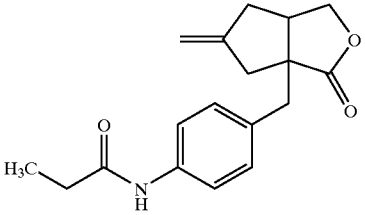 | 299.37 | 75 | 300 |
| 234 | 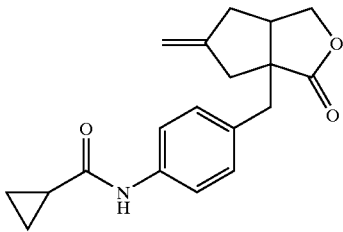 | 311.38 | 96 | 312 |

-continued

| Ex. No. | Structure | MW (g/mol) | HPLC area % at 210 nm | Mz + H |
|---|---|---|---|---|
| 235 | 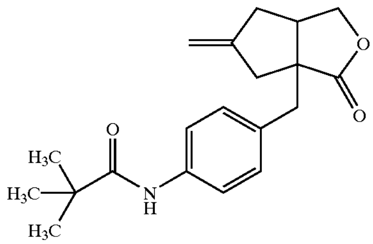 | 327.42 | 98 | 328 |
| 236 | 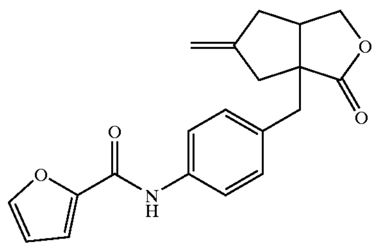 | 337.37 | 97 | 338 |
| 237 | 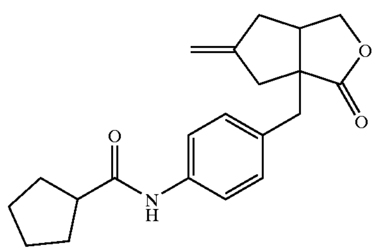 | 339.43 | 89 | 340 |
| 238 | 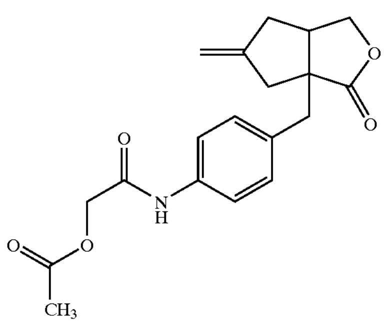 | 343.38 | 96 | 344 |
| 239 | 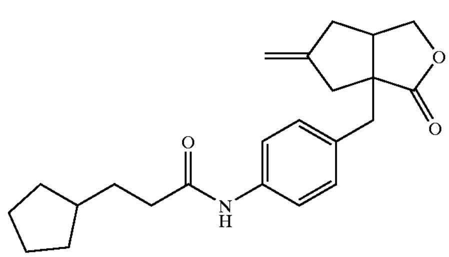 | 367.49 | 88 | 368 |

-continued

| Ex. No. | Structure | MW (g/mol) | HPLC area % at 210 nm | Mz + H |
|---|---|---|---|---|
| 240 | 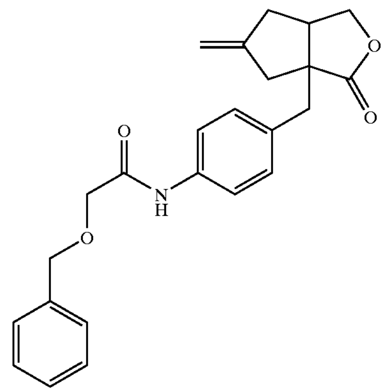 | 391.47 | 97 | 392 |
| 241 | 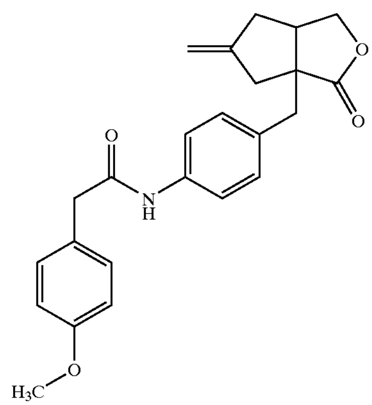 | 391.47 | 97 | 392 |
| 242 | 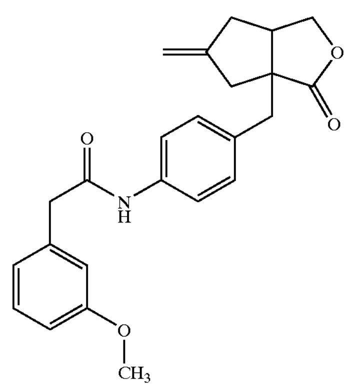 | 391.47 | 95 | 392 |
| 243 | 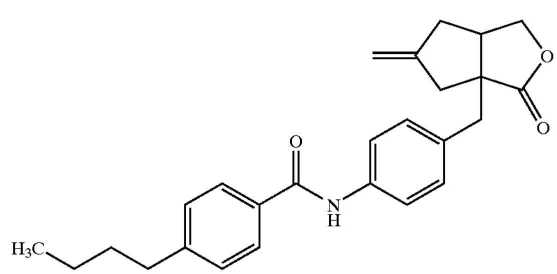 | 403.52 | 91 | 404 |

-continued

| Ex. No. | Structure | MW (g/mol) | HPLC area % at 210 nm | Mz + H |
|---|---|---|---|---|
| 244 | 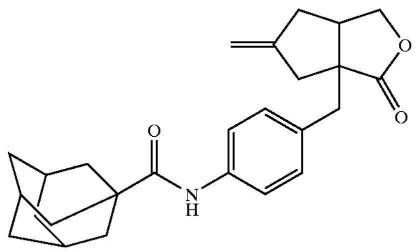 | 405.54 | 92 | 244 |
| 245 | 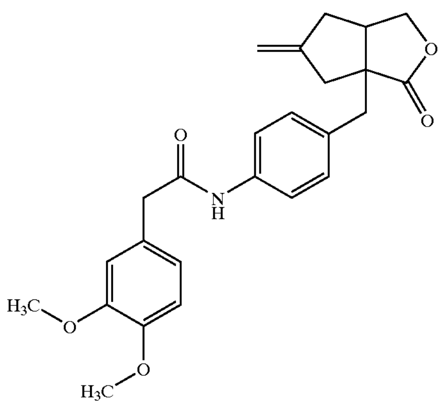 | 421.49 | 82 | 422 |
| 246 | 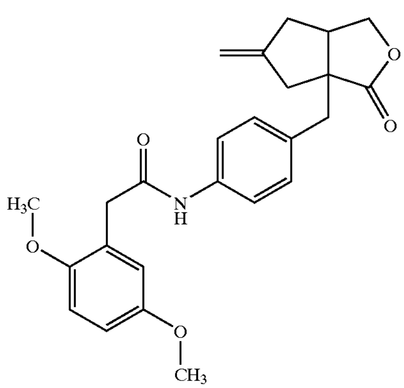 | 421.49 | 95 | 422 |
| 247 | 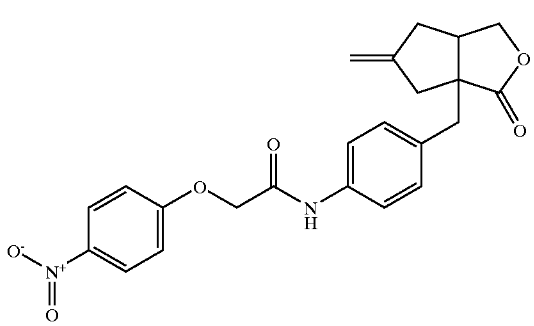 | 422.44 | 6 | 423 |

-continued

| Ex. No. | Structure | MW (g/mol) | HPLC area % at 210 nm | Mz + H |
|---|---|---|---|---|
| 248 | 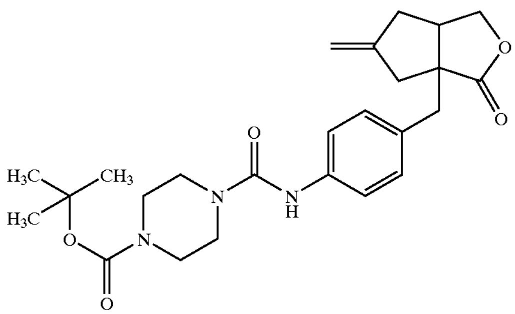 | 455.55 | 61 | 456 |
| 249 | 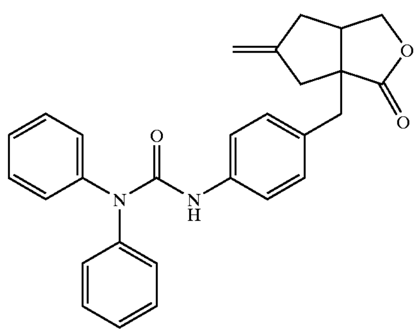 | 438.53 | 16 | 439 |
| 250 | 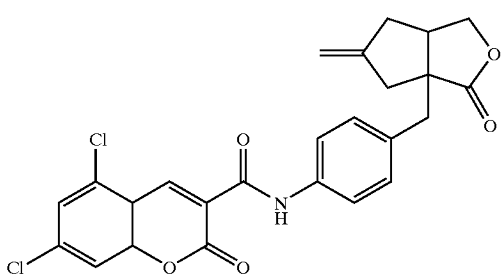 | 486.35 | 49 | 486 |
| 251 | 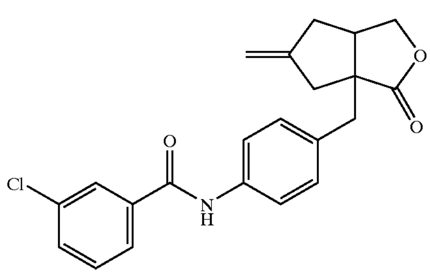 | 381.86 | 95 | 382 |
| 252 | 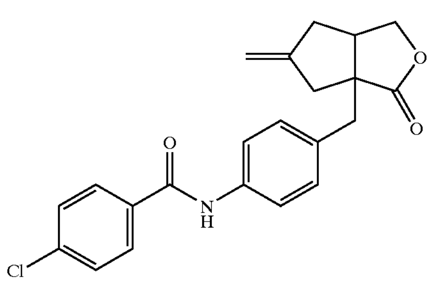 | 381.86 | 94 | 382 |

-continued

| Ex. No. | Structure | MW (g/mol) | HPLC area % at 210 nm | Mz + H |
|---|---|---|---|---|
| 253 | 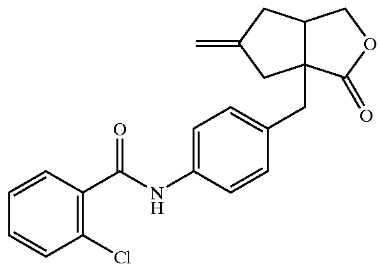 | 381.86 | 94 | 382 |
| 254 | 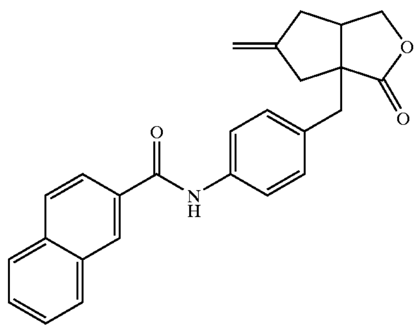 | 397.47 | 92 | 398 |
| 255 | 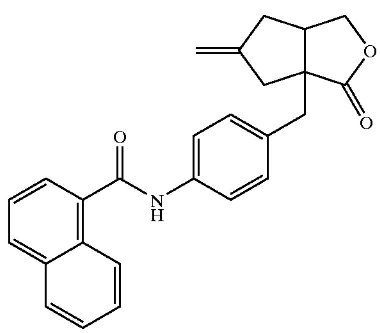 | 397.47 | 98 | 398 |

The compounds listed in the table below were prepared analogously to Example 106:

| Ex. No. | Structure | Yield (%) | MS |
|---|---|---|---|
| 256 | 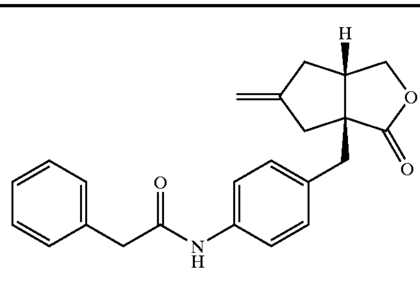 | 87 | 362[M + H$^+$] |

| Ex. No. | Structure | Yield (%) | MS |
|---|---|---|---|
| 257 | 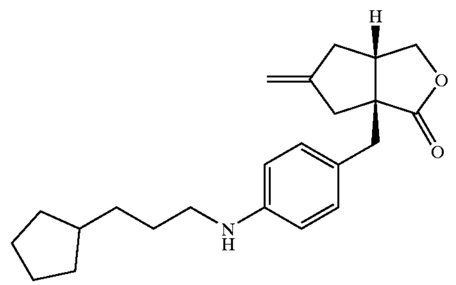 | 80 | 409[M + H₃CCN + H⁺] |
| 258 | 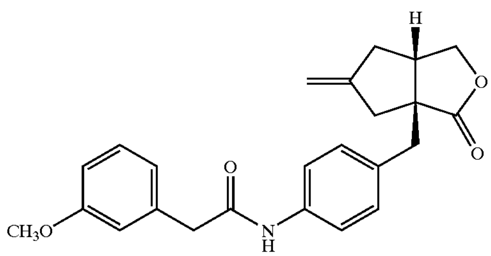 | 97 | 392[M + H⁺] |

EXAMPLE 259

N[(3a"S*,6a"S)-4-(5-Methylidene-hexahydro-cyclopenta[c]furan-1-on-6a-ylmethyl-phenyl]-4-methylpentanecarboxamide

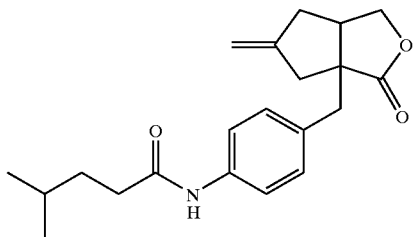

At 0° C., N,N-dimethylaminopyridine (10.1 mg, 0.09 mmol), 1-ethyl-3-(3'-dimethylamino)propyl)-carbodiimide hydrochloride (17.3 mg, 0.09 mmol) and 4-methyl-pentanecarboxylic acid (10.5 mg, 0.09 mmol) were added to a solution of the compound from Example 104 (20.0 mg, 0.082 mmol) in dichloromethane (5 ml), and the reaction mixture was stirred at room temperature for 6 hours. For work-up, 1 M aqueous HCl was added (0.7 ml), the mixture was filtered, with dichloromethane, through a frit filled with bituminous earth/silica gel, the filtrate was admixed with 10% aqueous NaHCO₃ (0.7 ml) and filtered once more through a frit filled with bituminous earth, and the solvent was removed under reduced pressure.

Yield: 27.6 mg (98%)

$R_f$ (III, 2:1)=0.38

MS(ESI): m/e=342 [M+H⁺]

EXAMPLE 260

(3aS*,6aS*)-6a-(4-(2-Methylpropylaminobenzyl)-5-methylidene-hexahydro-cyclo-penta[c]furan-1-one

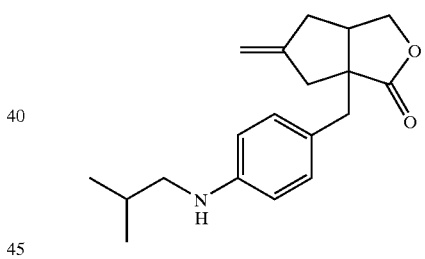

A solution of the compound from Example 104 (15 mg, 0.062 mmol), 2-methyl-propanal (4.5 mg, 0.062 mmol) in methanol/acetic acid (3:1, 1.2 ml) was stirred at room temperature for 20 minutes and then admixed with sodium cyanoborohydride (5.0 mg, 0.08 mmol) in methanol (0.6 ml). After 20 hours, the mixture was admixed with ether and the organic phase was washed with sat. NaHCO₃ and dried (MgSO₄). The residue was purified by chromatography.

Yield: 3.7 mg (20%)

$R_f$ (II, 50:1)=0.35

MS (ESI): m/e=300 [M+H⁺]

EXAMPLE 261

(3aS*,6aS*)-6a-(4-Hydroxybenzyl)-5-methylidene-hexahydro-cycopenta[c]furan-1-one

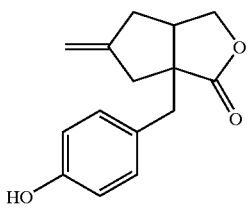

A mixture of the compound from Example 279 (192 mg, 0.59 mmol), $K_2CO_3$ (486 mg, 3.52 mmol) in water (4.7 ml) and methanol (7.1 ml) was stirred at room temperature for 30 minutes. The mixture was adjusted to pH=2 using 1 N aqueous HCl, saturated with NaCl and extracted with ethyl acetate. The combined organic phases was dried ($Na_2SO_4$) and the solvents were removed under reduced pressure.

Yield: 157 mg (quant.)
$R_f$ (III, 2:1)=0.31
MS (ESI): m/e=286 [M+H$^+$]

EXAMPLE 262

(3aS*,6aS*)-6a-(4-(3-Methylbutyloxy)benzyl)-5-methylidene-hexahydro-cyclopenta[c]furan-1-one

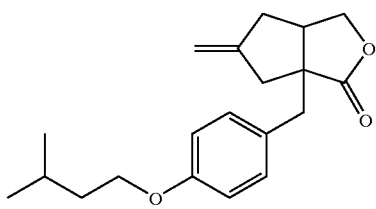

A mixture of the compound from Example 261 (13.3 mg, 0.054 mol), 1-bromo-3-methylbutane (6.8 mg, 0.045 mmol), $Cs_2CO_3$ (44.4 mg, 0.136 mmol) in dimethoxyethane (5 ml) was stirred at 75° C. for 48 hours. For work-up, the mixture was admixed with dichloromethane and 1 M aqueous NaOH and filtered through a frit filled with bituminous earth, the solvent was removed under reduced pressure and the residue was purified by chromatography.

Yield: 2.8 mg (16%)
$R_f$ (III, 5:1)=0.49
LCMS: m/e=356 [M+$H_3$CCN+H$^+$]

EXAMPLE 263 and 264

N-[(3a"R*,6a"R*)-4-(5-Methylidene-hexahydro-cyclopenta[c]furan-1-on-6a-yl-methyl)-phenyl]-(3-methoxyphenyl)acetamide (264) and N-[(3a"S*,6a"S*)-4-(5-Methyl-3,3a,6,6a-tetrahydro-cyclopenta[c]furan-1-on-6a-yl-methyl)-phenyl]-(3-methoxyphenyl)acetamide (265)

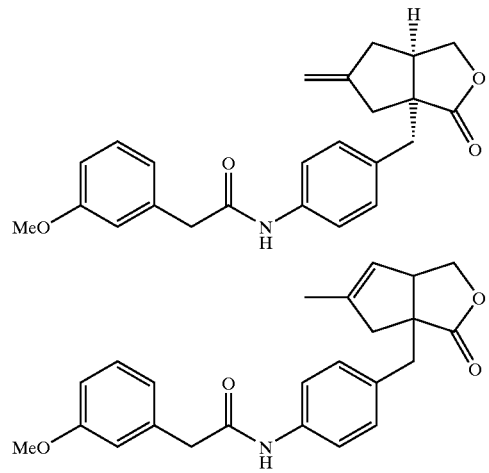

The compound from Example 104 and 3-methoxyphenylacetyl chloride were reacted analogously to the procedure of Example 106. The crude product was separated into the enantiomers by HPLC (Chiralpak AS, ethanol/iso-hexane 20:80).

Fraction I (Example 265): Enantiomer A, [α]$_D^{20}$=−46° (c=0.473, CHCl$_3$)

Fraction II: not identified

Fraction III (Example 264): Enantiomer A, [α]$_D^{20}$=−22.2° (c=0.200, CHCl$_3$)

Fraction IV (Example . . . ): Enantiomer B

The compounds listed in the table were prepared analogously to the procedure of Example 1:

| Ex. | Structure | Starting Material Ex. No. | Yield [%] | Rf(cyclohexane/ ethyl acetate 3:1) | MS(CI) [M$^+$ + 1] |
|---|---|---|---|---|---|
| 265 | 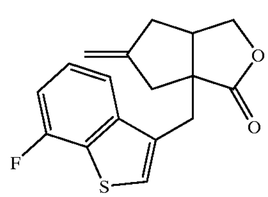 | 1A | 9.9 | 0.50 | 303 |

-continued
| | | | | | |
|---|---|---|---|---|---|
| 266 | 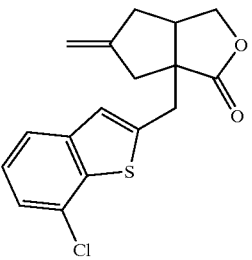 | 1A | 3.5 | 0.51 | 319 |
| 267 | 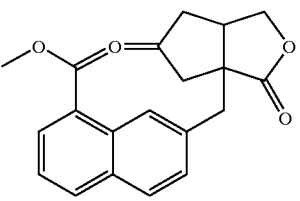 | 1A | 6.8 | 0.42 | 337 |
| 268 | 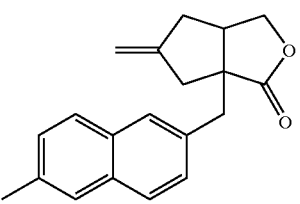 | 1A | 10.2 | 0.63 | 335 |
| 269 | 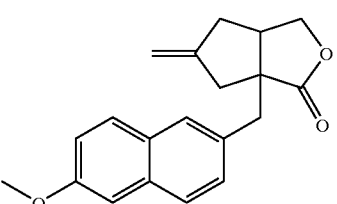 | 1A | 29.2 | 0.46 | 309 |
| 270 | 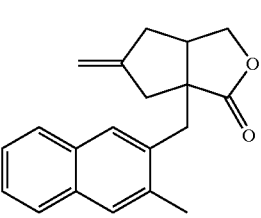 | 1A | 15.4 | 0.54 | 293 |
| 271 | 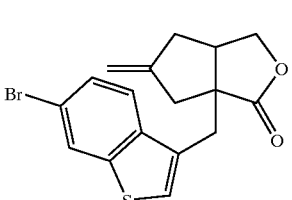 | 1A | 9.1 | 0.52 | 364 |
| 272 | 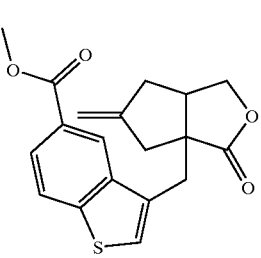 | 1A | 8.2 | 0.39 | 343 |

-continued
| Ex. No. | Structure | | | Yield % | Starting Material | Procedure analogous to Ex. | Rf | MS |
|---|---|---|---|---|---|---|---|---|
| 273 | 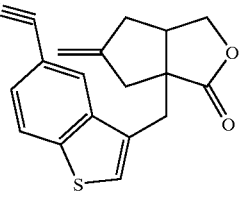 | 1A | 21.0 | 0.35 | 310 | | | |
| 274 | 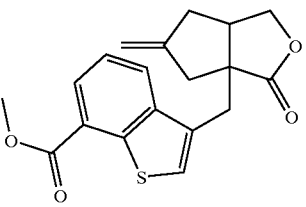 | 1A | 10.5 | 0.36 | 343 | | | |
| 275 | 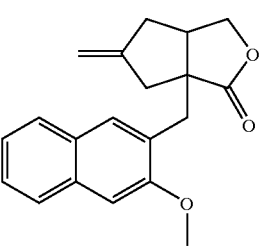 | 1A | 13.0 | 0.46 | 309 | | | |
| 276 | 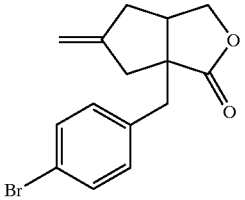 | | | 39 | 1A | 1 | 0.5(CH2Cl2) | 324[M + NH4+] |
| 277 | 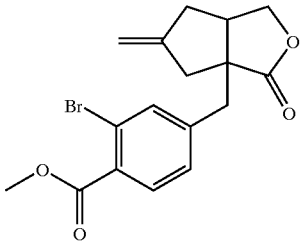 | | | 22 | 1A | 1 | 0.50(II, 1:1) | 382/384[M + NH4+] |
| 278 | 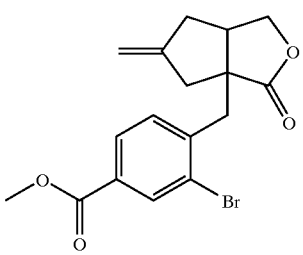 | | | 17 | 1A | 1 | 0.53(III, 2:1) | 382/384[M + NH4+] |

-continued

| | | | | | | |
|---|---|---|---|---|---|---|
| 279 | (structure) | 30 | 1A | 1 | 0.20(III, 5:1) | |
| 280 | (structure) | 43 | 1A | 1 | | 407[M + H*] |

The examples listed in the table below were prepared analogously to the procedures mentioned.

| Ex. No. | Structure | Yield % | Starting Material | Procedure analogous to Ex. | Rf | MS |
|---|---|---|---|---|---|---|
| 281 | (structure) | 30 | 124 | 98 | 0.23(II, 20:1) | 401[M + H + 9] |
| 282 | Chiral (structure) | 27 | 124 | 98 | 0.47(III, 2:1) | 330[M + H+] |
| 283 | (structure) | 26 | 318 | 98 | 0.36(I, 40:1) | 336[M + H+] |

| Ex. No. | Structure | Yield % | Starting Material | Procedure analogous to Ex. | Rf | MS |
|---|---|---|---|---|---|---|
| 284 | 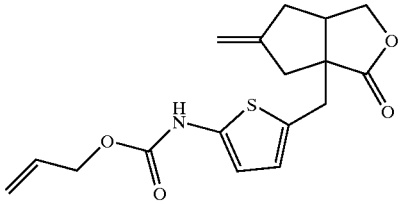 | 20 | 318 | 98 | 0.34(I, 40:1) | 351[M + NH4+] |
| 285 | 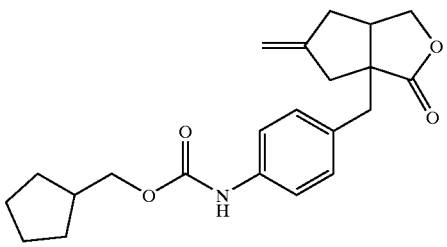 | 88 | 124 | 98 | 0.23(III, 5:1) | 370[M + H+] |
| 286 | 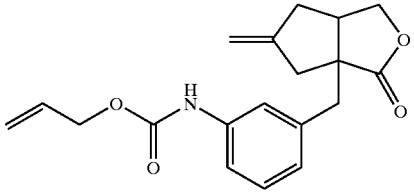 | 73 | 125 | 98 | 0.15 (CH2Cl2) | |
| 287 | 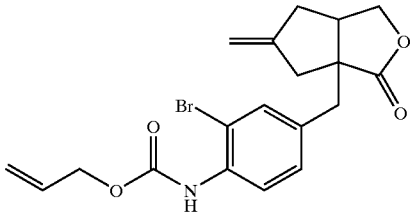 | 56 | 327 | 98 | 0.54(III, 1:1) | 423/425[M + NH4+] |
| 288 | 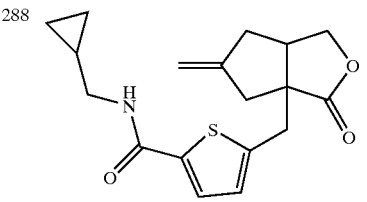 | 73 | 318 | 127 | 0.43(I, 40:1) | 332[M + H+] |
| 289 | 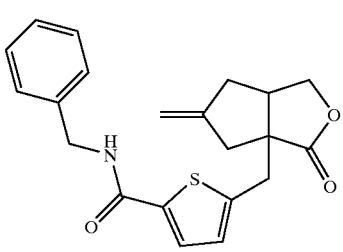 | 91 | 318 | 127 | 0.46(I, 40:1) | 368[M + H+] |

| Ex. No. | Structure | Yield % | Starting Material | Procedure analogous to Ex. | Rf | MS |
|---|---|---|---|---|---|---|
| 290 | 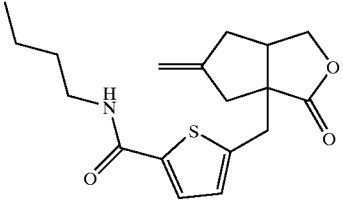 | 92 | 318 | 127 | 0.45(I, 40:1) | 334[M + H+] |
| 291 | 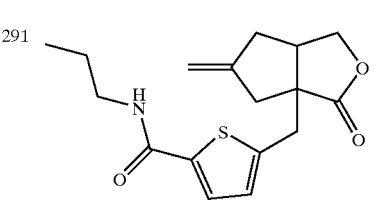 | 93 | 318 | 127 | 0.37(I, 40:1) | 320[M + H+] |
| 292 | 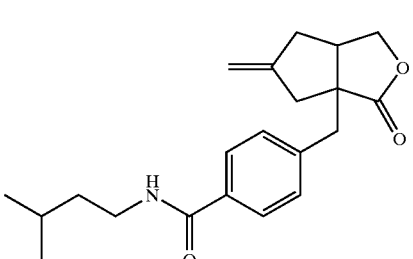 | 98 | 124 | 127 | 0.20(III, 2:1) | 383[M + H3CCN + H+] |
| 293 | 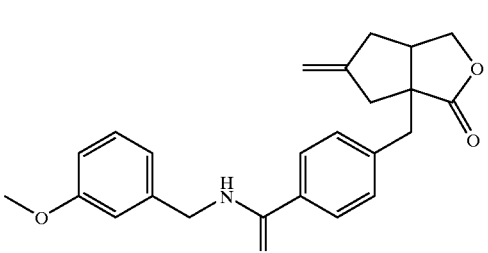 | quant. | 124 | 127 | 0.37(I, 40:1) | |
| 294 | 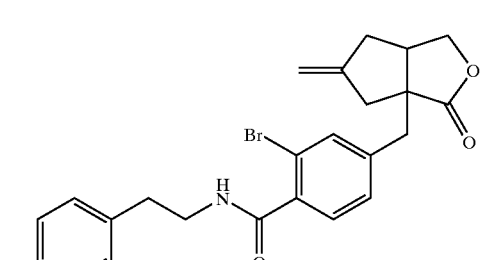 | 72 | 327 | 127 | 0.79(I, 10:1) | 509/511[M + H3CCN + H+] |
| 295 | 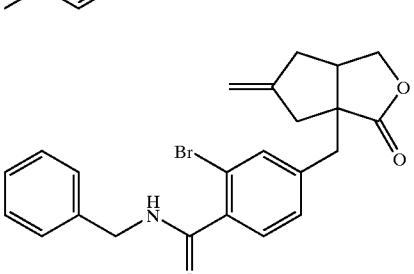 | 66 | 327 | 127 | 0.79(I, 10:1) | 481/483[M + H3CCN + H+] |

-continued

| Ex. No. | Structure | Yield % | Starting Material | Procedure analogous to Ex. | Rf | MS |
|---|---|---|---|---|---|---|
| 296 | 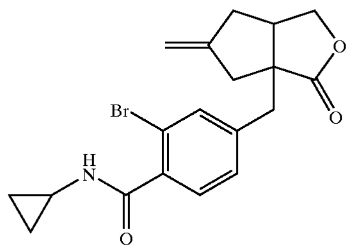 | 47 | 327 | 127 | 0.66(I, 10:1) | 421/423[M + H3CCN + H+] |
| 297 | 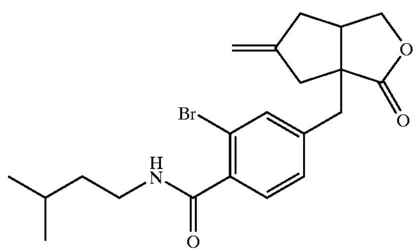 | 59 | 327 | 127 | 0.77(I, 10.1) | 459/461[M + H3CCN + H+] |
| 298 | 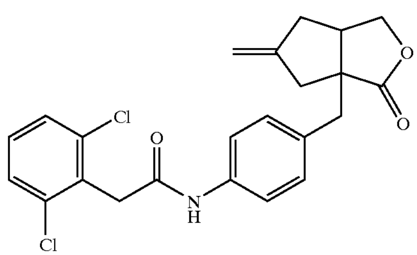 | 91 | 104 | 259 | 0.38(II, 2:1) | 430[M + H+] |
| 299 | 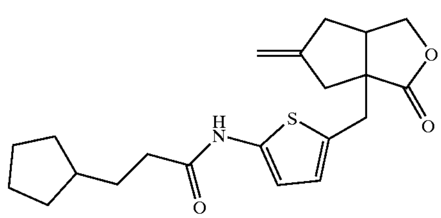 | 7 | 325 | 106 | 0.43(III, 1:1) | 374[M + H+] |
| 300 | 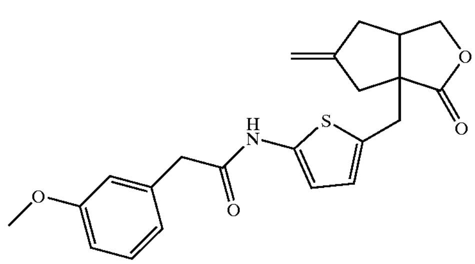 | 7 | 325 | 106 | 0.31(III, 1:1) | 398[M + H+] |
| 301 | 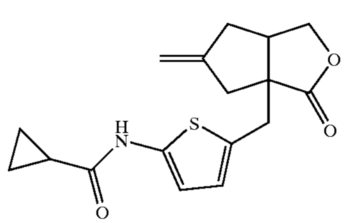 | 7 | 325 | 106 | 0.29(III, 1:1) | 318[M + H+] |

-continued

| Ex. No. | Structure | Yield % | Starting Material | Procedure analogous to Ex. | Rf | MS |
|---|---|---|---|---|---|---|
| 302 | 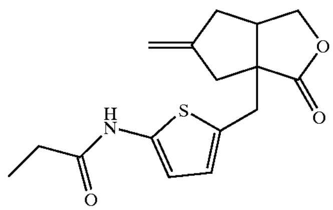 | 17 | 325 | 106 | 0.22(III, 1:1) | 306[M + H+] |
| 303 | 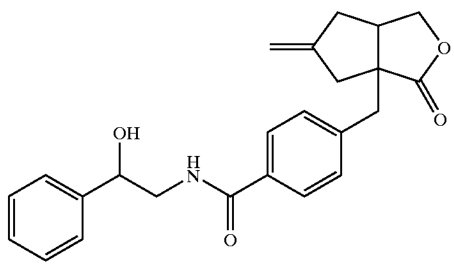 | 73 | 124 | 127 | 0.21(II, 20:1) | 392[M + H+] |
| 304 | 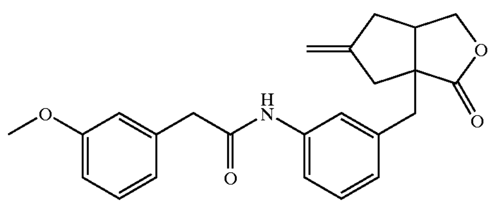 | 17 | 326 | 106 | 0.38(III, 1:1) | 392[M + H+] |
| 305 | 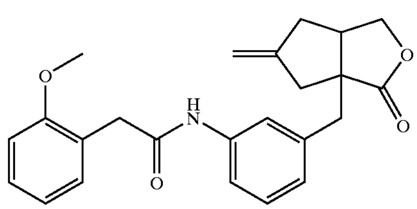 | 86 | 326 | 259 | 0.35(III, 1:1) | 392[M + H+] |
| 306 | 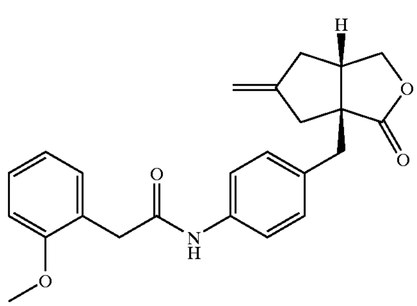 | 41 | 105 | 259 | 0.40(III, 1:1) | |
| 307 | 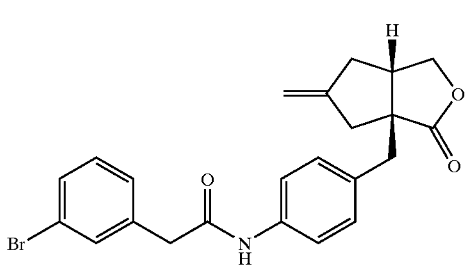 | 80 | 105 | 259 | 0.33(III, 1:1) | |

-continued

| Ex. No. | Structure | | Yield % | Starting Material | Procedure analogous to Ex. | Rf | MS |
|---|---|---|---|---|---|---|---|
| 308 | 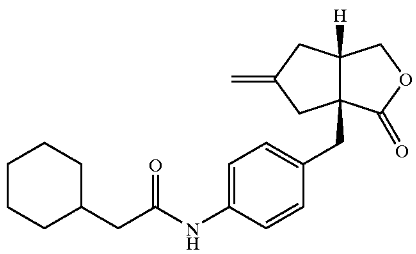 | | 53 | 105 | 259 | 0.48(III, 1:1) | |
| 309 | 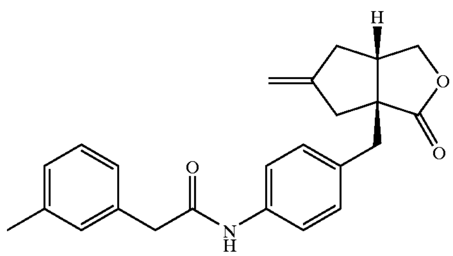 | | 64 | 105 | 259 | 0.38(III, 1:1) | |
| 310 | 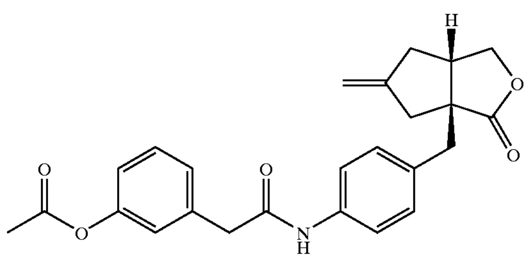 | Chiral | 18 | 105 | 259 | 0.17(III, 1:1) | 437[M + H+] |
| 311 | 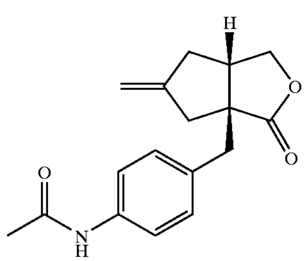 | Chiral | 33 | 105 | 259 | 0.04(III, 1:1) | |
| 312 | 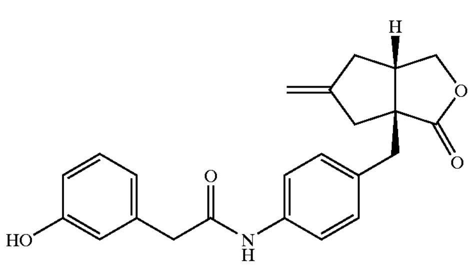 | Chiral | 95 | 310 | 261 | 0.58(I, 10:1) | 395[M + NH4+] |

-continued

| Ex. No. | Structure | Yield % | Starting Material | Procedure analogous to Ex. | Rf | MS |
|---|---|---|---|---|---|---|
| 313 | 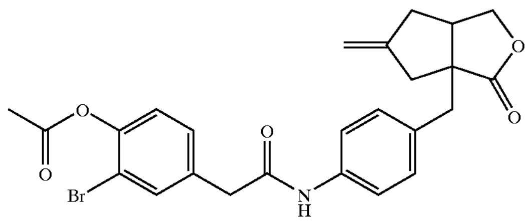 | 27 | 104 | 259 | | 498[M + H+] |
| 314 | 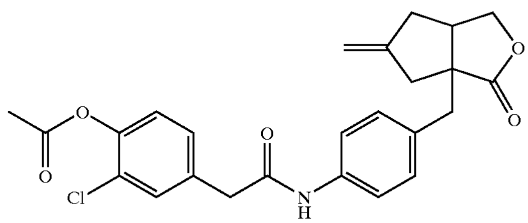 | 26 | 104 | 259 | | 453[M + H+] |
| 315 | 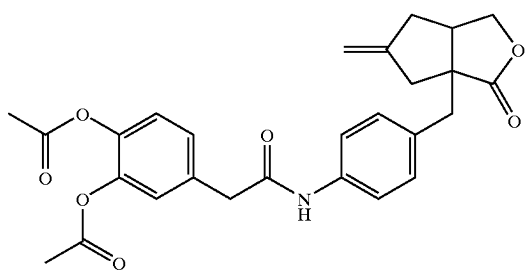 | 7 | 104 | 259 | | 478[M + H+] |
| 316 | 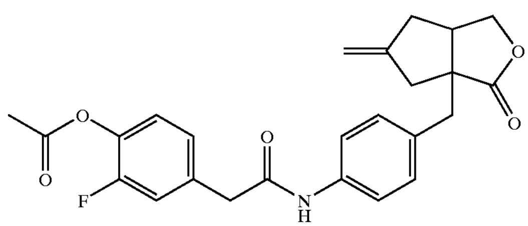 | 28 | 104 | 259 | | 438[M + H+] |
| 317 | 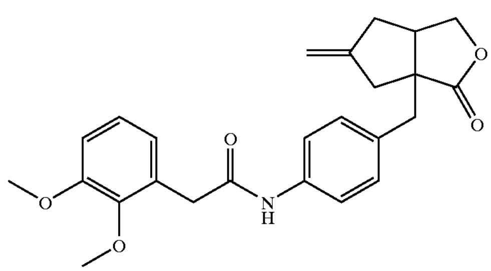 | quant. | 104 | 259 | 0.26(II, 50:1) | 422[M + H+] |
| 318 | 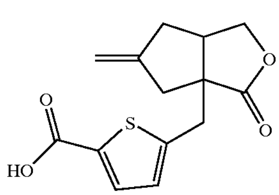 | 98 | 1A | 1(alkylation) 124(hydrolysis of the ester) | | 296[M + NH4+] |

-continued

| Ex. No. | Structure | Yield % | Starting Material | Procedure analogous to Ex. | Rf | MS |
|---|---|---|---|---|---|---|
| 319 | 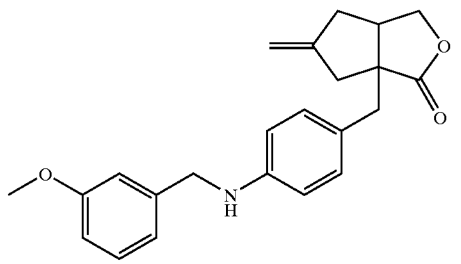 | 98 | 104 | 260 | 0.61(II, 20:1) | 405[M + H3CCN + H+] |
| 320 | 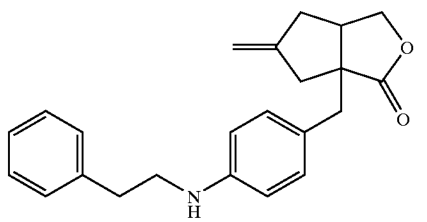 | 35 | 104 | 260 | 0.25(III, 2:1) | 389[M + H3CCN + H+] |
| 321 | 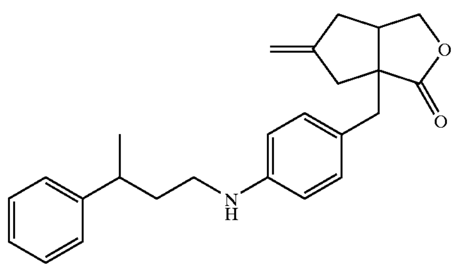 | 53 | 104 | 260 | 0.62(III, 2:1) | 376[M + H+] |
| 322 | 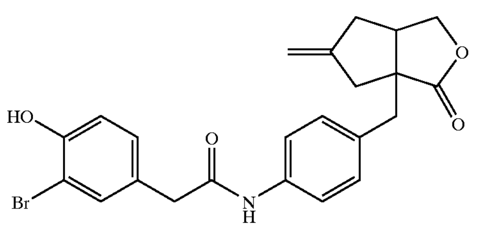 | 79 | 313 | 261 | 0.52(I, 10:1) | 456[M + H+] |
| 323 | 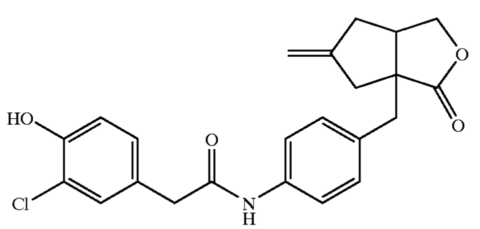 | 69 | 314 | 261 | 0.4(I, 10:1) | 454[M + H+] |
| 324 | 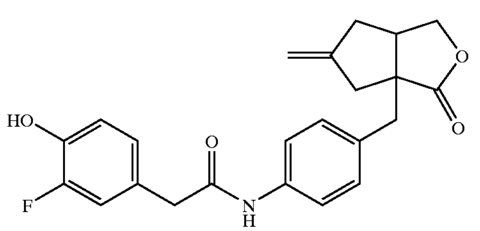 | 83 | 316 | 261 | 0.51(I, 10:1) | 437[M + H3CCN + H+] |

-continued

| Ex. No. | Structure | Yield % | Starting Material | Procedure analogous to Ex. | Rf | MS |
|---|---|---|---|---|---|---|
| 325 | 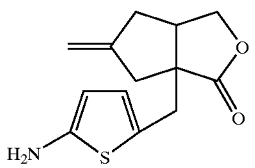 | quant. | 284 | 104 | 0.33(III, 1:1) | — |
| 326 | 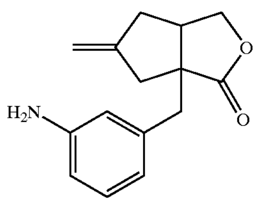 | 5 | 286 | 104 | 0.32(III, 1:1) | — |
| 327 | 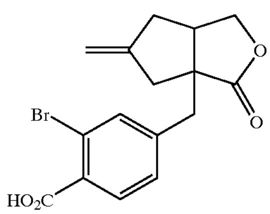 | quant. | 277 | 124 | — | 351[M + H+] |
| 328 | 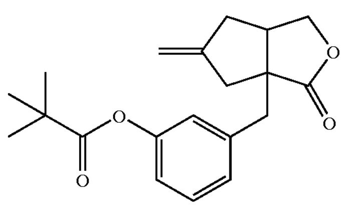 | 40 | 1A | 1 | 0.49(III, 2:1) | 346[M + NH4+] |
| 329 | 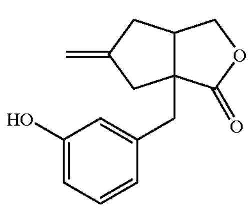 | 83 | 328 | 261 | 0.31(II, 20:1) | 262[M + NH4+] |
| 330 | 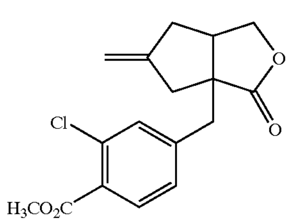 | 28 | 1A | 1 | 0.39 (CH$_2$Cl$_2$) | 321[M + NH4+] |
| 331 | 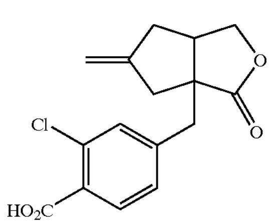 | quant. | 330 | 124 | — | 307[M + H+] |

-continued

| Ex. No. | Structure | Yield % | Starting Material | Procedure analogous to Ex. | Rf | MS |
|---|---|---|---|---|---|---|
| 332 | 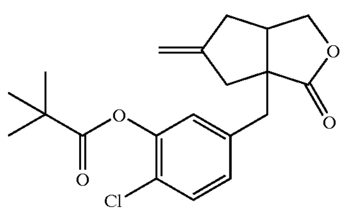 | | 1 | 1A | | |
| 333 | 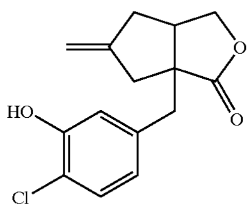 | | 332 | 261 | | |
| 334 | 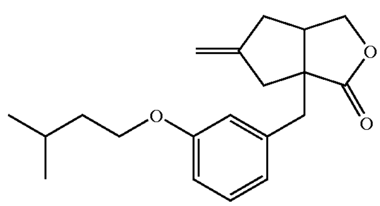 | | 329 | 262 | | |
| 335 | 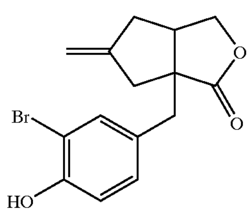 | quant. | 280 | 261 | 0.35(II, 20:1) | — |
| 336 | 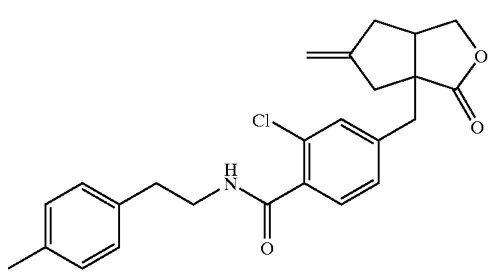 | 90 | 331 | 127 | | 465[M + H+ H3CCN]+ |
| 337 | 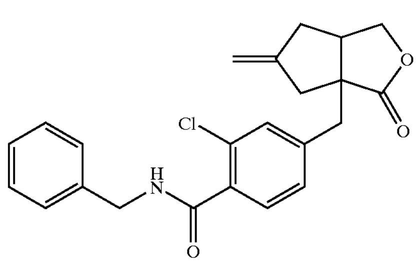 | 87 | 331 | 127 | | 437[M + H3CCN + H]+ |

-continued

| Ex. No. | Structure | Yield % | Starting Material | Procedure analogous to Ex. | Rf | MS |
|---|---|---|---|---|---|---|
| 338 | 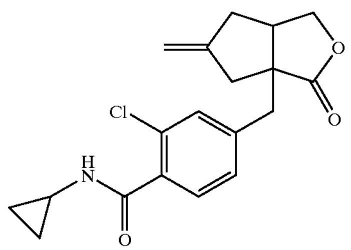 | 98 | 331 | 127 | | 387[M + H3CCN + H]+ |
| 339 | 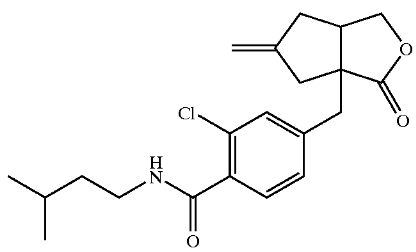 | 78 | 331 | 127 | | 417[M + H3CCN + H]+ |
| 340 | 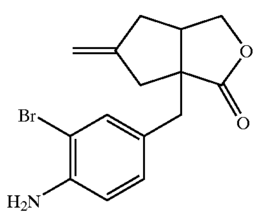 | 63 | 287 | 104 | — | 363/365[M + H3CCN + H+] |
| 341 | 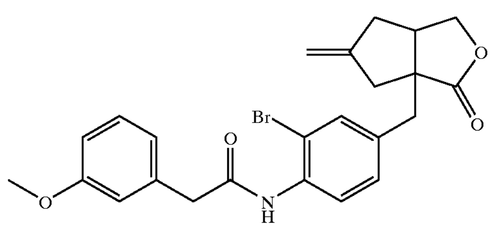 | 41 | 340 | 259 | 0.42(III, 1:1) | 487/489[M + H+] |
| 342 | 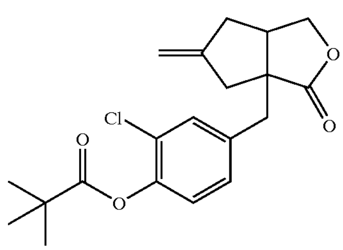 | 41 | 1A | 1 | 0.35 (CH2Cl2) | — |
| 343 | Chiral | 96 | 105 | 259 | 0.37(III, 1:1) | 422[M + H+] |

-continued
| Ex. No. | Structure | Yield % | Starting Material | Procedure analogous to Ex. | Rf | MS |
|---|---|---|---|---|---|---|
| 344 | 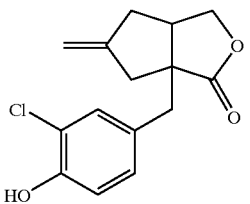 | 79 | 342 | 261 | 0.21 (CH2Cl2) | — |
The examples listed in the table below were prepared analogously to the procedure of Example 127.
| Ex. No. | Structure | Formula | Molecular weight [g/mol] | Mz + H |
|---|---|---|---|---|
| 345 | 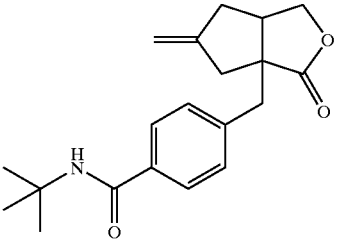 | C20 H25 N O3 | 327.4272 | 328 |
| 346 | 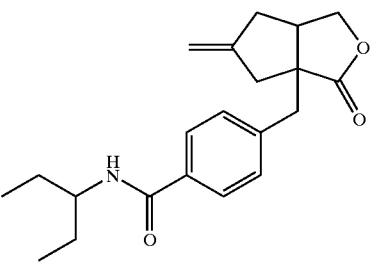 | C21 H27 N O3 | 341.4543 | 342 |
| 347 | 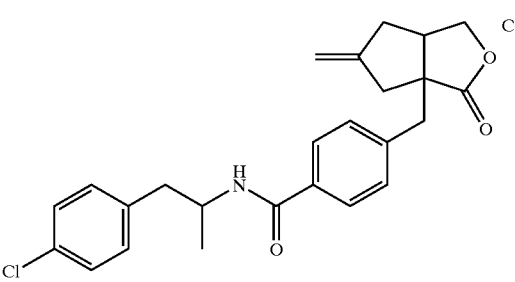 | C25 H26 Cl N O3 | 423.9439 | 424 |
| 348 | 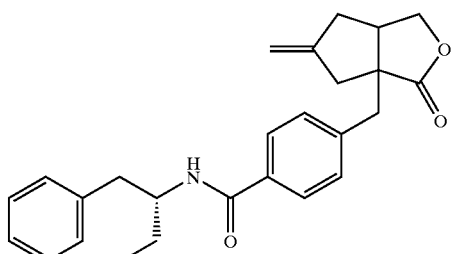 | C25 H27 N O4 | 405.4982 | 406 |

-continued

| Ex. No. | Structure | Formula | Molecular weight [g/mol] | Mz + H |
|---|---|---|---|---|
| 349 | 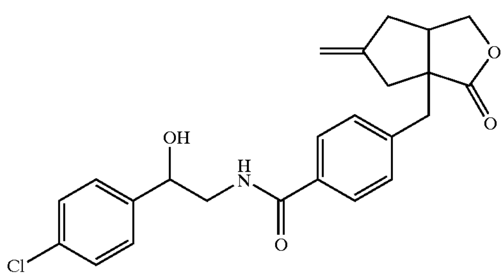 | C24 H24 Cl N O4 | 425.9162 | 426 |
| 350 | 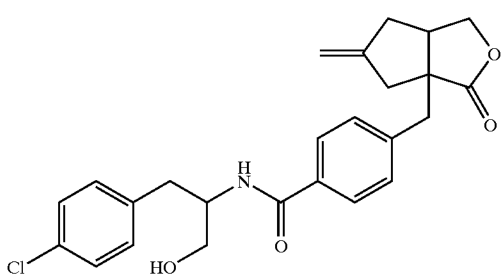 | C25 H26 Cl N O4 | 439.9433 | 440 |
| 351 | 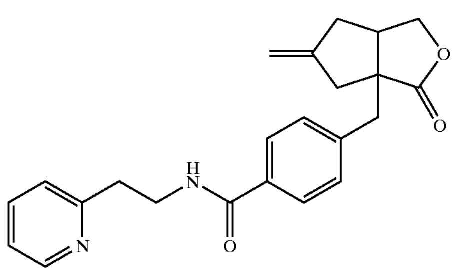 | C23 H24 N2 O3 | 376.4594 | 377 |
| 352 | 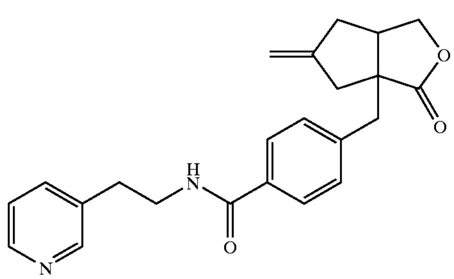 | C23 H24 N2 O3 | 376.4594 | 377 |
| 353 | 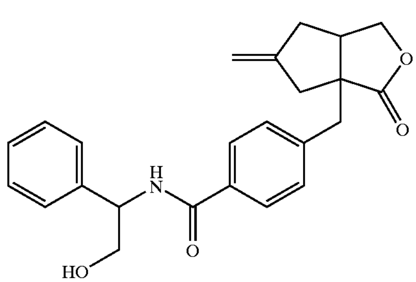 | C24 H25 N O4 | 391.4712 | 392 |

The compounds listed in the table were prepared analogously to the procedure of Example 259.

| Ex. No. | Structure | Formula | Molecular weight [g/mol] | M + H |
|---|---|---|---|---|
| 354 | 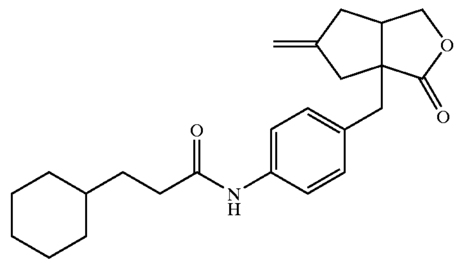 | C24H31NO3 | 381.51957 | 382 |
| 355 | Chiral | C25H27NO3 | 389.49884 | 390 |
| 356 | Chiral | C25H27NO3 | 389.49884 | 390 |
| 357 | 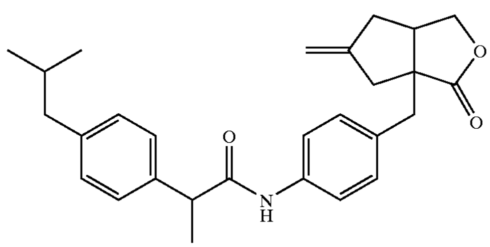 | C28H33NO3 | 431.58011 | 432 |
| 358 | 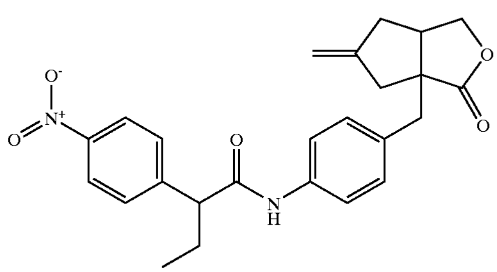 | C25H26N2O5 | 434.49637 | 435 |

-continued

| Ex. No. | Structure | Formula | Molecular weight [g/mol] | M + H |
|---|---|---|---|---|
| 359 | 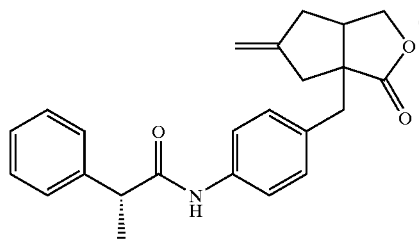 | C24H25NO3 | 375.47175 | 376 |
| 360 | 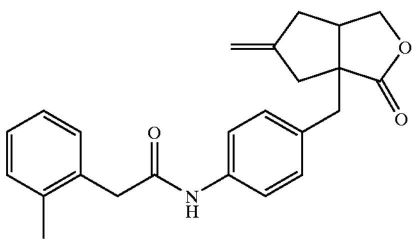 | C24H25NO3 | 375.47175 | 376 |
| 361 | 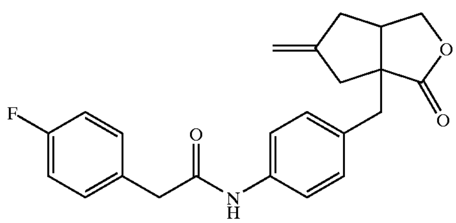 | C23H22FNO3 | 379.43509 | 380 |
| 362 | 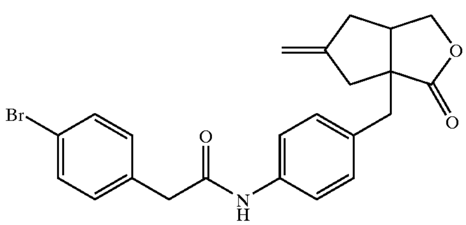 | C23H22BrNO3 | 440.34069 | 440 |
| 363 | 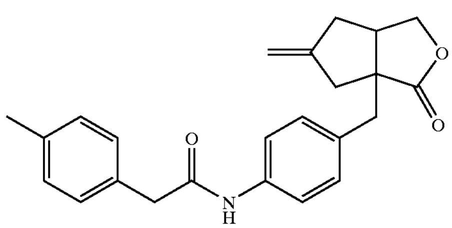 | C24H25NO3 | 375.47175 | 376 |
| 364 | 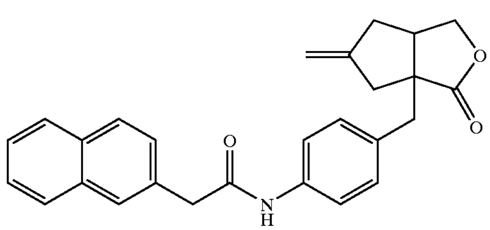 | C27H25NO3 | 411.5052 | 412 |

-continued

| Ex. No. | Structure | Formula | Molecular weight [g/mol] | M + H |
|---|---|---|---|---|
| 365 | 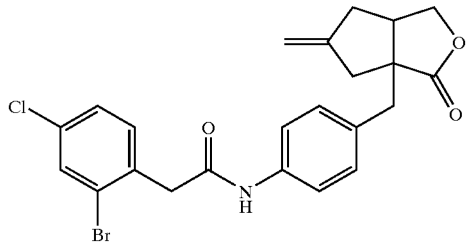 | C23H21BrClNO3 | 474.78572 | 474 |
| 366 | 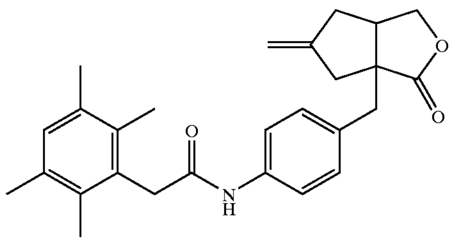 | C27H31NO3 | 417.55302 | 418 |
| 367 | 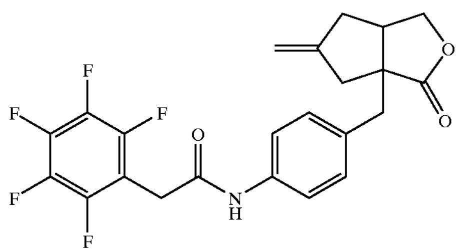 | C23H18F5NO3 | 451.39681 | 452 |
| 368 | 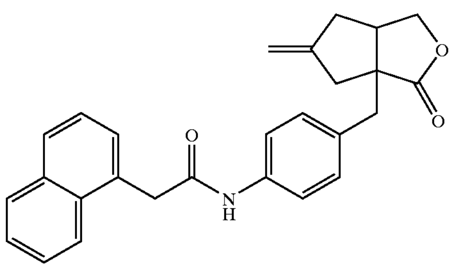 | C27H25NO3 | 411.5052 | 412 |
| 369 | 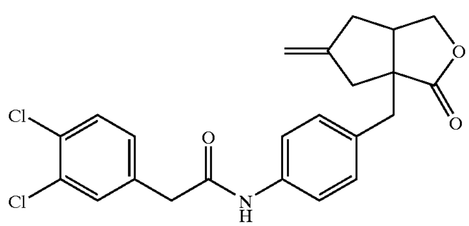 | C23H21Cl2NO3 | 430.33472 | 430 |
| 370 | 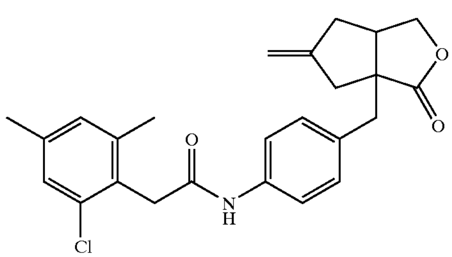 | C25H26ClNO3 | 423.94387 | 424 |

-continued

| Ex. No. | Structure | Formula | Molecular weight [g/mol] | M + H |
|---|---|---|---|---|
| 371 | 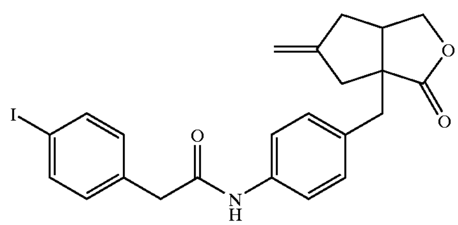 | C23H22INO3 | 487.34109 | 488 |
| 372 | 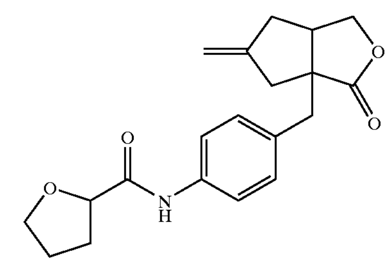 | C20H23NO4 | 341.41061 | 342 |
| 373 | 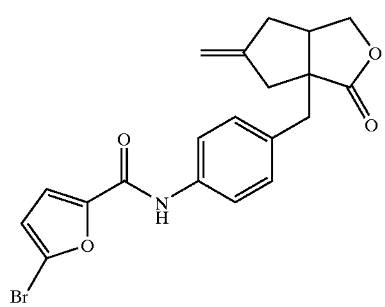 | C20H18BrNO4 | 416.27476 | 416 |
| 374 | 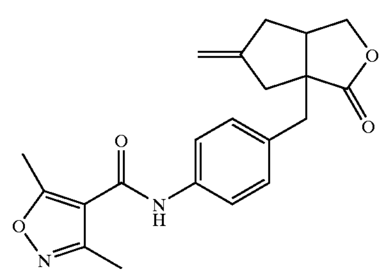 | C21H22N2O4 | 366.42049 | 367 |
| 375 | 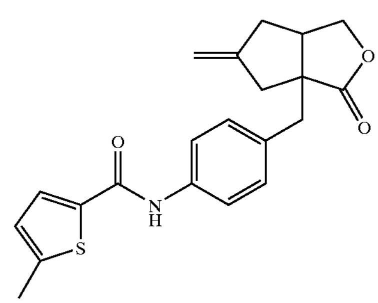 | C21H21NO3S | 367.47042 | 368 |

-continued

| Ex. No. | Structure | Formula | Molecular weight [g/mol] | M + H |
|---|---|---|---|---|
| 376 | 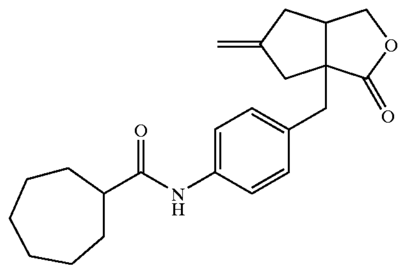 | C23H29NO3 | 367.49248 | 368 |
| 377 | 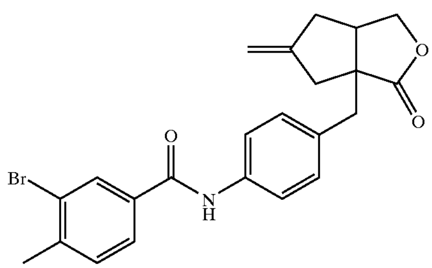 | C23H22BrNO3 | 440.34069 | 441 |
| 378 | 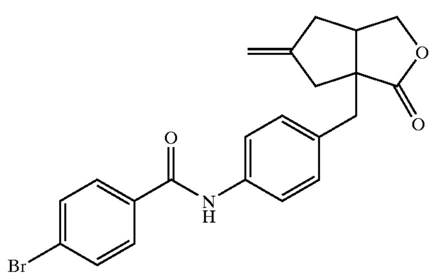 | C22H20BrNO3 | 426.3136 | 426 |
| 379 | 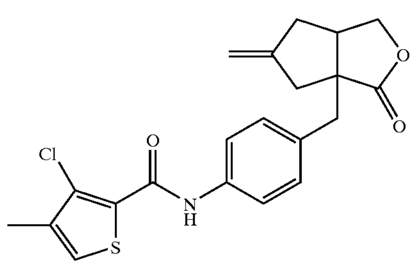 | C21H20ClNO3S | 401.91545 | 402 |
| 380 | 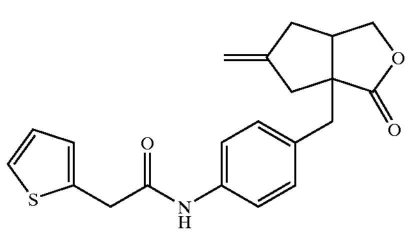 | C21H21NO3S | 367.47042 | 368 |

-continued

| Ex. No. | Structure | Formula | Molecular weight [g/mol] | M + H |
|---|---|---|---|---|
| 381 | 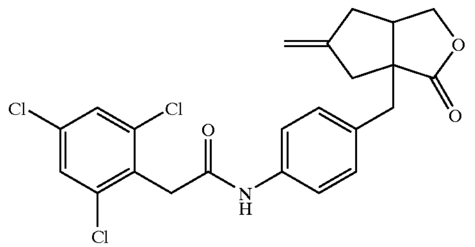 | C23H20Cl3NO3 | 464.77975 | 464 |
| 382 | 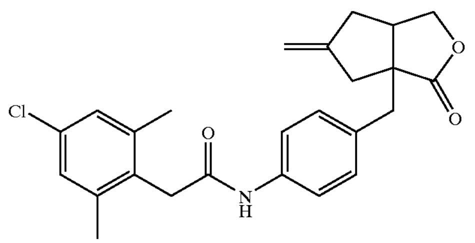 | C25H26ClNO3 | 423.94387 | 424 |
| 383 | 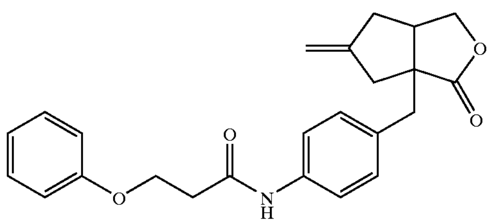 | C24H25NO4 | 391.47115 | 392 |
| 384 | 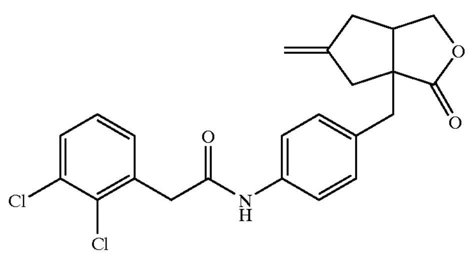 | C23H21Cl2NO3 | 430.33472 | 430 |
| 385 | 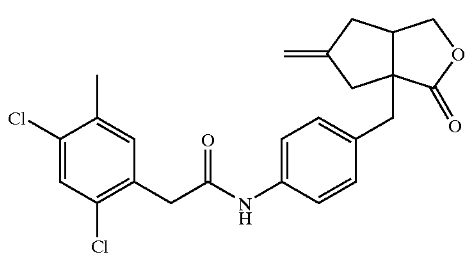 | C24H23Cl2NO3 | 444.36181 | 444 |
| 386 | 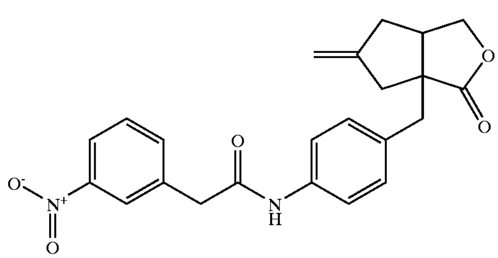 | C23H22N2O5 | 406.44219 | 407 |

-continued

| Ex. No. | Structure | Formula | Molecular weight [g/mol] | M + H |
|---|---|---|---|---|
| 387 | 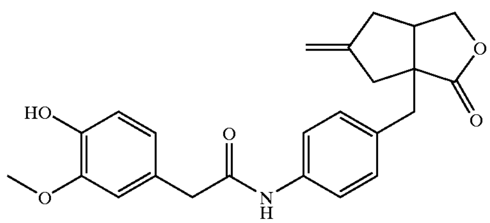 | C24H25NO5 | 407.47055 | 408 |
| 388 | 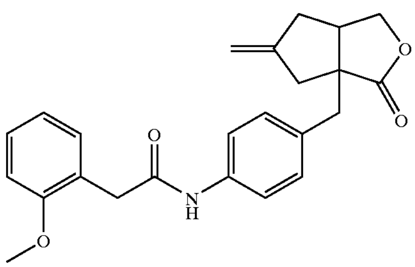 | C24H25NO4 | 391.47115 | 392 |
| 389 | 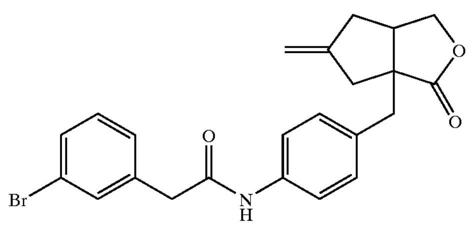 | C23H22BrNO3 | 440.34069 | 441 |
| 390 | 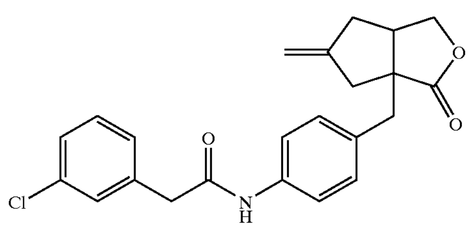 | C23H22ClNO3 | 395.88969 | 396 |
| 391 | 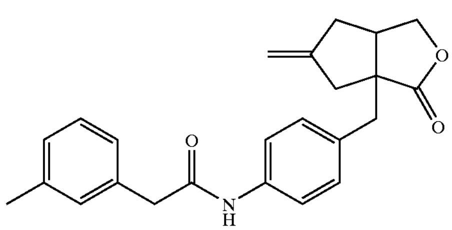 | C24H25NO3 | 375.47175 | 376 |
| 392 | 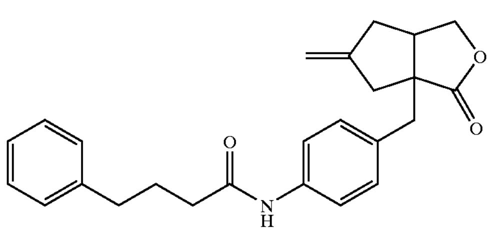 | C25H27NO3 | 389.49884 | 390 |

| Ex. No. | Structure | Formula | Molecular weight [g/mol] | M + H |
|---|---|---|---|---|
| 393 | 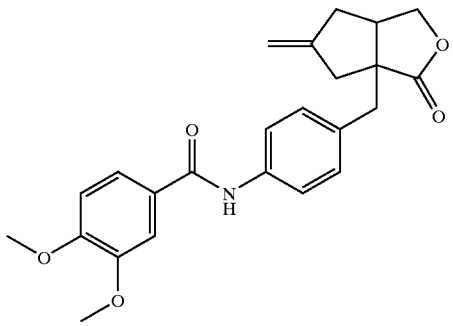 | C24H25NO5 | 407.47055 | 408 |
| 394 | 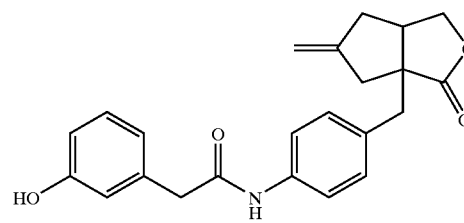 | C23H23NO4 | 377.44406 | 378 |
| 395 | 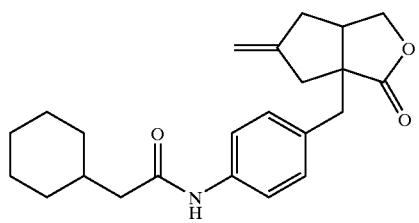 | C23H29NO3 | 367.49248 | 368 |
| 396 | 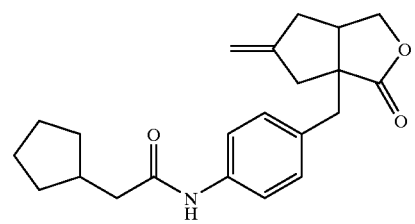 | C22H27NO3 | 353.46539 | 354 |
| 397 | 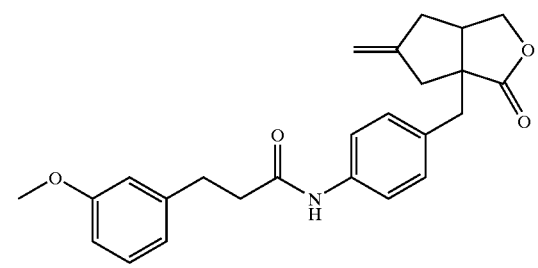 | C25H27NO4 | 405.49824 | 406 |

-continued
| Ex. No. | Structure | Formula | Molecular weight [g/mol] | M + H |
|---|---|---|---|---|
| 398 | 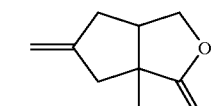 | C21H23N3O3 | 365.43576 | 366 |
| 399 | 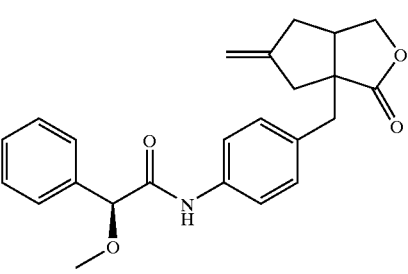 | C24H25NO4 | 391.47115 | 392 |
| 400 | 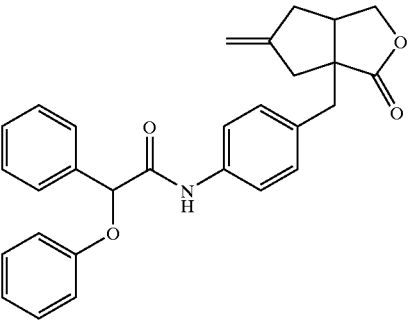 | C29H27NO4 | 453.54284 | 454 |
| 401 | 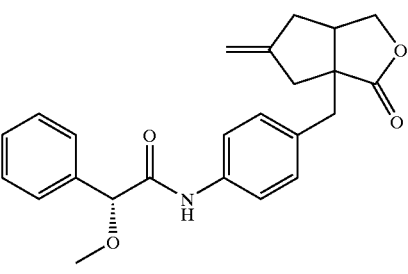 | C24H25NO4 | 391.47115 | 392 |
| 402 | 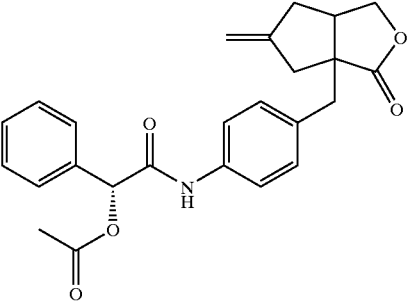 | C25H25NO5 | 419.4817 | 420 |

-continued

| Ex. No. | Structure | Formula | Molecular weight [g/mol] | M + H |
|---|---|---|---|---|
| 403 | 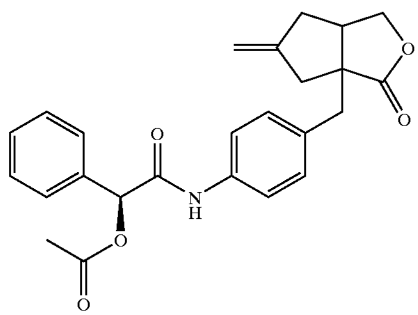 | C25H25NO5 | 419.4817 | 420 |
| 404 | 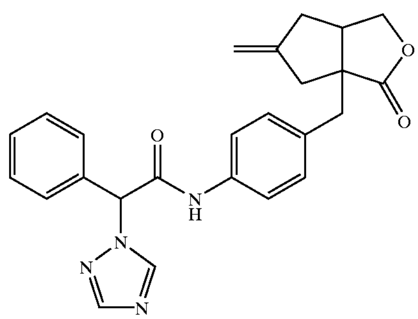 | C25H24N4O3 | 428.49503 | 429 |
| 405 | 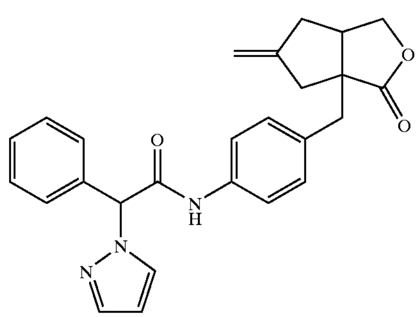 | C26H25N3O3 | 427.50745 | 428 |
| 406 | 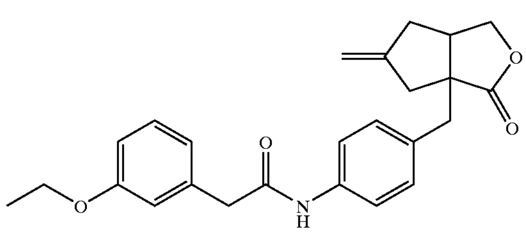 | C25H27NO4 | 405.49824 | 406 |
| 407 | 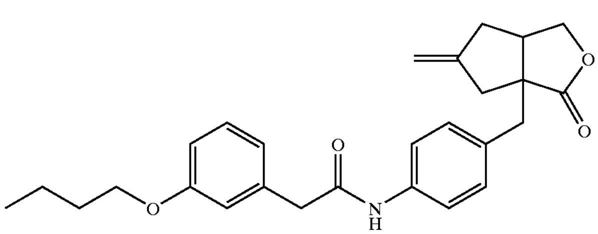 | C27H31NO4 | 433.55242 | 434 |

-continued

| Ex. No. | Structure | Formula | Molecular weight [g/mol] | M + H |
|---|---|---|---|---|
| 408 | 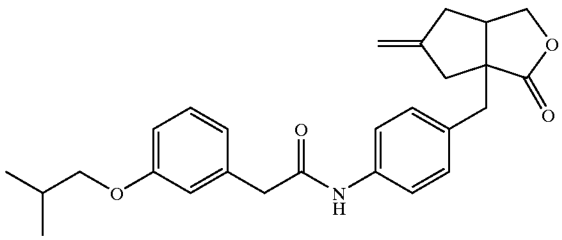 | C27H31NO4 | 433.55242 | 434 |
| 409 | 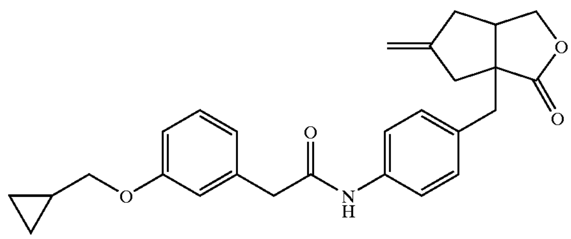 | C27H29NO4 | 431.53648 | 432 |
| 410 | 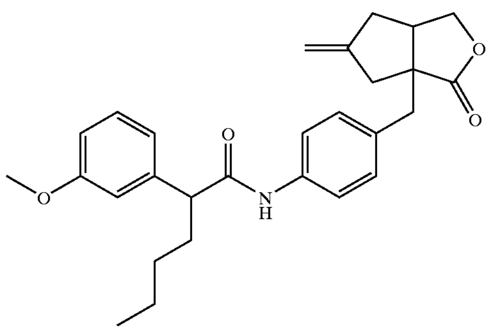 | C28H33NO4 | 447.57951 | 448 |
| 411 | 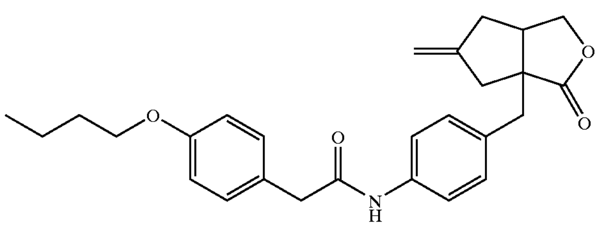 | C27H31NO4 | 433.55242 | 434 |
| 412 | 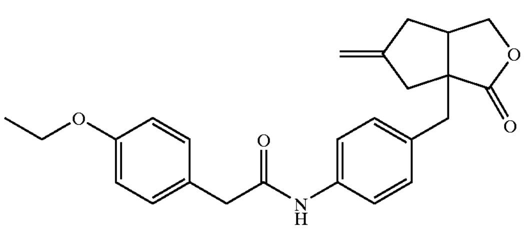 | C25H27NO4 | 405.49824 | 406 |
| 413 | 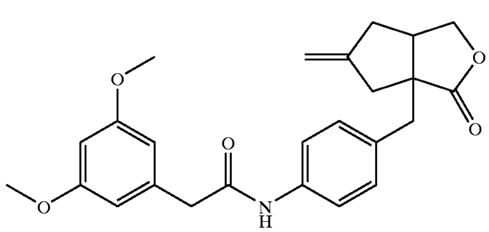 | C25H27NO5 | 421.49764 | 422 |

-continued

| Ex. No. | Structure | Formula | Molecular weight [g/mol] | M + H |
|---|---|---|---|---|
| 413a | 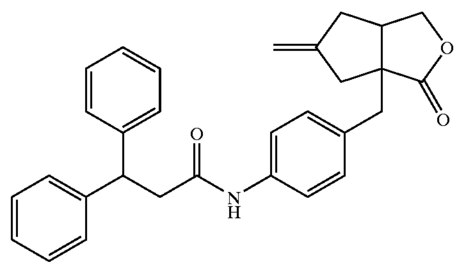 | C30H29NO3 | 451.57053 | 452 |
| 414 | 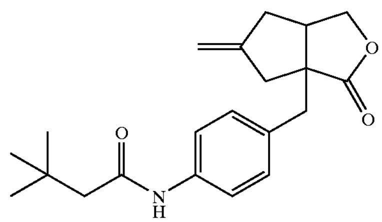 | C21H27NO3 | 341.45424 | 342 |
| 415 | 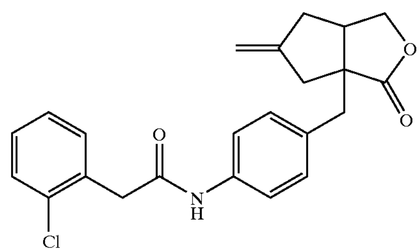 | C23H22ClNO3 | 395.8897 | 396 |
| 416 | 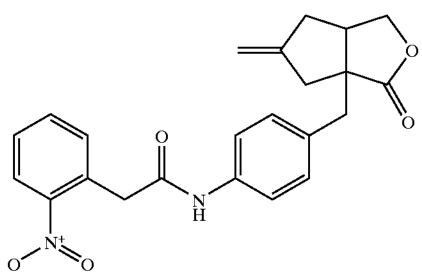 | C23H22N2O5 | 406.4422 | 407 |
| 417 | 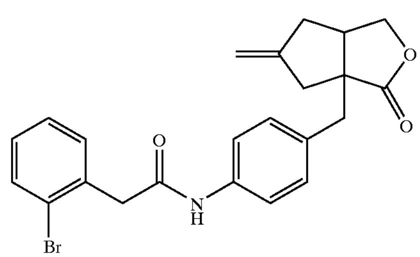 | C23H22BrNO3 | 440.3407 | 441 |
| 418 | 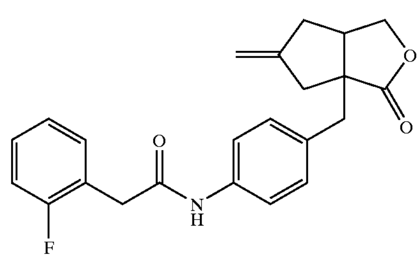 | C23H22FNO3 | 379.4352 | 380 |

-continued

| Ex. No. | Structure | Formula | Molecular weight [g/mol] | M + H |
|---|---|---|---|---|
| 419 | 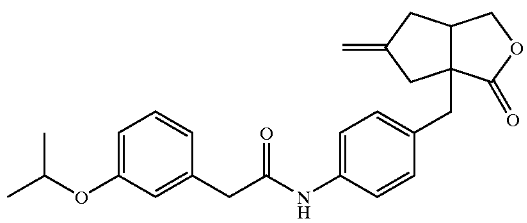 | C26 H29 N O4 | 419.5254 | 419 |
| 420 | 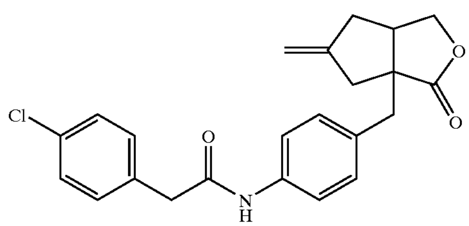 | C23H22ClNO3 | 395.8897 | 396 |
| 421 | 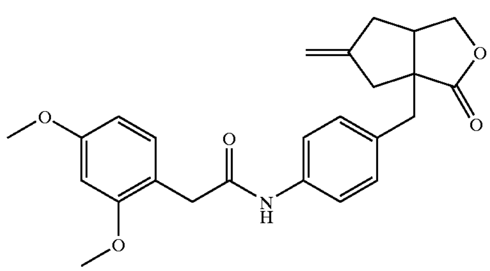 | C25 H27 N O5 | 421.4977 | 422 |
| 422 | 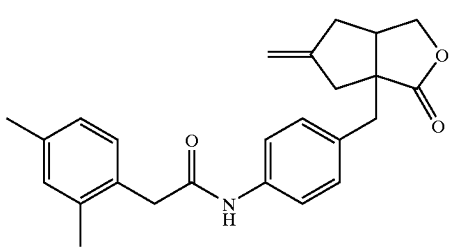 | C25 H27 N O3 | 389.4988 | 390 |
| 423 | 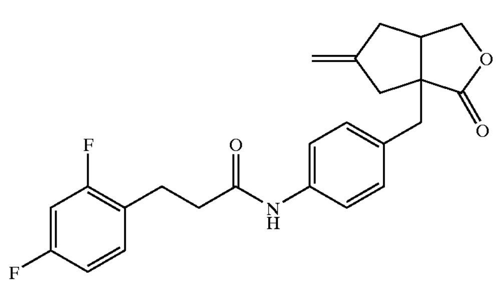 | C24H23F2NO3 | 411.4526 | 412 |
| 424 | 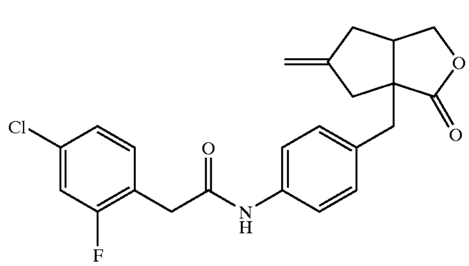 | C23H21ClFNO3 | 413.8802 | 414 |

-continued

| Ex. No. | Structure | Formula | Molecular weight [g/mol] | M + H |
|---|---|---|---|---|
| 425 | 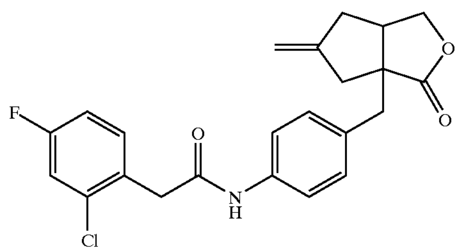 | C23H21ClFNO3 | 413.8802 | 414 |
| 426 | 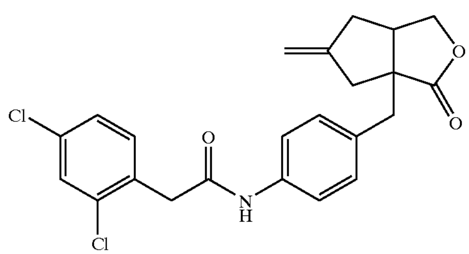 | C23H21Cl2NO3 | 430.3347 | 430 |
| 427 | 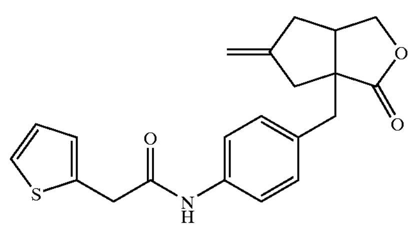 | C21H21NO3S | 367.47042 | 368 |
| 428 | 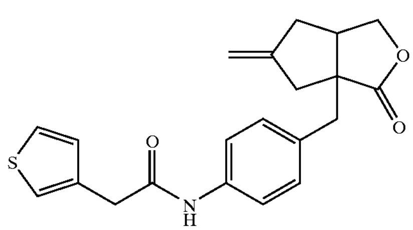 | C21 H21 N O3 S | 367.4704 | 368 |
| 429 | 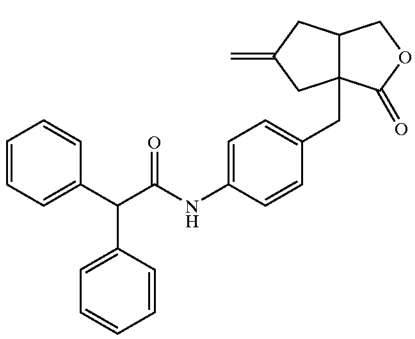 | C29 H27 N O3 | 437.5435 | 438 |
| 430 | 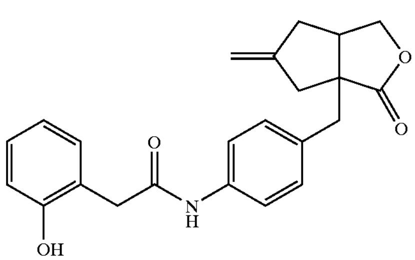 | C23 H23 N O4 | 377.4441 | 378 |

-continued

| Ex. No. | Structure | Formula | Molecular weight [g/mol] | M + H |
|---|---|---|---|---|
| 431 | 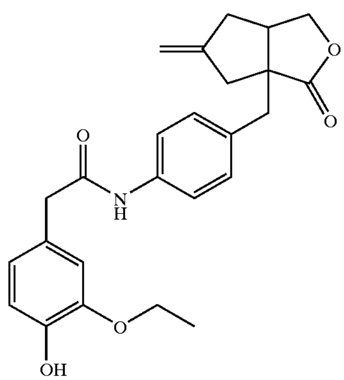 | C25 H27 N O5 | 421.4977 | 422 |
| 432 | 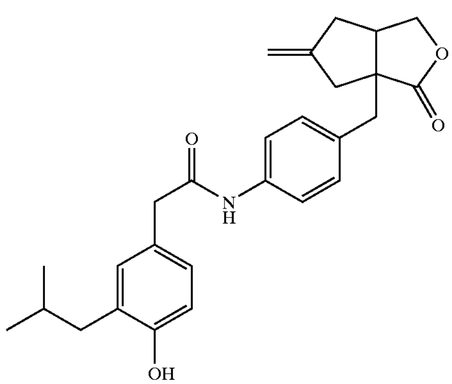 | C27H31NO4 | 433.55242 | 434 |
| 433 | 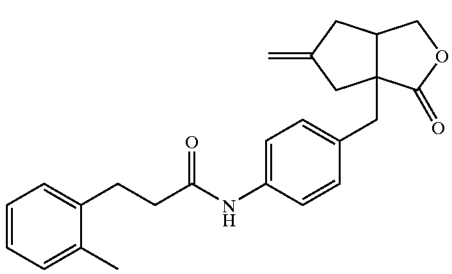 | C25 H27 N O3 | 389.4988 | 390 |
| 434 | 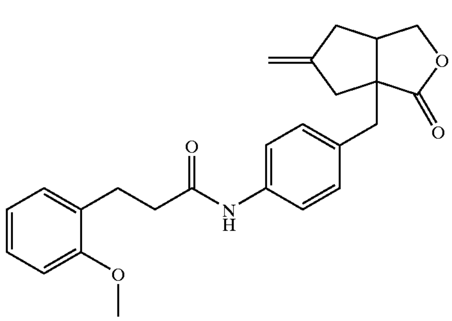 | C25 H27 N O4 | 405.4982 | 406 |

-continued

| Ex. No. | Structure | Formula | Molecular weight [g/mol] | M + H |
|---|---|---|---|---|
| 435 | 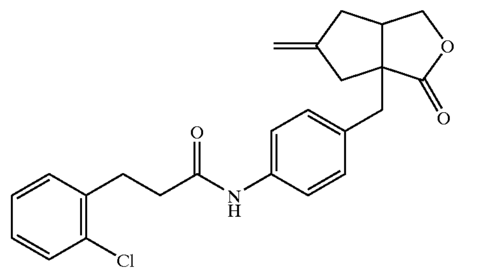 | C24H24ClNO3 | 409.9168 | 410 |
| 436 | 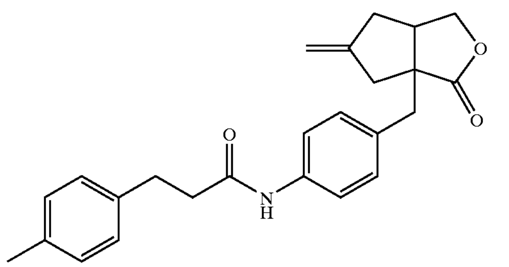 | C25H27NO3 | 389.4988 | 390 |
| 437 | 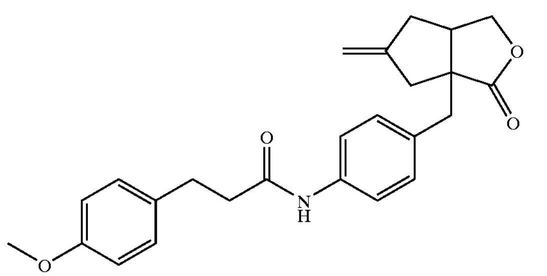 | C25 H27 N O4 | 405.4982 | 406 |
| 438 | 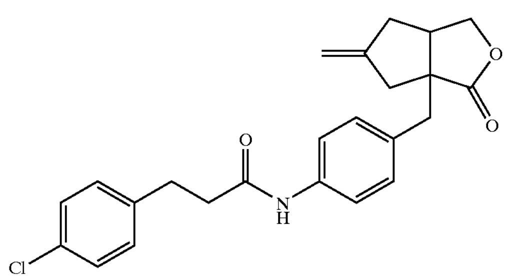 | C24H24ClNO3 | 409.9168 | 410 |
| 439 | 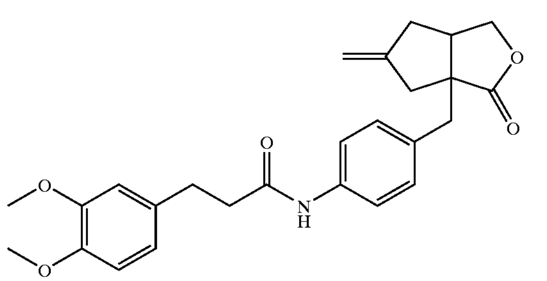 | C26 H29 N O5 | 435.5248 | 436 |

-continued

| Ex. No. | Structure | Formula | Molecular weight [g/mol] | M + H |
|---|---|---|---|---|
| 440 | 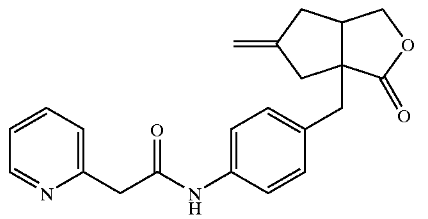 | C22 H22 N2 O3 | 362.4323 | 363 |

EXAMPLE 441

N [(3a"S*,6a"S)-4-(5-Methylidene-hexahydro-cyclopenta[c]furan-1-on6a-ylmethyl)]-phenyl-N'-(isopropyl)-urea

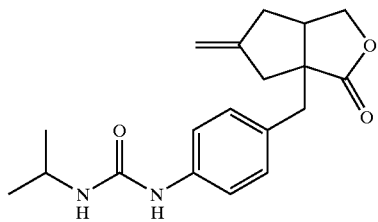

A solution of the compound from Example 104 (20 mg, 0.084 mmol) and isopropyl isocyanate (7.8 mg, 0.092 mmol) in toluene (3 ml) was stirred at room temperature for 24 hours. For work-up, ethyl acetate (3 ml), dichloromethane (2 ml) and 1 M aqueous HCl (0.6 ml) were added, the mixture was filtered through a frit filled with bituminous earth and the solvents were removed under reduced pressure.

Yield: 7.2 mg (26%)

$R_f$ (II, 2:1)=0.18

MS (ECI)=329 [M+H$^+$]

The compounds listed in the table were prepared analogously to the procedure of Example 441.

| Ex. No | Structure | Formula | Molecular weight [g/mol] | M + H |
|---|---|---|---|---|
| 442 | 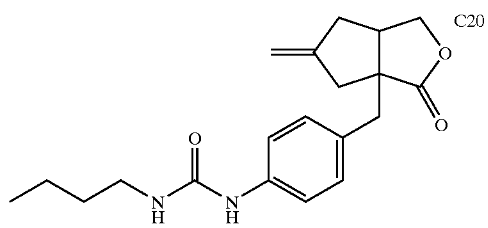 | C20 H26 N2 O3 | 342.4418 | 343 |
| 443 | 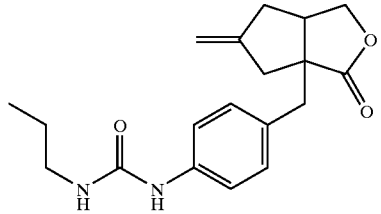 | C19 H24 N2 O3 | 328.4147 | 329 |

-continued

| Ex. No | Structure | Formula | Molecular weight [g/mol] | M + H |
|---|---|---|---|---|
| 444 | 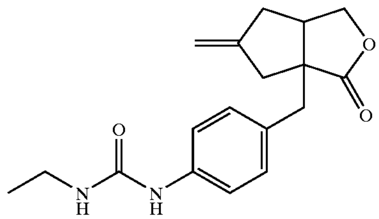 | C18 H22 N2 O3 | 314.3877 | 315 |

The compounds listed in the table below were prepared analogously to the procedure of Example 262.

| Ex. No. | Structure | Formula | Molecular weight [g/mol] | M + H |
|---|---|---|---|---|
| 445 | 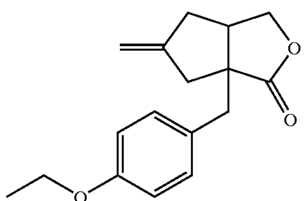 | C17 H20 O3 | 272.3472 | 273 |
| 446 | 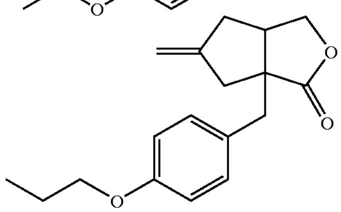 | C18 H22 O3 | 286.3743 | 287 |
| 447 | 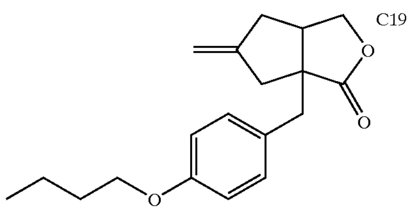 | C19 H24 O3 | 300.4013 | 301 |

The compounds listed in the table were prepared analogously to the procedure of Example 262, starting from Example 335.

| Ex. No. | Structure | Formula | Molecular weight [g/mol] | Mz |
|---|---|---|---|---|
| 448 | 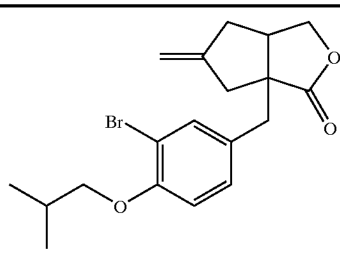 | C19 H23 Br O3 | 379.2974 | 378 |

-continued

| Ex. No. | Structure | Formula | Molecular weight [g/mol] | Mz |
|---|---|---|---|---|
| 449 | 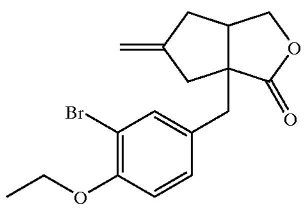 | C17H19BrO3 | 351.24318 | 350 |
| 450 | 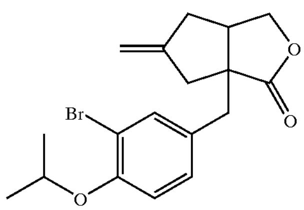 | C18H21BrO3 | 365.27027 | 364 |
| 451 | 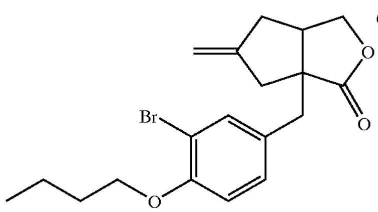 | C19H23BrO3 | 379.29736 | 378 |

The compounds listed in the table were prepared analogously to the procedure of Example 262, starting from Example 344.

| Ex. No. | Structure | Formula | Molecular weight [g/mol] | M + H |
|---|---|---|---|---|
| 452 | 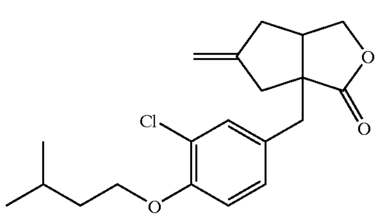 | | 348.8735 | 349.1 |
| 453 | 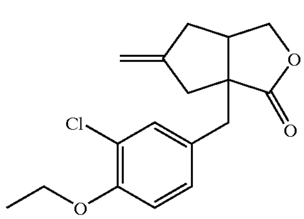 | | 306.7922 | 307.1 |

-continued

| Ex. No. | Structure | Formula | Molecular weight [g/mol] | M + H |
|---|---|---|---|---|
| 454 | 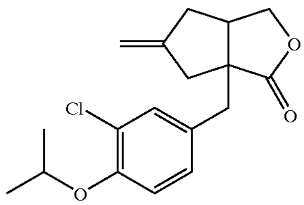 | | 320.8193 | 321.1 |
| 455 | 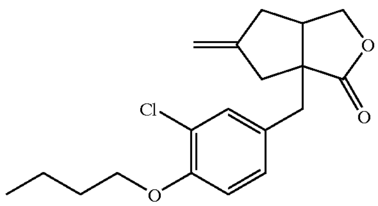 | | 334.8464 | 335.1 |

The compounds listed in the table were prepared analogously to the procedure of Example 262, starting from Example 329.

| Ex. No. | Structure | Formula | Molecular weight [g/mol] | M + H |
|---|---|---|---|---|
| 456 | 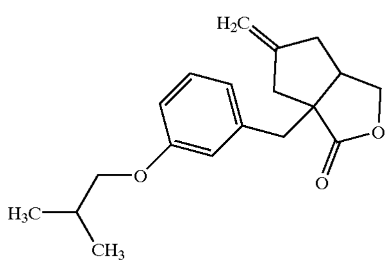 | C19H24O3 | 300.401 | 301 |
| 457 | 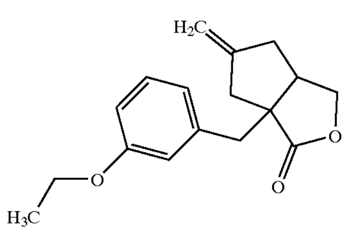 | C17H20O3 | 272.347 | 273 |
| 458 | 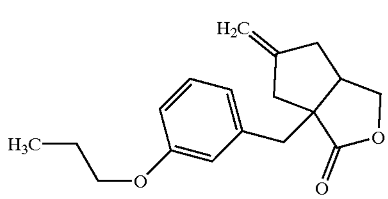 | C18H22O3 | 286.374 | 287 |

-continued

| Ex. No. | Structure | Formula | Molecular weight [g/mol] | M + H |
|---|---|---|---|---|
| 459 | 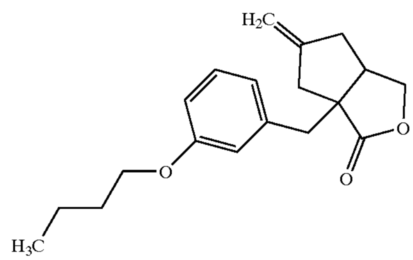 | C19H24O3 | 300.401 | 301 |

The compounds listed in the table were prepared analogously to the procedures of Example 260.

| Ex. No. | Structure | Starting material Ex. No. | Yield [%] | Rf (Cyclohexane/ ethyl acetate 3:1) | MS (CI) [M+ + 1] |
|---|---|---|---|---|---|
| 460 | 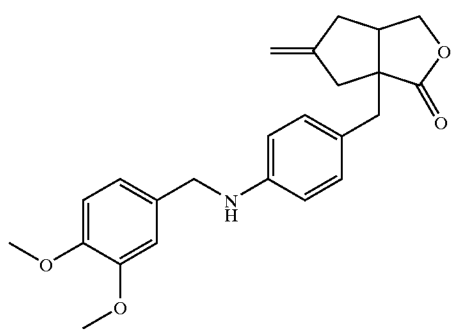 | 104 | | 0.16 | 394 |
| 461 | 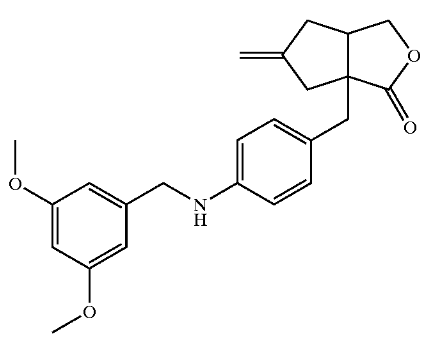 | 104 | | 0.29 | 394 |
| 462 | 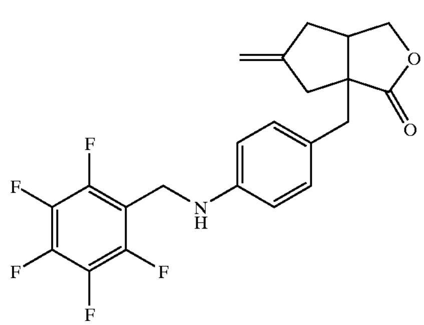 | 104 | | 0.13 | 424 |

-continued

| Ex. No. | Structure | Starting material Ex. No. | Yield [%] | Rf (Cyclohexane/ ethyl acetate 3:1) | MS (CI) [M+ + 1] |
|---|---|---|---|---|---|
| 463 | 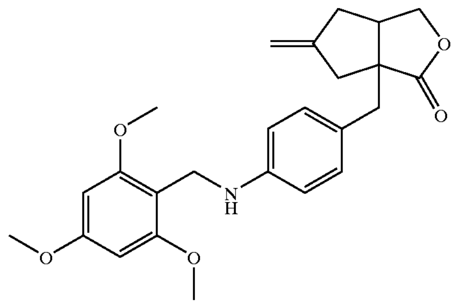 | 104 | | 0.24 | 424 |

EXAMPLE 464

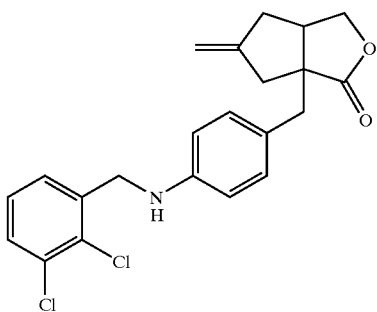

At 0° C., a solution of 60 µl of 3 M sulphuric acid and 40 mg (0.23 mmol) of 2,3-dichlorobenzaldehyde in 400 µl of THF is slowly added to an open flask with 49 mg (0.2 mmol) of the compound from Example 104, dissolved in 1 ml of THF and 350 µl of methanol. After 5 minutes, 14 mg of sodium borohydride are added, at 0° C., to the solution, which is stirred well. The mixture is stirred at room temperature for another 10 minutes.

For work-up, the batch is diluted with 400 µl of water, made alkaline, with ice-cooling, using solid NaOH, and immediately extracted with MTB ether. The combined ether phases are washed with saturated sodium chloride solution, dried over magnesium sulphate, filtered and concentrated. Purification is carried out by column chromatography (mobile phase: cyclohexane:ethyl acetate 3:1).

Yield: 2.4 mg (3.0%)

$R_f$: 0.40 (cyclohexane:ethyl acetate 3:1)

MS (EI): m/e=401 [M+]

| Ex. No. | Structure | Yield (%) | Starting Material | Procedure analogous to Example | Rf (Cyclohexane:ethyl acetate 3:1) | MS (EI: M+; CI: M + H+) |
|---|---|---|---|---|---|---|
| 465 | 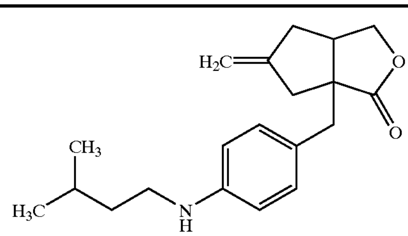 | 40.7 | 104 | 464 | 0.52 | 313 (EI) |
| 466 | 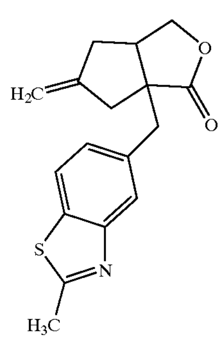 | 3.5 | 1A | 1 | 0.19 | 299 (EI) |

-continued

| Ex. No. | Structure | Yield (%) | Starting Material | Procedure analogous to Example | Rf (Cyclo-hexane:ethyl acetate 3:1) | MS (EI: M+; CI: M + H+) |
|---|---|---|---|---|---|---|
| 467 | 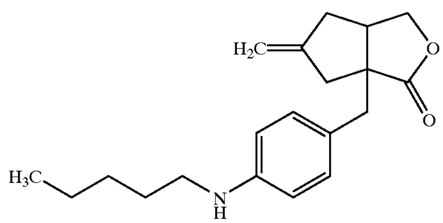 | 16 | 104 | 464 | 0.5 | 313 (EI) |
| 468 | 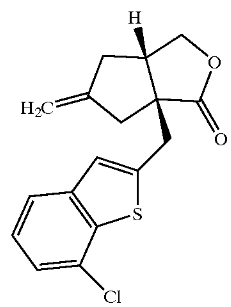 | 8.1 | 1A | 1 | 0.52 | 318 (EI) |
| 469 | 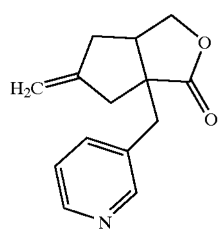 | 3.1 | 1A | 1 | 0.14 (1:1) | 229 (EI) |
| 470 | 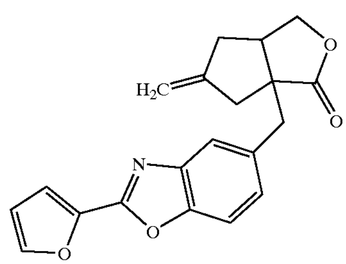 | 35.6 | 1A | 1 | 0.3 | — |
| 471 | 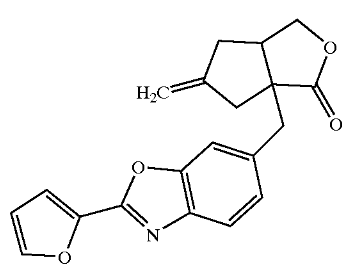 | 21.5 | 1A | 1 | 0.31 | 353 (CI) [M + NH4+] |

-continued

| Ex. No. | Structure | Yield (%) | Starting Material | Procedure analogous to Example | Rf (Cyclo-hexane:ethyl acetate 3:1) | MS (EI: M$^+$; CI: M + H$^+$) |
|---|---|---|---|---|---|---|
| 472 | 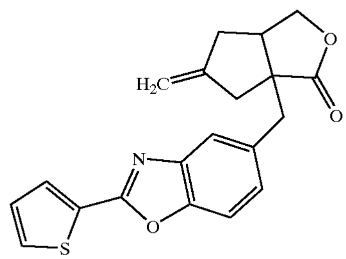 | 3.1 | 1A | 1 | 0.21 | 352 (CI) |
| 473 | 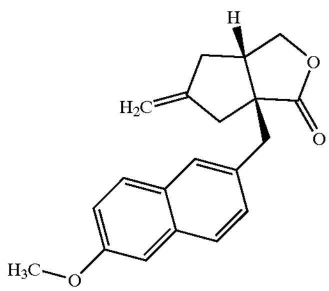 | 24.1 | 2A | 1 | 0.38 | 309 (CI) |
| 474 | 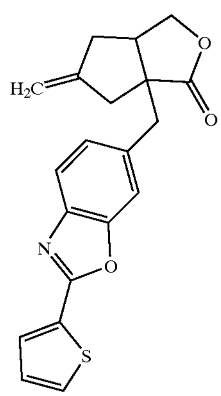 | 18.4 | 1A | 1 | 0.31 | 351 (EI) |
| 475 | 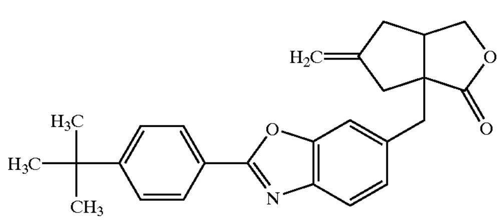 | 14.7 | 1A | 1 | 0.4 | 402 (CI) |
| 476 | 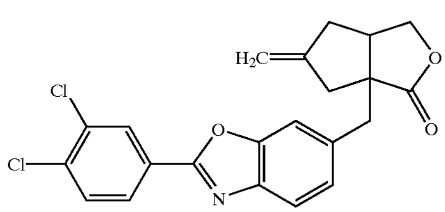 | 0.8 | 1A | 1 | 0.43 | — |

The examples listed in the table below were prepared analogously to the procedure of Example 127:

| Ex. No. | Structure | Formula | Molecular weight (g/mol) | Mz + H |
|---|---|---|---|---|
| 477 | 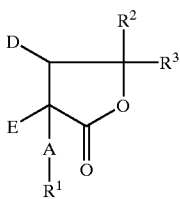 | C22 H20 Cl N O3 | 381.8626 | 382 |
| 478 | 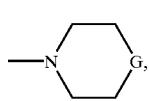 | C22 H20 Cl N O3 | 381.8626 | 382 |

What is claimed is:
1. Compounds of the general formula (I)

(I)

in which
A represents radicals of the formulae —CH$_2$—, —CO—, —CR$^4$(OH)— or —(CH$_2$)$_a$—CHR$^5$—,
in which
a represents a number 0, 1, 2, 3 or 4,
R$^4$ represents hydrogen or (C$_1$–C$_6$)-alkyl
and
R$^5$ represents phenyl,
or
represents (C$_2$–C$_8$)-alkanediyl, (C$_2$–C$_6$)-alkenediyl or (C$_2$–C$_6$)-alkinediyl,
R$^1$ is a morpholine ring attached to A via the nitrogen atom,
wherein said ring systems is optionally mono- to polysubstituted by identical or different substituents selected from the group consisting of halogen, cyano, nitro, trifluoromethyl, hydroxyl, (C$_1$–C$_6$)-alkoxy, (C$_1$–C$_6$)-alkyl-carbonyl and (C$_3$–C$_6$)-cycloalkyl, phenyl, phenoxy, benzyloxy and a 5- to 6-membered aromatic heterocycle having up to 3 heteroatoms from the group consisting of S, N and/or O, which for their part may be substituted up to three times by identical or different substituents from the group consisting of cyano and halogen, and/or are substituted by (C$_1$–C$_6$)-alkyl and (C$_2$–C$_6$)-alkylene, which for their part may be substituted by halogen, (C$_6$–C$_{10}$)-aryl or by radicals of the formula SR$^8$, —OR$^9$ or —NR$^{10}$R$^{11}$ or in which
R$^8$ represents (C$_1$–C$_6$)-alkyl or phenyl,
R$^9$ represents hydrogen or (C$_1$–C$_6$)-alkyl,
and
R$^{10}$ and R$^{11}$ are identical or different and represent hydrogen, phenyl or (C$_1$–C$_6$)-alkyl, which is optionally substituted by phenyl, which for its part may be mono- to polysubstituted by identical or different substituents from the group consisting of halogen, nitro, hydroxyl and (C$_1$–C$_6$)-alkoxy,
or
R$^{10}$ and R$^{11}$ together with the nitrogen atom form a radical of the formula in which
G represents an oxygen atom, a —CH$_2$— group or a radical of the formula —NR$^{12}$—,
in which
R 12 represents hydrogen, phenyl, benzyl, (C$_1$–C$_6$)-alkyl, (C$_1$–C$_6$)-alkoxy-carbonyl or a 5- to 6-membered aromatic heterocycle having up to 3 heteroatoms from the group consisting of S, N and/or O, and/or are substituted by groups of the formulae —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$, in which R$^{13}$ represents hydrogen, or represents (C$_1$–C$_9$)-alkyl or (C$_2$–C$_6$)-alkenyl, which for their part may be substituted by radicals of the formulae

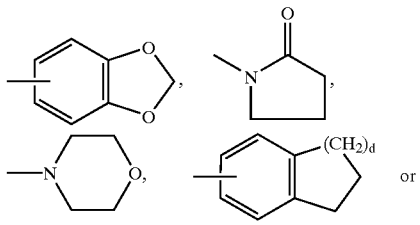

(C$_6$–C$_{10}$)-aryl or by a 5- to 7-membered aromatic heterocycle having up to 3 heteroatoms from the group consisting of S, N and/or O, in which d represents a number 1 or 2, or represents (C$_6$–C$_{10}$)-aryl, which is optionally substituted by phenyl, which for its part may be substituted by cyano or halogen, R$^{14}$ and R$^{15}$ are identical or different and represent hydrogen, (C$_3$–C$_6$)-cycloalkyl, phenyl or (C$_1$–C$_6$)-alkyl, which is optionally substituted by (C$_3$–C$_6$)-cycloalkyl or phenyl, which for its part may be mono- to polysubstituted by identical or different substituents from the group consisting of halogen, hydroxyl or (C$_1$–C$_6$)-alkoxy, R$^{16}$ represents hydrogen or (C$_1$–C$_6$)-alkyl, R$^{17}$ represents hydrogen, adamantyl, (C$_3$–C$_8$)-cycloalkyl, (C$_2$–C$_6$)-alkenyl or (C$_1$–C$_{12}$)-alkyl which is optionally substituted by adamantyl, (C$_3$–C$_6$)-cycloalkyl, (C$_6$–C$_{10}$)-aryl, phenoxy or a 5- to 6-membered aromatic heterocycle having up to 4 heteroatoms from the group consisting of S, N and/or O, where aryl and the heterocycle for their part may be mono- to polysubstituted by identical or different substituents from the group consisting of (C$_1$–C$_6$)-alkyl, (C$_1$–C$_6$)-alkoxy, hydroxyl, nitro or halogen, and/or alkyl is optionally substituted by a radical of the formula

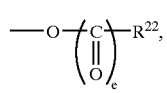

in which e represents a number 0 or 1 and

R$^{22}$ represents (C$_1$–C$_6$)-alkyl or (C$_1$–C$_{10}$)-aryl, which is optionally mono- to polysubstituted by identical or different substituents from the group consisting of halogen, nitro, hydroxyl and (C$_1$–C$_6$)-alkoxy, or represents (C$_6$–C$_{10}$)-aryl or a 5- to 6-membered aromatic heterocycle having up to 3 heteroatoms from the group consisting of S, N and/or O, which for their part may optionally be mono- to polysubstituted by identical or different substituents from the group consisting of (C$_1$–C$_6$)-alkoxy, (C$_1$–C$_6$)-alkyl, hydroxyl, nitro and halogen, or represents a radical of the formula

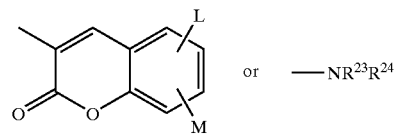

in which

L and M are identical or different and represent hydrogen or halogen,

R$^{23}$ and R$^{24}$ have the meaning of R$^{10}$ and R$^{11}$ given above,

R$^{18}$ has the meaning of R$^{16}$ given above,

R$^{19}$ represents (C$_3$–C$_8$)-cycloalkyl, or represents (C$_1$–C$_8$)-alkyl or (C$_2$–C$_8$)-alkenyl, which for their part are optionally substituted by substituents selected from the group consisting of halogen, phenyl, hydroxyl, morpholinyl, (C$_3$–C$_8$)-cycloalkyl and by a group of the formula —SiR$^{25}$R$^{26}$R$^{27}$, in which R$^{25}$, R$^{26}$ and R$^{27}$ are identical or different and represent (C$_1$–C$_6$)-alkyl, R$^{20}$ and R$^{21}$ are identical or different and represent hydrogen, adamantyl, (C$_3$–C$_8$)-cycloalkyl, phenyl, phenoxy-substituted phenyl or a 5- to 6-membered, aromatic heterocycle having up to 3 heteroatoms from the group consisting of S, N and/or O, or represent (C$_2$–C$_8$)-alkenyl, (C$_1$–C$_{12}$)-alkyl or (C$_2$–C$_6$)-alkinyl, which are optionally substituted by hydroxyl, (C$_3$–C$_6$)-cycloalkyl, (C$_1$–C$_6$)-alkoxy, halogen, hydroxyl, trifluoromethyl, phenyl or by a 5- to 6-membered aromatic heterocycle having up to 3 heteroatoms from the group consisting of S, N and/or O, where the ring systems are optionally substiutted up to 2 times by identical or different substituents from the group consisting of (C$_1$–C$_6$)-alkoxy, (C$_1$–C$_6$)-alkoxycarbonyl, halogen, phenoxy, hydroxyl and (C$_1$–C$_6$)-alkyl, and/or the alkyl listed under R$^{20}$/R$^{21}$ is optionally substituted by radicals of the formulae

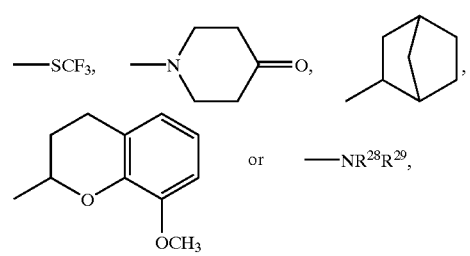

in which

R$^{28}$ and R$^{29}$ are identical or different and represent hydrogen or (C$_1$–C$_6$)-alkyl, or
represents a radical of the formula

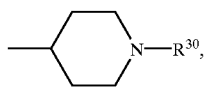

in which
R$^{30}$ has the meaning of R$^{12}$ given above
or
R$^{20}$ and R$^{21}$ together with the nitrogen atom form a radical of the formula

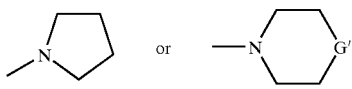

in which
G' has the meaning of G given above,
R$^2$ and R$^3$ are identical or different and represent hydrogen or (C$_1$–C$_6$)-alkyl,
and
D and E together form radicals of the formulae

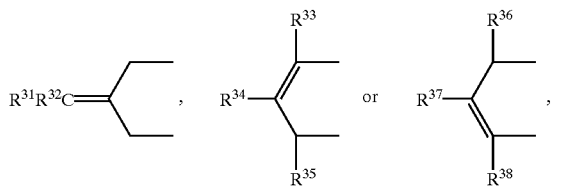

in which
R$^{31}$, R$^{32}$, R$^{33}$, R$^{34}$, R$^{35}$, R$^{36}$, R$^{37}$ and R$^{38}$ are identical or different and represent hydrogen, phenyl or (C$_1$–C$_6$)-alkyl,
and their pharmaceutically acceptable salts.

2. Compounds of the formula (I) according to claim 1, in which
A represents radicals of the formulae —CH$_2$—, —CO—, —CR$^4$(OH)— or —(CH$_2$)$_a$—CHR$^5$—,
in which
a represents a number 0, 1, 2 or 3,
R$^4$ represents hydrogen or (C$_1$–C$_4$)-alkyl
and
R$^5$ represents phenyl,
or
represents (C$_2$–C$_6$)-alkanediyl, (C$_2$–C$_4$)-alkenediyl or (C$_2$–C$_4$)-alkinediyl,
R$^1$ is a morpholine ring attached to A via the nitrogen atom,
wherein said ring systems is optionally mono- to polysubstituted by identical or different substituents selected from the group consisting of fluorine, chlorine, bromine, iodine, cyano, nitro, trifluoromethyl, hydroxyl or (C$_1$–C$_5$)-alkoxy, (C$_1$–C$_5$)-alkylcarbonyloxy, cyclopropyl, cyclopentyl, cyclohexyl, phenyl, phenoxy, pyridyl, pyrimidyl, pyridazinyl, thienyl, furyl or benzyloxy, which for their part may be substituted up to three times by identical or different substituents from the group consisting of cyano, fluorine, chlorine, bromine and iodine,
and/or are substituted by (C$_1$–C$_5$)-alkyl and (C$_2$–C$_4$)-alkenyl, which for their part may be substituted by fluorine, chlorine, bromine, iodine, phenyl, naphthyl or by radicals of the formula —SR$^8$, —OR$^9$ or —NR$^{10}$R$^{11}$ or

in which
R$^8$ represents (C$_1$–C$_4$)-alkyl or phenyl,
R$^9$ represents hydrogen or (C$_1$–C$_4$)-alkyl, and
R$^{10}$ and R$^{11}$ are identical or different and represent hydrogen, phenyl or (C$_1$–C$_4$)-alkyl, which is optionally substituted by phenyl, which for its part may be mono- to polysubstituted by identical or different substituents from the group consisting of fluorine, chlorine, bromine, nitro, hydroxyl and (C$_1$–C$_4$)-alkoxy,
or
R$^{10}$ and R$^{11}$ together with the nitrogen atom form a radical of the formula

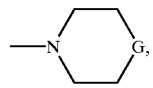

in which
G represents an oxygen atom, a —CH$_2$— group or a radical of the formula —NR$^{12}$—,
in which
R$^{12}$ represents hydrogen, phenyl, benzyl, (C$_1$–C$_4$)-alkyl, (C$_1$–C$_4$)-alkoxycarbonyl, pyridyl, pyrimidyl, pyridazinyl or furyl,
and/or are substituted by groups of the formulae —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$,
in which
R$^{13}$ represents hydrogen, or represents (C$_1$–C$_8$)-alkyl or (C$_2$–C$_5$)-alkenyl, which for their part may be substituted by radicals of the formulae

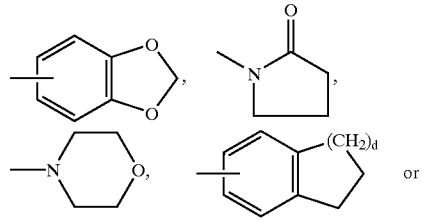

phenyl, naphthyl, pyridyl, thienyl or furyl,
in which
d represents a number 1 or 2,
or
represents phenyl or naphthyl, which are optionally substituted by phenyl, which for its part may be substituted by cyano, fluorine, chorine or bromine,
R$^{14}$ and R$^{15}$ are identical or different and represent hydrogen, cyclopropyl, cyclopentyl, cyclohexyl, phenyl or (C$_1$–C$_5$)-alkyl, which is optionally substituted by cyclopropyl, cyclopentyl, cyclohexyl or phenyl, which for its part may be mono- to polysubstituted by identical or different substituents from the group consisting of fluorine, chlorine, bromine, hydroxyl or $(C_1-C_4)$-alkoxy, $R^{16}$ represents hydrogen or $(C_1-C_3)$-alkyl, $R^{17}$ represents hydrogen, adamantyl, cyclopropyl, cyclopentyl or cyclohexyl, or represents $(C_2-C_4)$-alkenyl or $(C_1-C_{10})$-alkyl, which is optionally substituted by adamantyl, cyclopropyl, cyclopentyl, cyclohexyl, phenyl, phenoxy-naphthyl, pyridyl, thienyl, tetrazolyl or furyl, where the ring systems for their part may be mono- to polysubstituted by identical or different substituents from the group consisting of $(C_1-C_4)$-alkyl, $(C_1-C_4)$-alkoxy, hydroxyl, nitro, fluorine, chlorine and bromine, and/or alkyl is optionally substituted by a radical of the formula

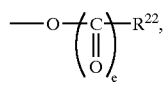

in which e represents a number 0 or 1 and $R^{22}$ represents $(C_1-C_4)$-alkyl, phenyl or naphthyl, which are optionally mono- to polysubstituted by identical or different substituents from the group consisting of fluorine, chlorine, bromine, nitro, hydroxyl and $(C_1-C_4)$-alkoxy, or represents phenyl, naphthyl, thienyl, furyl or pyridyl, which for their part may optionally be mono- to polysubstituted by identical or different substituents from the group consisting of $(C_1-C_4)$-alkoxy, $(C_1-C_4)$-alkyl, hydroxyl, nitro, fluorine, chlorine and bromine, or represents a radical of the formula

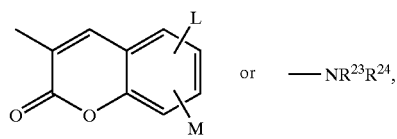

in which

L and M are identical or different and represent hydrogen, fluorine, chlorine or bromine, $R_{23}$ and $R_{24}$ have the meaning of $R_{10}$ and $R_{11}$ given above, $R^{18}$ has the meaning of $R^{16}$ given above, $R^{19}$ represents cyclopropyl, cyclopentyl or cyclohexyl, or represents $(C_1-C_7)$-alkyl or $(C_2-C_6)$-alkenyl, which for their part are optionally substituted by substituents selected from the group consisting of fluorine, chlorine, bromine, phenyl, hydroxyl, morpholinyl, cyclopropyl, cyclopentyl, cyclohexyl and by a group of the formula $-SiR^{25}R^{26}R^{27}$, in which $R^{25}$, $R^{26}$ and $R^{27}$ are identical or different and represent $(C_1-C_4)$-alkyl, $R^{20}$ and $R^{21}$ are identical or different and represent hydrogen, adamantyl, cyclopropyl, cyclopentyl, cyclohexyl, phenyl, phenoxy-substituted phenyl, pyridyl, furyl, thienyl, thiazolyl or pyrryl, or represent $(C_2-C_6)$-alkenyl, $(C_1-C_{10})$-alkyl or $(C_3-C_6)$-alkinyl, which are optionally substituted by hydroxyl, cyclopropyl, cyclopentyl, cyclohexyl, $(C_1-C_5)$-alkoxy, $(C_1-C_6)$-alkoxycarbonyl, fluorine, chlorine, bromine, hydroxyl, trifluoromethyl, phenyl, pyridyl, furyl, thienyl or pyrryl, where the ring systems are optionally substituted up to 2 times by identical or different substituents from the group consisting of $(C_1-C_4)$-alkoxy, fluorine, chlorine, bromine, phenoxy, hydroxyl or $(C_1-C_4)$-alkyl, and/or the alkyl listed under $R^{20}/R^{21}$ is optionally substituted by radicals of the formulae

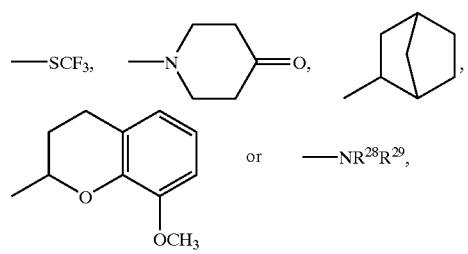

in which $R^{28}$ and $R^{29}$ are identical or different and represent hydrogen or $(C_1-C_4)$-alkyl, or or represents a radical of the formula

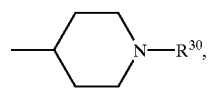

in which $R^{30}$ has the meaning of $R^{12}$ given above, or $R^{20}$ and $R^{21}$ together with the nitrogen atom form a radical of the formula

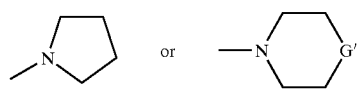

in which

G' has the meaning of G given above, $R^2$ and $R^3$ are identical or different and represent hydrogen or $(C_1-C_3)$-alkyl, and D and E together form radicals of the formulae in which $R^{31}$, $R^{32}$, $R^{33}$, $R^{34}$, $R^{35}$, $R^{36}$, $R^{37}$ and $R^{38}$ are identical or different and represent hydrogen, phenyl or $(C_1-C_3)$-alkyl, and their pharmaceutically acceptable salts.

3. Compounds of the formula (I) according to claim 1 or 2, in which

A represents radicals of the formulae —CH$_2$—, —CO—, —CR$^4$(OH)— or —(CH$_2$)$_a$—CHR$^5$—,
in which
a represents a number 0, 1, 2 or 3,
R$^4$ represents hydrogen or (C$_1$–C$_3$)-alkyl
and
R$^5$ represents phenyl,
or
represents (C$_2$–C$_4$)-alkanediyl, propenediyl or (C$_2$–C$_3$)-alkinediyl, R$^1$ is morpholine ring attached to A via the nitrogen atom, wherein said ring systems is optionally mono- to polysubstituted by identical or different substituents selected from the group consisting of fluorine, chlorine, bromine, iodine, cyano, nitro, trifluoromethyl or (C$_1$–C$_4$)-alkoxy, (C$_1$–C$_4$)-alkylcarbonyloxy, cyclohexyl, phenyl, phenoxy, pyridyl, pyrimidyl, pyridazinyl or benzyloxy, which for their part may be substituted up to three times by identical or different substituents from the group consisting of cyano, fluorine, chlorine, bromine and iodine,
and/or are substituted by (C$_1$–C$_4$)-alkyl and (C$_2$–C$_3$)-alkenyl, which for their part may be substituted by chlorine, bromine, iodine or phenyl or by radicals of the formula —OR$^9$ or —NR$^{10}$R$^{11}$ or

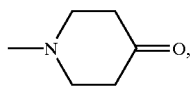

in which
R$^9$ represents hydrogen or (C$_1$–C$_3$)-alkyl,
and
R$^{10}$ and R$^{11}$ are identical or different and represent hydrogen, phenyl or (C$_1$–C$_3$)-alkyl, which is optionally substituted by phenyl, which for its part may be substituted by chlorine, bromine, hydroxyl or (C$_1$–C$_3$)-alkoxy,
or
R$^{10}$ and R$^{11}$ together with the nitrogen atom form a radical of the formula

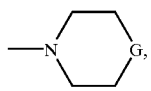

in which
G represents an oxygen atom or a radical of the formula —NR$^{12}$—,
in which
R$^{12}$ represents hydrogen, phenyl, benzyl, (C$_1$–C$_3$)-alkyl, (C$_1$–C$_3$)-alkoxycarbonyl, pyridyl, pyrimidyl, pyridazinyl or furyl,
and/or are substituted by groups of the formulae —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$,
in which
R$^{13}$ represents hydrogen, or
represents (C$_1$–C$_6$)-alkyl or allyl, which for their part may be substituted by radicals of the formulae

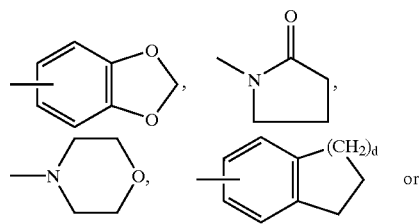

in which
d represents a number 1 or 2,
or
represents phenyl, which is optionally substituted by phenyl, which for its part may be substituted by cyano, chlorine or bromine,
R$^{14}$ and R$^{15}$ are identical or different and represent hydrogen, cyclohexyl, phenyl or (C$_1$–C$_4$)-alkyl, which is optionally substituted by cyclopropyl, cyclohexyl or phenyl, which for its part may be mono- to polysubstituted by identical or different substituents from the group consisting of chlorine and (C$_1$–C$_3$)-alkoxy,
R$^{16}$ represents hydrogen, methyl or ethyl,
R$^{17}$ represents hydrogen, adamantyl, cyclopentyl or cyclohexyl, or
represents (C$_2$–C$_3$)-alkenyl or (C$_1$–C$_8$)-alkyl, which is optionally substituted by adamantyl, cyclopropyl, cyclopentyl, cyclohexyl, phenyl, phenoxy, thienyl or furyl, where the ring systems for their part may be mono- to polysubstituted by identical or different substituents from the group consisting of (C$_1$–C$_3$)-alkyl, (C$_1$–C$_3$)-alkoxy, hydroxyl, nitro, fluorine, chlorine and bromine,
and/or alkyl is optionally substituted by a radical of the formula

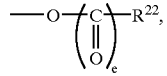

in which
e is a number 0 or 1 and
R$^{22}$ represents (C$_1$–C$_3$)-alkyl, phenyl or naphthyl, which are optionally mono- to polysubstituted by identical or different substituents from the group consisting of fluorine, chlorine, bromine, nitro, hydroxyl and (C$_1$–C$_3$)-alkoxy,
or
represents phenyl, naphthyl, thienyl or furyl, which for their part may optionally be mono- to polysubstituted by identical or different substituents from the group consisting of (C$_1$–C$_3$)-alkoxy, (C$_1$–C$_3$)-alkyl, nitro, fluorine, chlorine and bromine,
or
represents a radical of the formula

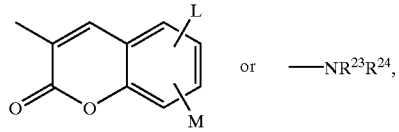

in which
L and M are identical or different and represent hydrogen, fluorine or chlorine,

219

$R^{23}$ and $R^{24}$ have the meaning of $R^{10}$ and $R^{11}$ given above, $R^{18}$ has the meaning of $R^{16}$ given above, $R^{19}$ represents $(C_1-C_4)$-alkyl or $(C_3-C_5)$-alkenyl, which for their part are optionally substituted by substituents selected from the group consisting of chlorine, phenyl, hydroxyl, morpholinyl, cyclopropyl, cyclohexyl and by a group of the formula $-SiR^{25}R^{26}R^{27}$, in which $R^{25}$, $R^{26}$ and $R^{27}$ are identical and represent methyl, $R^{20}$ and $R^{21}$ are identical or different and represent hydrogen, adamantyl, cyclopropyl, cyclopentyl, cyclohexyl, phenyl, phenoxy-substituted phenyl, thiazolyl or pyrryl, or represent $(C_2-C_3)$-alkenyl, $(C_1-C_7)$-alkyl or $(C_3-C_5)$-alkinyl, which are optionally substituted by hydroxyl, cyclopropyl, cyclopentyl, cyclohexyl, $(C_1-C_3)$-alkoxy, hydroxyl, trifluoromethyl, phenyl, pyridyl, furyl, thienyl or pyrryl, where the ring systems are optionally substituted up to 2 times by identical or different substituents from the group consisting of $(C_1-C_3)$-alkoxy, $(C_1-C_6)$-alkoxycarbonyl, fluorine, chlorine, bromine, phenoxy, hydroxyl and $(C_1-C_3)$-alkyl, and/or the alkyl listed under $R^{20}/R^{21}$ is optionally substituted by radicals of the formulae

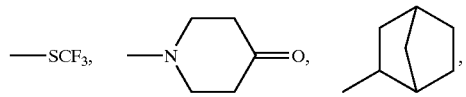

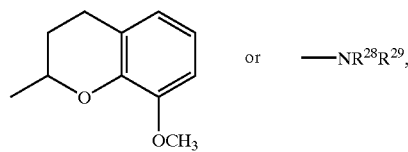

in which $R^{28}$ and $R^{29}$ are identical or different and represent hydrogen or $(C_1-C_3)$-alkyl, or or $R^{20}$ or $R^{21}$ represents a radical of the formula

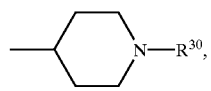

in which $R^{30}$ has the meaning of $R^{12}$ given above, or $R^{20}$ and $R^{21}$ together with the nitrogen atom form a radical of the formula

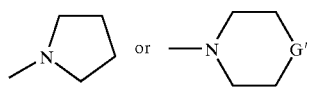

in which

G' has the meaning of G given above,

220

$R^2$ and $R^3$ are identical or different and represent hydrogen or methyl, and D and E together form radicals of the formulae

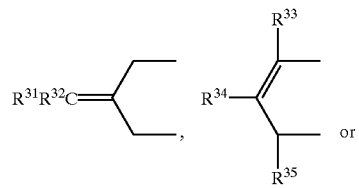

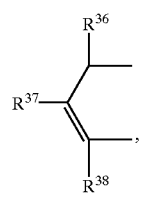

in which $R^{31}$, $R^{32}$, $R^{33}$, $R^{34}$, $R^{35}$, $R^{36}$, $R^{37}$ and $R^{38}$ are identical or different and represent hydrogen or methyl, and their pharmaceutically acceptable salts.

4. Compounds of the general formula (I) according to any of claim 1, in which A represents the $-CH_2-$ group; and $R^1$, $R^2$, $R^3$, D, and E are as defined in claim 1.

5. Compounds of the formula (I) according to claim 1, in which

A represents $-CH_2-$, $R^1$ is a morpholine ring attached to A via the nitrogen atom, wherein said ring systems is optionally mono- to polysubstituted by identical or different substituents selected from the group consisting of fluorine, chlorine, bromine, iodine, cyano, nitro, trifluoromethyl or $(C_1-C_4)$-alkoxy, and/or are substituted by $(C_1-C_4)$-alkyl, and/or are substituted by groups of the formulae $-NR^{16}CO-R^{17}$, $-NR^{18}CO_2-R^{19}$ and $-CO-NR^{20}R^{21}$, in which $R^{16}$ is hydrogen, $R^{17}$ is $(C_1-C_8)$-alkyl, which is optionally substituted by cyclopropyl, cyclopentyl, cyclohexyl, phenyl, thienyl or furyl, where the ring systems for their part may be mono- to polysubstituted by identical or different substituents from the group consisting of $(C_1-C_3)$-alkyl, $(C_1-C_3)$-alkoxy, hydroxyl, nitro, fluorine, chlorine and bromine, $R^{18}$ has the meaning of $R^{16}$ given above in claim 1, $R^{19}$ represents $(C_1-C_4)$-alkyl or $(C_1-C_5)$-alkenyl, $R^{20}$ and $R^{21}$ are identical or different and represent hydrogen, $(C_2-C_3)$-alkenyl, $(C_1-C_7)$-alkyl or $(C_3-C_5)$-alkinyl, which are optionally substituted by phenyl, pyridyl, furyl, thienyl or pyrryl, where the ring systems are optionally substituted up to 2 times by identical or different substituents from the group consisting of $(C_1-C_3)$-alkoxy, fluorine, chlorine, bromine and $(C_1-C_3)$-alkyl, $R^2$ and $R^3$ represent hydrogen or methyl, and
D and E together form radicals of the formulae

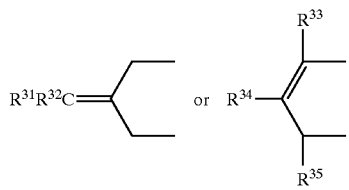

in which
$R^{31}$, $R^{32}$, $R^{33}$, $R^{34}$, $R^{35}$ represent hydrogen,
and their pharmaceutically acceptable salts.

6. Compounds according to any of claim 1, selected from the group consisting of:

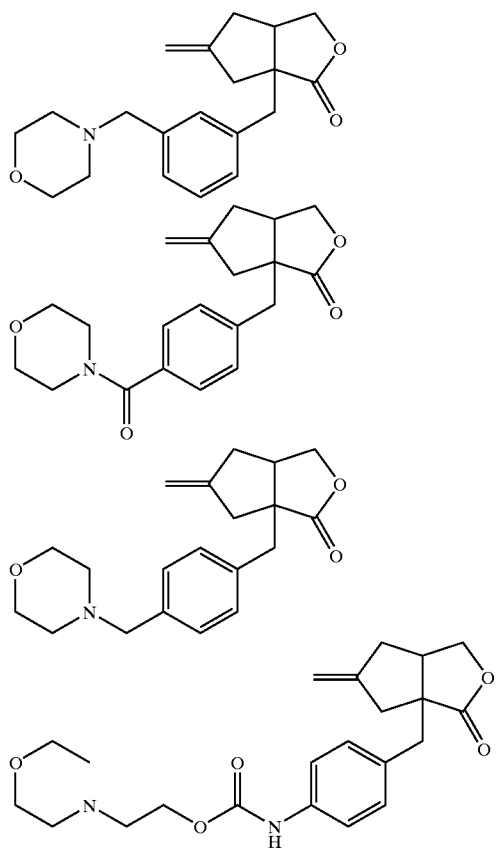

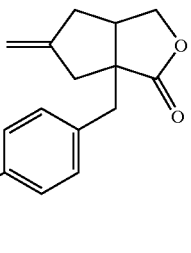

where these compounds can be present as a racemate or as a pure enantiomer.

7. Process for preparing the compounds of the formula (I) according to claim 1, by reacting compounds of the general formula (II)

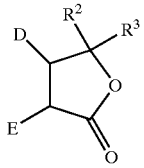 (II)

in which
D, E, $R^2$ and $R^3$ are as defined in claim 1,
with compounds of the general formula (III),

T—A—$R^1$ (III)

in which
T represents halogen,
and
A and $R^1$ are as defined above in claim 1,
in inert solvents and in the presence of a base.

8. Pharmaceutical composition, comprising as active component at least one compound according to claim 1 mixed together with at least one pharmaceutically acceptable, essentially non-toxic vehicle or excipient.

9. The process of claim 7, wherein T is bromine.

10. A method of treating disorders caused by hyper- or hypofunction of the glutamatergic system, comprising administering to a patient in need thereof an effective amount of a compound according to claim 1.

11. A method of treating cerebral ischaemias, craniocerebral trauma, states of pain or CNS-mediated spasms, comprising administering to a patient in need thereof an effective amount of a compound according to claim 1.

* * * * *